(12) United States Patent
Cottone et al.

(10) Patent No.: US 9,259,338 B2
(45) Date of Patent: *Feb. 16, 2016

(54) BIOABSORBABLE POLYMERIC MEDICAL DEVICE

(71) Applicant: OrbusNeich Medical Inc., Fort Lauderdale, FL (US)

(72) Inventors: Robert J. Cottone, Davie, FL (US); Shusheng Ye, Miami, FL (US); John Pazienza, Pompano Beach, FL (US)

(73) Assignee: ORBUSNEICH MEDICAL, INC., Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/445,606

(22) Filed: Jul. 29, 2014

(65) Prior Publication Data
US 2014/0336748 A1    Nov. 13, 2014

Related U.S. Application Data

(63) Continuation of application No. 13/738,337, filed on Jan. 10, 2013, now Pat. No. 8,834,557, which is a continuation of application No. 11/781,233, filed on Jul. 20, 2007, now Pat. No. 8,460,364, which is a (Continued)

(51) Int. Cl.
| | | |
|---|---|---|
| A61F 2/06 | (2013.01) | |
| A61F 2/82 | (2013.01) | |
| A61F 2/88 | (2006.01) | |
| A61F 2/86 | (2013.01) | |

(Continued)

(52) U.S. Cl.
CPC ... *A61F 2/86* (2013.01); *A61F 2/06* (2013.01);
*A61F 2/82* (2013.01); *A61F 2/91* (2013.01);
*A61F 2/915* (2013.01); *A61F 2/958* (2013.01);
*A61F 2002/9155* (2013.01); *A61F 2002/91508* (2013.01); *A61F 2002/91558* (2013.01); *A61F 2002/91566* (2013.01); *A61F 2002/91591* (2013.01); *A61F 2210/0004* (2013.01); *A61F 2220/0008* (2013.01); *A61F 2230/0013* (2013.01); *A61F 2230/0054* (2013.01)

(58) Field of Classification Search
USPC ........................................... 623/1.22, 1.16, 1.38
See application file for complete search history.

(56) References Cited

U.S. PATENT DOCUMENTS

| | | |
|---|---|---|
| 5,320,624 A | 6/1994 | Kaplan et al. |
| 5,322,925 A | 6/1994 | Muth et al. |

(Continued)

FOREIGN PATENT DOCUMENTS

| | | |
|---|---|---|
| CN | 1479596 A | 3/2004 |
| CN | 1509315 A | 6/2004 |

(Continued)

OTHER PUBLICATIONS

Office Action issued in corresponding Chinese Application No. 201310025670.4 on Aug. 12, 2014.

(Continued)

*Primary Examiner* — David H Willse
*Assistant Examiner* — Tiffany Shipmon
(74) *Attorney, Agent, or Firm* — Ascenda Law Group PC

(57) ABSTRACT

In embodiments there is described a cardiovascular tube-shaped lockable and expandable bioabsorbable scaffold having a low immunogenicity manufactured from a crystallizable bioabsorbable polymer composition or blend.

18 Claims, 53 Drawing Sheets

Related U.S. Application Data continuation-in-part of application No. 29/249,795, filed on Oct. 20, 2006, now Pat. No. Des. 597,671, which is a continuation-in-part of application No. 29/249,944, filed on Oct. 27, 2006, now Pat. No. Des. 568,476.

(60) Provisional application No. 60/862,433, filed on Oct. 20, 2006, provisional application No. 60/807,932, filed on Jul. 20, 2006, provisional application No. 60/913,264, filed on Apr. 20, 2007, provisional application No. 60/862,409, filed on Oct. 20, 2006.

(51) Int. Cl.
*A61F 2/91* (2013.01)
*A61F 2/915* (2013.01)
*A61F 2/958* (2013.01)

(56) References Cited

U.S. PATENT DOCUMENTS

| | | | |
|---|---|---|---|
| 5,827,322 | A | 10/1998 | Williams |
| 6,258,382 | B1 | 7/2001 | Takaoka et al. |
| 2002/0007212 | A1 | 1/2002 | Brown et al. |
| 2002/0188347 | A1 | 12/2002 | Mathis |
| 2004/0236406 | A1 | 11/2004 | Gregorich |
| 2005/0055080 | A1 | 3/2005 | Istephanous et al. |
| 2005/0107864 | A1 | 5/2005 | Hong et al. |
| 2005/0271701 | A1 | 12/2005 | Cottone |
| 2006/0025852 | A1 | 2/2006 | Armstrong et al. |
| 2006/0035854 | A1 | 2/2006 | Goldstein et al. |
| 2006/0069424 | A1 | 3/2006 | Acosta et al. |
| 2006/0173529 | A1 | 8/2006 | Blank |
| 2007/0032857 | A1 | 2/2007 | Schmid et al. |
| 2008/0051875 | A1 | 2/2008 | Cottone |
| 2008/0118546 | A1 | 5/2008 | Thatcher et al. |
| 2010/0094405 | A1 | 4/2010 | Cottone |

FOREIGN PATENT DOCUMENTS

| | | |
|---|---|---|
| WO | 9934750 | 7/1999 |
| WO | 2004080332 | 9/2004 |
| WO | 2008011175 | 1/2008 |
| WO | 2008089434 | 7/2008 |

OTHER PUBLICATIONS

EP Search Report issued in corresponding EP application No. 10775683.5 on May 30, 2014.
Extended European Search Report issued in corresponding EP application No. 07799752.6 on Jun. 25, 2012, 6 pgs.
Office Action issued in corresponding Chinese Application No. 201310312417.7 on Feb. 2, 2015, 15 pgs. with English translation.
International Search Report for the International Application No. PCT/US07/74052 issued by the International Searching Authority mailed on Jul. 3, 2008, 1 pg.
Written Opinion for the International Application No. PCT/US07/74052 issued by the International Preliminary Examining Authority mailed on Jul. 3, 2008, 3 pgs.
International Search Report for the International Application No. PCT/US07/16514 issued by the International Searching Authority mailed on Apr. 23, 2008, 1 pg.
Written Opinion for the International Application No. PCT/US07/16514 issued by the International Preliminary Examining Authority mailed on Apr. 23, 2008, 3 pgs.
International Search Report for the International Application No. PCT/US07/74050 issued by the International Searching Authority mailed on Aug. 5, 2008, 2 pg.
Written Opinion for the International Application No. PCT/US07/74050 issued by the International Preliminary Examining Authority mailed on Aug. 5, 2008, 3 pgs.
International Search Report for the International Application No. PCT/US07/74051 issued by the International Searching Authority mailed on Jan. 14, 2008, 3 pg.
Written Opinion for the International Application No. PCT/US07/74051 issued by the International Preliminary Examining Authority mailed on Jan. 14, 2008, 3 pgs.
International Search Report for the International Application No. PCT/US07/74053 issued by the International Searching Authority mailed on Jan. 14, 2008, 1 pg.
Written Opinion for the International Application No. PCT/US07/74053 issued by the International Preliminary Examining Authority mailed on Jan. 14, 2008, 3 pgs.

Material Strength

AMORPHOUS

CRYSTALLINE

Deformation

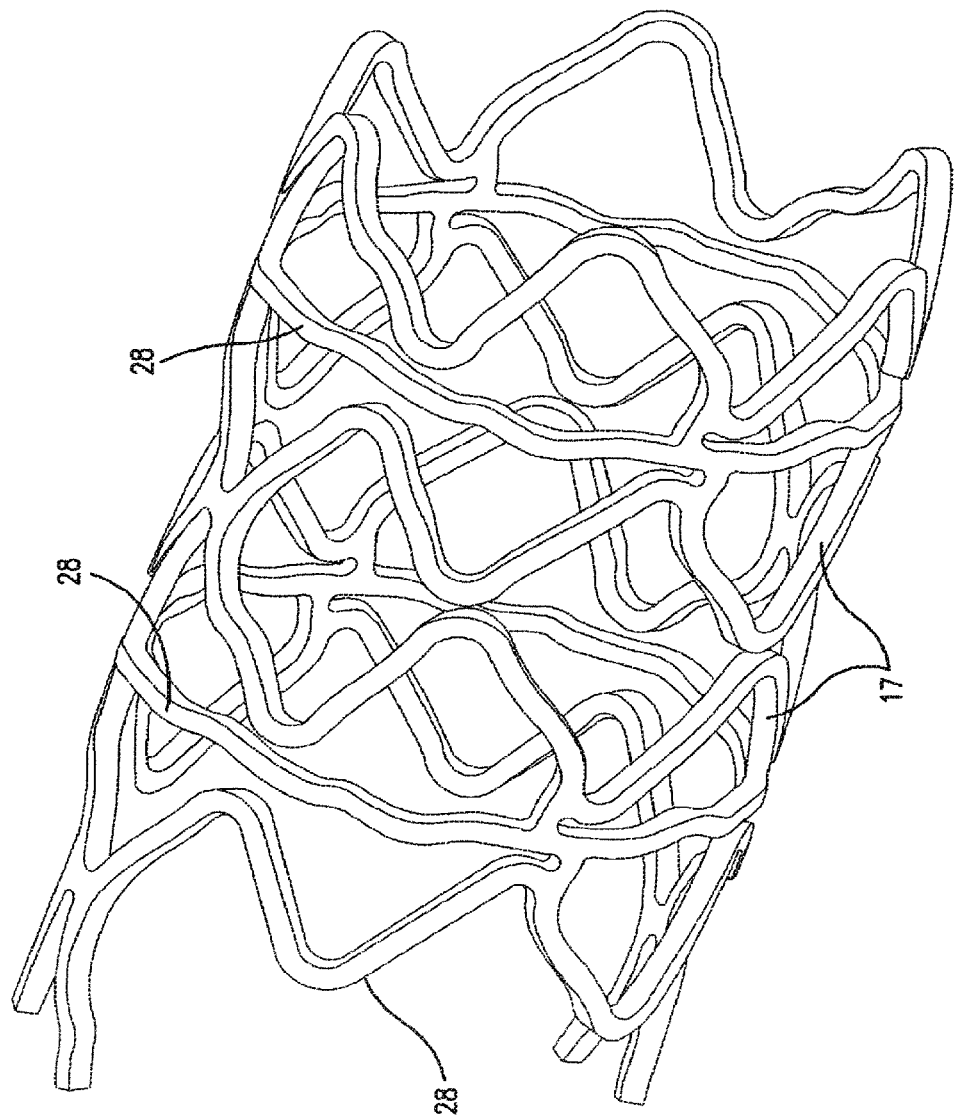

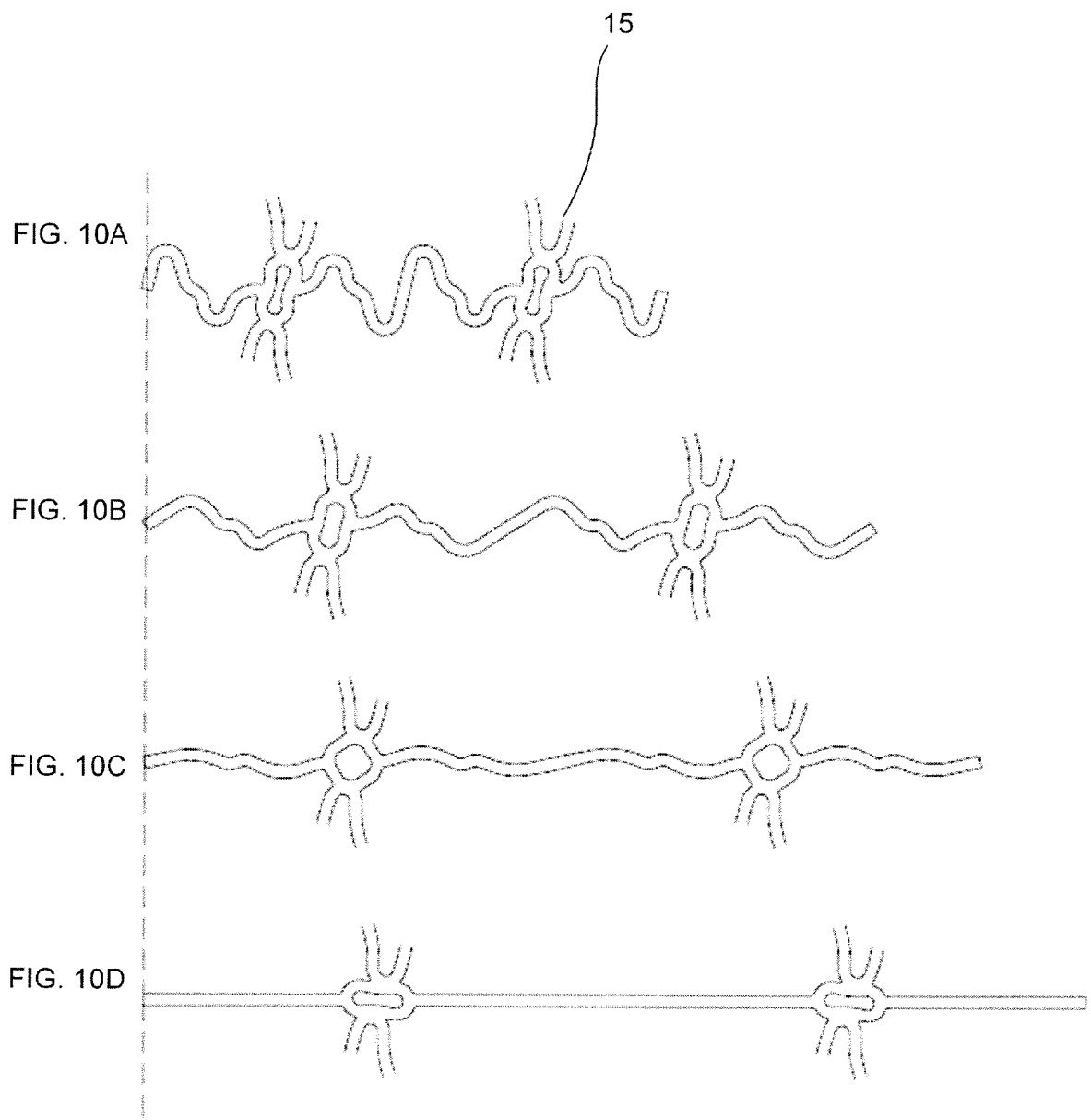

BIOABSORBABLE POLYMERIC MEDICAL DEVICE

This application is a continuation of U.S. application Ser. No. 13/738,337 filed Jan. 10, 2013, which is a continuation of U.S. application Ser. No. 11/781,233 filed Jul. 20, 2007 (now U.S. Pat. No. 8,460,364), which is a continuation-in-part of U.S. application Ser. No. 29/249,795 filed Oct. 20, 2006 (now U.S. Pat. No. D597,671) and Ser. No. 29/249,944 filed Oct. 27, 2006 (now U.S. Pat. No. D568,476). U.S. application Ser. No. 11/781,233 claims benefit of U.S. Provisional Application Nos. 60/913,264 (filed Apr. 20, 2007), 60/862,433 (filed Oct. 20, 2006), 60/862,409 (filed Oct. 20, 2006) and 60/807,932 (filed Jul. 20, 2006).

The references cited in this specification, and their references, are incorporated by reference herein in their entirety where appropriate for teachings of additional or alternative details, features, and/or technical background.

FIELD OF INVENTION

The invention relates to polymeric medical devices for implantation into luminal structures within the body. In particular, the medical device comprises a polymeric structure which polymer is bioabsorbable, biocompatible and structurally configured to fit within luminal structures such as blood vessels in the body. The medical device is useful for treating diseases such as atherosclerosis, restenosis and other types of cannalicular obstructions.

BACKGROUND

Disclosed in embodiments herein is a novel medical device, for example, a cardiovascular tube-shaped expandable scaffold having a meandering structural entity or plurality thereofuch novel medical device may include a locking mechanism at its end for securing the device in a crimped position onto a carrier means for deployment. The locking mechanism provides structural means for securing the crimped scaffold onto a carrier module so as to remain in an immobilized position during insertion and delivery to the treatment target area. The locked-in restraint of the scaffold can be maintained until implantation of the device or unless it is overcome by expansion means of the carrier module.

A persistent problem associated with the use of metallic stenting to treat, for example, vascular occlusion is found in the formation of scar tissue surrounding the device upon insertion of the device at the site of blood vessel injury, the so-called process of restenosis. Many have concluded that there is a continued risk of stent thrombosis due to the permanent aspect of metallic stents in the blood vessel, either alone or containing a drug coating composition, which therapy was intended to prevent such calamities. Moreover, metallic or non-absorbable polymeric stents may prevent vascular lumen remodeling and expansion.

It is known that any injury to body tissue or organ undergoes a wound healing process involving, for example, collagen type 1 synthesis and in particular, smooth muscle cell migration in particular from blood vessels, which result in concomitant hardening of the healed area and re-narrowing of the blood vessel diameter. Therefore, an invasive procedure to surgically implant a medical device, such as a stent into a blood vessel, should require a scaffold of enough plasticity to prevent vessel wall contusion or blood capillary injury during scaffold expansion and placement within the area of treatment.

Another long-term goal for avoiding restenosis is applying a surgical procedure with a medical device with none or substantially low immunogenicity The continued risk of stent thrombosis due to the permanency of metallic stents after implantation has not been overcome by coating of the metallic structures with drug compositions intended to prevent such problems. On the contrary, the death rate from these coatings has been prohibitive. Moreover, metallic or polymeric non-absorbable stents may prevent vascular lumen remodeling and expansion. Numerous approaches have been tried to prevent or heal tissue and reduce complement activation of the immune response or platelet aggregation. Furthermore, there is a need to eliminate or reduced an inflammatory response at the site of implantation, and lower potential for trauma upon break-up of an implant and/or its component materials. A most desirable improvement target may be found in the need for increased flexibility of shape and structure of medical devices for implantation, particularly into blood vessels.

REFERENCES

Reference is made to U.S. Pat. No. 6,607,548 B2 (Inion), issued Aug. 19, 2003, which discloses compositions of biocompatible and bioresorbable materials using a lactic acid or glycolic acid based polymer or copolymer blends with one or more copolymer additives. The reference discloses that implants made from these materials are cold-bendable without crazing or cracking. EP 0401844 discloses a blend of poly-L-lactide with poly-D-DL-lactide. U.S. Pat. No. 6,001,395 discloses drug delivery with lamellar particles of a biodegradable poly(L-lactide) or copolymers or blends thereof, being at least in part crystalline. U.S. Pat. No. 7,070,607 discloses an aneurysm repair coil comprising a bioabsorbable polymeric material carrying an embolic agent wherein thrombogenicity is controlled by the polymer composition.

SUMMARY

Among other things, the present inventors have recognized a need for improved implant configuration, including scaffold/stent configurations for in vivo application. The inventors have also recognized a need to develop a compatible polymer blend for implants, such as stents and vascular synthetic grafts, which provide a toughening mechanism to the base polymer when the medical device is deployed in the body. They have hypothesized that the later may be performed by imparting additional molecular free volume to the base polymer to encourage sufficient molecular motion to allow for re-crystallization to occur at physiological conditions especially when additional molecular strain is imparted to the implant. They have theorized that increased molecular free volume can also increase the rate of water uptake adding both a plasticizing effect as well as increasing the bulk degradation kinetics.

For example, the medical device could comprise a polymer with low immune rejection properties such as a bioabsorbable polymer composition or blend, having a combination of mechanical properties balancing elasticity, rigidity and flexibility. The polymer composition could produce a low antigenicity by means of a biocompatible base material, such as, without limitaton, a bioabsorbable polymer, copolymer, or terpolymer, and a copolymer or terpolymer additive. These kinds of polymer structures may advantageously undergo enzymatic degradation and absorption within the body. In particular, the novel composition may allow for a "soft" breakdown mechanism that is so gradual that the breakdown products or polymer components are less injurious to the surrounding tissue and thus reduce restenotic reactions or inhibit restenosis entirely.

The present inventors have also proposed novel designs which may employ such bioabsorbable, biocompatible and biodegradable material to make advantageous scaffolds, which may afford a flexibility and stretchability very suitable for implantation in the pulsatile movements, contractions and relaxations of, for example, the cardiovascular system.

Embodiments disclosed herein include, medical devices such as stents, synthetic grafts and catheters, which may or may not comprise a bioabsorbable polymer composition for implantation into a patient.

In one embodiment, a cardiovascular tube-shaped expandable scaffold such as a stent is provided, having a low rejection or immunogenic effect after implantation, which is fabricated from a bioabsorbable polymer composition or blend having a combination of mechanical properties balancing elasticity, rigidity and flexibility, which properties allow bending and crimping of the scaffold tube onto an expandable delivery system for vascular implantation. The instant devices can be used in the treatment of, for example, vascular disease such as atherosclerosis and restenosis, and can be provided in a crimpable and/or expandable structure, which can be used in conjunction with balloon angioplasty.

In an embodiment, the medical device can be provided as an expandable scaffold, comprising a plurality of meandering strut elements or structures forming a consistent pattern, such as ring-like structures along the circumference of the device in repeat patterns (e.g., with respect to a stent, without limitation, throughout the structure, at the open ends only, or a combination thereof). The meandering strut structures can be positioned adjacent to one another and/or in oppositional direction allowing them to expand radially and uniformly throughout the length of the expandable scaffold along a longitudinal axis of the device. In one embodiment, the expandable scaffold can comprise specific patterns such as a lattice structure, dual-helix structures with uniform scaffolding with optionally side branching.

In one embodiment, a bioabsorbable and flexible scaffold circumferential about a longitudinal axis so as to form a tube, the tube having a proximal open end and a distal open end, and being expandable from an unexpanded structure to an expanded form, and being crimpable, the scaffold having a patterned shape in expanded form comprising:
a) a plurality of first meandering strut patterns, each of the first meandering strut pattern being interconnected to one another to form an interconnected mesh pattern circumferential about the longitudinal axis; and
b) at least two second strut patterns nested within the interconnected mesh pattern, each of said second strut patterns comprising a hoop circumferential about the longitudinal axis, said hoop having an inner surface proximal to the longitudinal axis and an outer surface distal to the longitudinal axis, the hoop inner and outer surfaces about their circumferences being orthogonal to the longitudinal axis and within substantially the same plane.

In one embodiment, the first meandering strut patterns can be generally parallel to said longitudinal axis, generally diagonal to said longitudinal axis, generally orthogonal to said longitudinal axis, or generally concentric about said longitudinal axis. The second strut patterns can be made of a material, which substantially crystallizes when said tube is in its expanded state, but does not substantially crystallize in its unexpanded state. The second strut patterns can include at least one hoop having a through-void, wherein said through-void is configured to permit the radius of said at least one hoop to be expanded when said at least one hoop is subject to an expanding force which exceeds its nominal expanded state but does not result in hoop failure.

In one embodiment, each of the first meandering strut patterns of the scaffold is essentially sinusoidal, and each of the second strut patterns is substantially non-sinusoidal. The first meandering strut patterns of a scaffold can extend from the proximal open end to the distal open end of the tube. In another embodiment, each of the second strut patterns can be found at the proximal open end and the distal open end. In one embodiment, each of the second strut patterns is further found between the proximal open end and the distal open end.

In one embodiment, the scaffold can comprise a structure wherein each of the second strut patterns can be found between the proximal open end and the distal open end but not at the proximal open end or distal open end. In another embodiment, the scaffold can comprise a structure wherein the second strut patterns can be found at at least one of the proximal open end or the distal open end.

In a specific embodiment, the scaffold comprises a stent having an unexpanded configuration and an expanded configuration; an outer tubular surface and an inner tubular surface, the stent comprising: a plurality of biodegradable, paired, separate circumferential bands having a pattern of distinct undulations in an unexpanded configuration and substantially no undulations in an expanded configuration, the undulations of the biodegradable, paired, separate circumferential bands in the stent in an unexpanded state being incorporated into a substantially planar ring in an expanded state, and a plurality of biodegradable interconnection structures spanning between each pair of circumferential bands and connected to multiple points on each band of the paired bands.

In an embodiment, the stent interconnecting structures comprise a pattern of undulations both in an unexpanded and expanded configuration. In an alternate embodiment, the interconnection structures comprise a pattern containing no undulations in both an unexpanded and expanded configuration. The interconnection structures of the stent can expand between undulations of paired circumferential bands.

In one embodiment, at least one of the plurality of paired biodegradable circumferential bands includes along its outer tubular surface, a radio-opaque material capable of being detectable by radiography, MRI or spiral CT technology. Alternatively, at least one of the interconnection structures includes a radio-opaque material along its outer tubular surface, which can be detectable by radiography, MRI or spiral CT technology. The radio-opaque material can be housed in a recess on one of the circumferential bands, or in a recess on one of the interconnection structures. In one embodiment, at least one of the interconnection structures and at least one of the circumferential bands includes a radio-opaque material along the outer tubular surface, which is detectable by radiography, MRI or spiral CT technology.

In another embodiment, a biosorbable and flexible scaffold circumferential about a longitudinal axis and substantially forming a tube, the tube having a proximal open end and a distal open end, and being crimpable and expandable, and comprising in expanded form: a) at least two rings circumferential about the longitudinal axis, the rings having an inner surface proximal to the longitudinal axis, an outer surface distal to the longitudinal axis, a top surface proximal to the proximal open end and a bottom surface proximal to the distal open end, the ring inner and outer surfaces about their circumferences being orthogonal to the longitudinal axis and within substantially the same plane, and b) a plurality of meandering strut patterns located between the at least two rings and circumferential coursing about the longitudinal axis; the plurality of meandering strut patterns connected to the rings at at least two connection points on the circumference of each ring, and each connection point on the circumference of the ring on both the top ring surface and the bottom ring surface; wherein each of the connection points with any particular ring is symmetrical in structure above and below the upper and lower surface of the ring.

In one embodiment, the scaffold comprises a structure wherein the connection points of the rings, the meandering strut patterns above the ring upper surface and below the ring lower surface in conjunction form a stylized, letter H configuration. In another embodiment, the scaffold can comprise a structure wherein at the connection points of the rings, the meandering strut patterns above the ring upper surface and below the ring lower surface in conjunction form two abutting sinusoids. In an alternate embodiment, the scaffold can comprise a structure wherein at the connection points of the rings, the meandering strut patterns above the ring upper surface and below the ring lower surface in conjunction form two sinusoids with intervening structure connecting the same and the ring. In one embodiment, the connection points of the rings have between 2 through 6 meandering strut pattern connections at each connection.

In another embodiment, an expandable biodegradable tubular scaffold comprising a plurality of biodegradable first meanders forming an interconnected mesh. The mesh extending circumferentially about a longitudinal axis; wherein each of the biodegradable first meanders are manufactured from a racemic polymer which crystallizes under the strain of expansion of the tubular scaffold, and also comprising a plurality of biodegradable second meanders, each of the second meanders being separate from another, and each extending circumferentially about the longitudinal axis in a single plane, the second meanders being nested in, and interconnected to, the first meanders. In this embodiment, the scaffold's first meanders are generally parallel to the longitudinal axis, generally diagonal to the longitudinal axis, generally orthogonal to the longitudinal axis, or are concentric about the longitudinal axis. The second meanders are made from a material which crystallizes when the tube is in its expanded state, but does not substantially crystallize in its unexpanded state, and at least one of the second meanders includes at least one through-void, which is configured to permit stretching of the second member without failure of the member.

In one embodiment, the first meanders form a strut pattern that is sinusoidal when the tube is in an expanded form, the second meanders form a strut pattern that is substantially non-sinusoidal when the tube is in an expanded form. In this and other embodiments, the first meanders form a strut pattern that extends from the proximal open end to the distal open end of the tube, and the second meanders form a strut pattern that is found at the proximal open end and the distal open end. The second meanders can also form a strut pattern that is further found between the proximal open end and the distal open end, or the second meanders form a pattern that is found between the proximal open end and the distal open end but not at the proximal open end or the distal open end.

In an alternate embodiment, a method for fabricating a tube-shaped scaffold comprising: preparing a racemic poly-lactide mixture; fabricating a biodegradable polymer tube of the racemic poly-lactide mixture; laser cutting the tube until such scaffold is formed. In this embodiment, the fabrication of the scaffold can be performed using a molding technique, which is substantially solvent-free, or an extrusion technique.

There is also provided a method for fabricating the tube-shaped scaffold comprising, blending a polymer composition comprising a crystallizable composition comprising a base polymer of poly L-lactide or poly D-lactide linked with modifying copolymers comprising poly L(or D)-lactide-co-trimethylene-carbonate or poly L(or D)-lactide-co-e-caprolactone in the form of block copolymers or as blocky random copolymers wherein the lactide chain length is sufficiently long enough to allow cross-moiety crystallization; molding the polymer composition to structurally configure the scaffold; and cutting the scaffold to form the desired scaffold patterns. In this embodiment, the blended composition comprises a recemic misture of poly L-lactide and poly-D lactide. Accordingly, medical devices such as a stent, produced by this method consist essentially of a racemic mixture of a poly-L and poly-D lactide. In this embodiment, the stent can comprise other polymer materials such as trimethylcarbonate. In embodiment wherein the device comprises trimethylcarbonate, the amount of trimethylcarbonate does not exceed more than 40% of the weight of the stent.

In another embodiment, an expandable tube-shaped scaffold having a proximal end and a distal end defined about a longitudinal axis is provided. The scaffold comprising: (a) a plurality of first meandering strut elements interconnected with one another at least one point in such a manner to form a circumferential tube-shaped structure, the first meandering strut elements forming a tubular mesh which is crimpable and expandable; (b) a second meandering strut element which is operatively configured to be crimpable and expandable and configured to form a hoop-shaped strut of the scaffold after expansion; and (c) a locking means permitting the scaffold to be locked in a crimped position; wherein the scaffold comprises a expansion crystallizable, bioabsorbable racemate polymer composition or blend.

In one lock embodiment, the tube-shaped scaffold can comprise a structure wherein the locking means is a two-part portion of one or different meandering strut elements located at or near both the proximal and distal ends of the tube-shaped scaffold. In this embodiment, the two-part portion of the locking means can entail, for example, a snap-fit engagement in the crimped position of the scaffold, wherein the locking means is disengaged by scaffold expansion. In alternate embodiments, the tube-shaped scaffold can comprise a locking means comprising a snap-fit key-in-lock configuration wherein the design resembles a dovetail type interlocking means. The tube-shaped scaffold can also comprise locking means comprising a snap-fit key-in-lock configuration resembling a ball-joint type interlocking means; a cantilever arm hooking an oppositely shaped end piece of the plastic scaffold, and the like.

The tube-shaped scaffold can be mounted or carried on a expandable balloon carrier device and can be sized to stretch from a crimped tube diameter to a diameter sufficient for implantation inside the lumen of a vascular system.

In another embodiment, the expandable scaffold comprises a set of interlocking meandering struts stabilizing the implanted scaffold in an expanded or implanted configuration, wherein the scaffold polymer undergoes a molecular reorientation and crystallization during the radial strain of expansion. The scaffold can vary from a cylindrical to a conal shape or combination thereof. In the embodiments described herein, the scaffold's biodegradable polymer displays breakdown kinetics sufficiently slow to avoid tissue overload or other inflammatory reactions. The polymer core material comprising at least one encapsulated drug for localized treatment of the vascular wall and lumen.

The tube-shaped scaffold can also comprise one or more than one pharmaceutical substances, which can be encapsulated within the polymeric structure for release of the drugs locally and for the treatment and prevention of tissue inflammation and platelet aggregation. The tube-shaped scaffold can also comprise at least one attached or embedded identification marker, which can be attached or embedded identification marker comprising a spot radioopacity or a diffuse radioopacity.

The tube-shaped scaffold can also comprise meandering struts which can be interlocked by means of ringlet connectors comprising configurations selected from one or more of the groups consisting of: shaped-like an H, shaped-like an X, perforated circle, double adjacent H, triple adherent connection, two adjacent parallel connections, sinusoidal connect of parallel struts.

In another embodiment, a bioabsorbable and flexible scaffold circumferential about a longitudinal axis so as to form a tube, the tube having a proximal open end and a distal open end, and being crimpable and expandable, comprising (a) a plurality of first meandering strut elements interconnected with one another at least points in such a manner to form a circumferential tube-shaped structure, the first meandering strut elements forming a tubular mesh which is crimpable and expandable; (b) a second meandering strut element which is operatively configured to be crimpable and expandable and configured to form a hoop-shaped strut of the scaffold after expansion the hooped-shaped strut having a inner surface proximal to the longitudinal axis, an outer surface distal to the longitudinal axis, a top surface proximal to the proximal open end and a bottom surface proximal to the distal open end; the second meandering strut element interconnected the plurality of first meandering strut elements; and (c) at least a pair of locking structures located proximal to either of the inner surface or the outer surface of the second meandering strut element, the pair of locking structures being configured to operatively lock to one another when the scaffold is in an unexpanded state, but to separate from one another when the scaffold is in an expanded state.

The scaffold can comprise locking structures comprising a pair of cantilevered arms that interconnect with one another when the scaffold is in an unexpanded state; locking structures comprising opposing male and female connectors; locking structures comprising connectors adjoined to one another with a friable connection when the scaffold is in an unexpanded state, but separate connectors when the friable connection is broken when the scaffold is in an expanded state; locking structures comprising a dovetail-type interlocking connectors; locking structures comprising a cantilevered arm and a portion of the a second meandering strut element when the scaffold is in an unexpanded state, and form a cantilevered arm extending from, and a recess in, the second meandering strut element when the scaffold is in an unexpanded state. The locking structures can be configured and positioned with respect to such tube to allow for locking of an unexpanded state, and when carried on a expandable balloon carrier device.

In another embodiment, a crimpable bioabsorbable and flexible scaffold circumferential about a longitudinal axis so as to form a tube, the tube having a proximal open end and a distal open end, and being expandable from an unexpanded to an expanded form, and containing locking structure to lock one component of the scaffold to another, the scaffold having a patterned shape in expanded form comprising, (a) a plurality of first meandering strut patterns, each of the first meandering strut pattern being interconnected to one another to form an interconnected mesh pattern circumferential about the longitudinal axis; and (b) at least two second strut patterns nested within the interconnected mesh pattern, each of the second strut patterns comprising a hoop circumferential about the longitudinal axis, the hoop having an inner surface proximal to the longitudinal axis and an outer surface distal to the longitudinal axis, the hoop inner and outer surfaces about their circumferences being orthogonal to the longitudinal axis and within substantially the same plane.

The expandable tubular scaffold comprises one or more of the first meanders include receptacle structure for lock-fit reception of corresponding lock structure. The expandable tubular scaffold comprises a structure wherein the corresponding locking structure is part of the one or more of first meanders, which incorporate thereon receptacle structure, and the corresponding locking structure is locked with respect to the receptacle structure. In one embodiment, the expandable tubular scaffold also comprises one or more of the second meanders includes receptacle structure for lock-fit reception of corresponding lock structure, which further includes the corresponding locking structure, and the corresponding locking structure is locked with respect to the receptacle structure. In one embodiment, the expandable tubular comprises a structure wherein one or more of the first meanders includes receptacle structure for lock-fit reception of corresponding lock structure.

In another embodiment, the expandable tubular scaffold comprises a structure wherein one or more of the second meanders includes corresponding lock structure for the receptacle structure, and the corresponding locking structure is locked with respect to the receptacle structure; or one or more of the second meanders includes receptacle structure for lock-fit reception of corresponding lock structure.

In an alternate embodiment, the expandable tubular scaffold comprises a structure wherein one or more of the first meanders includes the corresponding lock structure, the corresponding locking structure is locked with respect to the receptacle structure.

In another embodiment, a biosorbable and flexible scaffold circumferential about a longitudinal axis so as to form a tube, the tube having a proximal open end and a distal open end, and being crimpable and expandable, and having a patterned shape in expanded form comprising, a first multicomponent strut pattern helically coursing from the proximal open end to the distal open end of the tube; a second multicomponent strut pattern helically coursing from the proximal open end to the distal open end of the tube; wherein a component of the first multicomponent strut pattern opposes by from about 120° to about 180° a component of the second multicomponent strut pattern as each helically courses from the proximal open end to the distal open end of the tube. In one embodiment, the scaffold comprises a structure wherein each component strut pattern of the first multicomponent strut pattern is substantially the same in configuration. The scaffold can also comprise a structure wherein each component strut pattern of the second multicomponent strut pattern is substantially the same in configuration. Alternatively, the scaffold can comprise a structure wherein each component strut pattern of the first and second multicomponent strut pattern is substantially the same in configuration. In this embodiment, that is, wherein each opposing component of the component strut pattern between the first multicomponent strut pattern and second multicomponent strut pattern is substantially the same in configuration; and can form an stylized letter H configuration; a stylized X configuration; a stylized S configuration; a stylized 8 configuration; or a stylized I configuration.

The scaffold can comprise a third multicomponent strut pattern helically coursing from the proximal open end to the distal open end of the tube. The scaffold can further comprise a fourth multicomponent strut pattern helically coursing from the proximal open end to the distal open end of the tube, and a fifth multicomponent strut pattern helically coursing from the proximal open end to the distal open end of the tube. Each helix of a pair of the multicomponent strut patterns may turn about the tube in a left-handed screw direction. Alternatively, the scaffold can comprise a structure wherein each helix of both of the multicomponent strut patterns turns about the tube in a right-handed screw direction. In a further embodiment, at least one helix of both of the multicomponent strut patterns turns about the tube in a left-handed screw direction while another helix turns in a right-handed screw direction. In yet another embodiment, all of the helices of the multicomponent strut patterns turns about the tube in the same-handed direction.

In another embodiment, there is disclosed a biosorbable stent having a plurality of helically coursing multicomponent strut patterns from the proximal open end to the distal open end of the tube wherein a component of each the multicomponent strut pattern opposes by from about 120° to about 180° another component of another multicomponent strut pattern as each helically courses from the proximal open end to the distal open end of the tube. In this embodiment, each helix of the multicomponent strut patterns turns about the stent in a left-handed screw direction; each helix of both of the multicomponent strut patterns may turn about the stent in a right-handed screw direction. Alternatively, the scaffold can comprise helices wherein at least one helix of the multicomponent strut patterns turns in a left-handed screw direction while another helix turns about the stent in a right-handed screw direction; or wherein all of the helices of the multicomponent strut patterns turns about the stent in the same handed direction.

There is also provided, a flexible scaffold circumferential about a longitudinal axis so as to form a tube, the tube having a proximal open end and a distal open end, and being crimpable and expandable, and having a patterned shape in unexpanded form comprising; a first sinusoidal strut pattern comprising a series of repeated sinusoids defined by an apex section and a trough section, the repeated sinusoids coursing from the proximal open end to the distal open end of the tube; and a second sinusoidal strut pattern comprising a series of repeated sinusoids defined by an apex section and a trough section, the sinusoids of the second sinusoidal strut pattern being about 180° out of phase to with respect to the apex and the troughs of the first sinusoidal strut pattern; wherein the second sinusoidal strut pattern is connect to the first sinusoidal strut pattern at at least two points, and wherein the connection at the points is from an apex of a sinusoid of the first sinusoidal pattern to an apex of a sinusoid of the second sinusoidal pattern.

In one embodiment, the scaffold can comprise a structure wherein the first sinusoidal strut pattern and the second sinusoidal strut pattern are repeated multiple times, one after the other to form the scaffold; or wherein the first sinusoidal strut pattern and the second sinusoidal strut pattern are the same; or wherein the first sinusoidal strut pattern and the second sinusoidal strut pattern are different. The scaffold can be made of a biodegradable material, such as poly-lactide. In this embodiment, the scaffold comprises a structure wherein the second sinusoidal strut pattern is connected to the first sinusoidal strut pattern at at least three or four points.

In another embodiment, a biosorbable and flexible scaffold circumferential about a longitudinal axis so as to form a tube, the tube having a proximal open end and a distal open end, and being crimpable and expandable, and having a patterned shape in unexpanded form comprising; a first sinusoidal strut pattern comprising a series of repeated sinusoids defined by an apex section and a trough section, the repeated sinusoids coursing from the proximal open end to the distal open end of the tube; a second sinusoidal strut pattern comprising a series of repeated sinusoids defined by an apex section and a trough section, the sinusoids of the second sinusoidal strut pattern being in phase with respect to the apex and the troughs of the first sinusoidal strut pattern; wherein the second sinusoidal strut pattern is connected to the first sinusoidal strut pattern at at least two points, and wherein the connection at the points is from an apex of a sinusoid of the first sinusoidal pattern to an apex of a sinusoid of the second sinusoidal pattern.

In this embodiment, the first sinusoidal strut pattern and the second sinusoidal strut pattern are repeated multiple times, one after the other form the scaffold; the first sinusoidal strut pattern and the second sinusoidal strut pattern are the same or different. The scaffold is made of a biodegradable material, such as a polymer such as a poly-lactide polymer; and comprises a structure wherein the second sinusoidal strut pattern is connected to the first sinusoidal strut pattern at at least three or four points.

In an embodiment wherein the tubular-shaped structure is a stent, the stent comprises a plurality of sinusoidal-like or meandering strut patterns encompassing the diameter of the tubular structure, wherein each sinusoidal ring-like structure can be continuous with an adjacent sinusoidal ring-like structure at a point. Adjacent sinusoidal/meandering patterns can be continuous at at least one point. In one embodiment, the stent scaffold can be formed by two different types of meandering elements, the first meandering element comprises a zig-zag pattern/sinusoidal-like structure comprising with peaks and valleys which can extend the entire circumference of the scaffold, so that the meandering element can maintain a sinusoidal shape even when the scaffold structure is in its fully expanded configuration. A second type of meandering element also forms the stent scaffold, and can be intercalated or positioned in between adjacent first meandering elements, so that when the scaffold structure is fully deployed, the second type of meandering element forms a ring-like or hoop structure which can adapt to fully fit the diameter of a tubular organ space where the scaffold is deployed. The ring-like (also referred to as ringlet) element provides the tubular scaffold with increased hoop strength and can prevent collapsing of the scaffold once deployed. More specifically, this embodiment provides the ring, or hoop its expanded state, at least at one end of the tubular device for securing or anchoring the scaffold position in the organ space. In addition, another embodiment can provide at least one other ring or ringlet nestled within the scaffold so as to prevent dislocation of the scaffold from its implanted position. The embodiment can also provide a plurality of ringlets distributed randomly or in a regularly spaced pattern along the length of the scaffold. In the case of an expanded scaffold, the ringlets are designed to expand utmost into a ring or hoop shape or expand to a degree so as to retain some sinusoidal shape for more flexible, less rigid structural characteristics. The presence of secondary meandering struts both in the hoop shape at a scaffold end or anywhere along the scaffold axis, aids in preventing scaffold "creep" by tightly pushing against the wall of the organ space, as e.g. cardiovascularity. "Creep" in the present invention is defined as gradual dislocation of an implant from the original emplacement in the organ space. This change as caused by pulsating organ walls as well as bodily fluid flux, can be countered by re-crystallized hoop or ring entities that span the luminal space, press tightly against the surrounding tissue and yet exhibit enough elasticity and compatibility to reduce local injurious impact.

Embodiment devices may be comprised of a polymeric composition that is designed to be flexible in the unexpanded state and to be increasingly rigid and strong in proportion to its expansion. More specifically, the preferred embodiment is designed such that the end ring deriving from the secondary less meandering strut element would stretch to a hoop conformation at which the scaffold polymer acquires the strength necessary to resist compression for advantageous anchorage in the organ implant space. The basis for this differential scaffold strength is found in the polymer composition which shows an amorphous matrix in the relaxed or crimped configuration but upon cold straining, expanding, or stretching it induces a realignment of the polymeric matrix concomitant with an increased crystallization resulting in a proportionally enhanced scaffold mechanical strength.

In one embodiment, the tubular scaffold can comprise one or more than one of a second type of meandering elements and can be positioned in the tubular scaffold at alternating patterns between a first type of meandering elements to form a repeat pattern depending of the desired length of the tubular scaffold. In another embodiment, there is provided a scaffold configuration comprising meandering strut elements connected to an expansion-stabilizing ring-shaped portion and a snap-fit locking means operatively configured for securing the scaffold in a crimped position on a carrier device.

In one embodiment, a tubular scaffold can be provided in a crimpable and expandable structure for use in conjunction with balloon angioplasty. Such tubular embodiment optionally may comprise a securing mechanism, which can be positioned at or near the ends of the tubular structure/scaffold. In this embodiment, the securing mechanism can be of different designs and structurally configured to secure the flexible plastic scaffold onto a carrier portion of the delivery system, and wherein the scaffold can be crimped down in a locked position so as to keep the scaffold immobilized on the carrier for vascular implantation. The securing mechanism may comprise, for example, mechanical locking means, such as snaps, hooks, lock- and key-like structures, mating structures and abutting structures, and the like, which can engage one another and secure the scaffold on the carrier in a tightly crimped configuration. The securing mechanism can prevent dislodging of the scaffold during deployment or transport on a carrier for implantation. For example, the locking means may be structurally configured to operate, for example, as a snap-fit locking means and can be positioned at or near one end, or at or near both ends of the scaffold. The snap-fit locking means may be in the form of a finger-like extension to slide over an adjacent similarly curved scaffold portion positioned in or near the end portion of the tube-like configuration. In one embodiment of the scaffold that is lockable in the crimped down transport position includes a snap-fit key-in-lock design similar to a dovetail slotting structure.

In another embodiment, the scaffold can be lockable in the crimped down transport position, by securing means including, a snap-fit, key-in-lock design similar to a ball and socket-like joint structure. In another embodiment, there is provided a snap-fit, key-in-lock configuration wherein a series of hook-like strut extensions on a meandering ring structure can interlock with an adjacent oppositely arranged hook-like strut. In other embodiments, the locking mechanism may comprise friction enhancing components and other slide interfering properties may be used to lock in the crimped scaffolding. Thus, in this embodiment, the mechanical interlocking features of the crimped scaffold may be enhanced by frictional properties incorporated in the plastic composition. These frictionally enhancing properties may be added to the composition itself or grafted in the form of a layer or in isolated or stippled surface components. Suitable agents include ionic or non-ionic substances. Nonionic interactions or weak force attractions play a role enhancing the frictional component of the scaffold. Ionic additives are preferably concentrated on the locking surfaces of the crimped scaffold in soluble form so as to avoid unwanted plasma protein reactions.

In certain embodiments, the locking means of a deployed scaffold can be disengaged by the expanding means of the delivery carrier. Depending on their location, the locking features of the scaffold can be selected to unlock for expansion at different rates from a narrowly crimped delivery conformation of the entire scaffold structure to a lumen diameter sufficient for implantation onto the vascular wall. In one embodiment, the scaffold can be manipulated to vary from a uniform cylindrical to a more conal shape structure allowing for easy of implant installation, relocation and adjustment. For example, the scaffold implant may in a configuration comprise a balloon type reversible inflation or dilation means which carries the locked scaffold configuration into the body and deposits the same in the target area by expanding the crimp-locked scaffold so as to break the locked-in position and stretching the holding ring to a hoop-like form and firmly engage the lumen perimeter. The balloon inflating means comprises a means for heating and/or cooling the device.

A medical device embodiment, such as a stent, may be manufactured from polymeric materials which comprises a polymer having breakdown moieties that are "friendly" at contact with bodily tissues and fluids such as the vascular wall. In a specific embodiment, the medical device comprises a polymer with breakdown kinetics sufficiently slow to avoid tissue overload or inflammatory reactions which can lead to restenosis, for example, which provides a minimum of 30-day retention of clinically supportive strength. In one embodiment the medical device may be endured in place as much as 3-4 months post-implantation without undergoing substantial bioabsorption.

In one embodiment, the implant can undergo transitional change after implantation, from a solid flexible implant at implantation, to a "rubbery state" post-implantation which exhibits flexibility, yet enough resilience and cohesion so as to permit surgical intervention.

In one embodiment, the polymer selected for making the device has flexibility and elasticity suitable for an implant in friction-free contact with vascular walls during the cardiovascular pulsing contractions and relaxations. In an embodiment, the medical device comprises a stretchable and elastic scaffold, which has a sufficiently rigid strength to be capable of withstanding the fluctuating cardiovascular pressures within a blood vessel. For example, the polymer selection can be based on evaluation criteria based on mass loss in terms of decreased molecular weight, retention of mechanical properties, and tissue reaction.

In an embodiment, the implant is manufactured of a bioabsorbable polymer wherein the molecular moieties of the bioabsorbable polymer is composed of a poly L-lactide or a poly D-lactide as the base polymer, wherein modifying copolymers include poly L(or D)-lactide-co-tri-methylene-carbonate or poly L(or D)-lactide-co-e-caprolactone are used to link the base polymers. These copolymers can be synthesized as block copolymers or as "blocky" random copolymers wherein the lactide chain length is sufficiently long enough to crystallize.

In another embodiment, the composition comprises a base copolymer wherein one moiety is sufficiently long enough and not sterically hindered to crystallize, such as L-lactide or D-lactide with a lesser moiety, for example Glycolide or Polyethylene Glycol (PEG) or monomethoxy-terminated PEG (PEG-MME).

In another embodiment, the compositions in addition to the base polymer, the modifying polymer or co-polymer may also have enhanced degradation kinetics such as with an ε-caprolactone copolymer moiety where the ε-caprolactone remains amorphous with resulting segments more susceptible to hydrolysis.

In another embodiment, the composition can incorporate polyethylene glycol (PEG) copolymers, for example either AB diblock or ABA triblock with the PEG moiety being approximately 1%. In this embodiment, the mechanical properties of the Lactide (see Enderlie and Buchholz SFB May 2006) are maintained. In this embodiment the incorporation of either PEG or PEG-MME copolymers may also be used to facilitate drug attachment to the polymer, for example in conjunction with a drug eluding medical device.

In another embodiment, the medical device comprises a polymeric scaffold comprising a base polymer comprising a combination of polymers of low PEG content of less than 5% in high MW, i.e. 2-3 IV copolymers, which enables the lactide block to crystallize and impart equivalent strength to the base polymer.

In an embodiment, the polymer composition allows polymer realignment and the development of a crystalline morphology. Plastic deformation imparts crystallinity to polymer molecules. A polymer in crystalline state is stronger than its amorphous counterpart. In stent embodiments comprising ring-like structures, the ring-like structures or ringlet may be a material state that is inherently stronger than that of a sinusoidal stent segment. that can enhance the mechanical properties of the medical device, enhance processing conditions, and provide potential of cross-moiety crystallization, for example, thermal cross-links.

Further embodiments disclosed herein include shortening the degradation time of the polymer in the composition, for example, a medical device comprises a bioabsorbable polymer with enhance degradation kinetics. In this embodiment the starting material can be a lower molecular weight composition and/or a base polymer that is more hydrophilic or liable to hydrolytic chain scission can be employed.

In another device embodiment, the medical device comprises a polymer blend comprising a marker molecule, for example, radio-opaque substance, a fluorescent substance or a luminescent substance, which can serve to detect or identify the medical device once implanted into a patient. For example, compounds that can be used as marker molecules include, iodine, phosphorous, fluorophores, and the like. A medical device such as one employing fluoroscopy, X-rays, MRI, CT technology and the like may be used to detect the radioopaque substance.

In this and other embodiments of the invention, the medical device can comprise fillers and one or more pharmaceutical substances for local delivery. The medical device may, for example, comprise, a biological agent, a pharmaceutical agent, e.g. an encapsulated drug (which may be used for localized delivery and treatment—for example, of vascular wall tissue and lumen).

In another embodiment, there is provided a scaffold structure comprising a core degradation schedule which provides more specifically a simultaneously slow release of medication for the treatment and prevention of tissue inflammation and platelet aggregation. The polymer composition or blend provides uniform degradation in situ avoiding polymer release in large chunks or particles.

In another embodiment, the polymer compositions are used to manufacture medical device for implantation into a patient. The medical devices comprise scaffolds having biodegradable, bioabsorbable and nontoxic properties and include, but are not limited to stents, stent grafts, vascular synthetic grafts, catheters, vascular shunts, valves and the like. Biocompatible and bioabsorbable scaffolds may be particularly found useful in treatment of coronary arteries. For example, a scaffold structure may be manufactured or extruded from a composition comprising a base polymer material, at least one drug for local delivery and at least one attached or embedded identification marker.

In another embodiment, a method for treating vascular disease is disclosed, the method comprising, administering to a person suffering with vascular disease a medical scaffold or device comprising a structure made from a biocompatible, bioabsorbable polymer.

BRIEF DESCRIPTION OF THE DRAWINGS

The figures provided herewith depict embodiments that are described as illustrative examples that are not deemed in any way as limiting the present invention.

FIG. 4A also shows the nested hoop/rings structures.

FIG. 7A illustrates the amorphous state of the polymer composition for making the devices. FIG. 7B illustrates the polymer fibers alignment in a partially expanded configuration and FIG. 7C illustrates the crystalline state of the fibers upon expansion of a bioabsorbable stent embodiment.

FIG. 10A illustrates the connection elements of a bioabsorbable scaffold as described in FIG. 9A showing the state of the connections as manufacture; FIGS. 10B and 10C in a partially expanded state and FIG. 10D in a fully expanded state.

DETAILED DESCRIPTION

Figure 1:
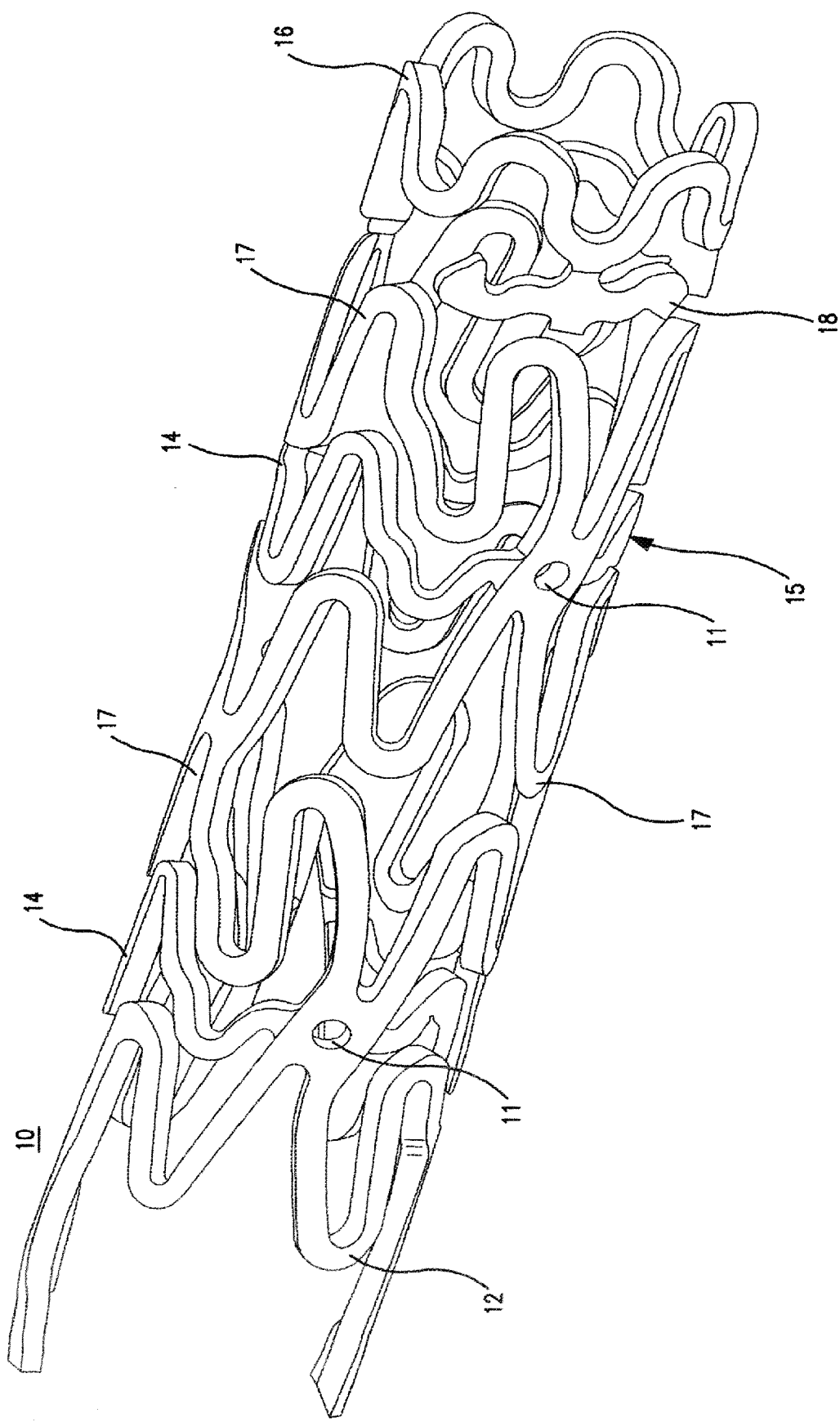
FIG. 1 is a computer simulation illustration depicting a partial view of an embodiment of a bioabsorbable medical device depicting a scaffold strut segments, nested hoop structures, end ring, locking mechanism and interconnection "H" regions.

Disclosed herein are novel structure elements, and novel compostions which may be used to make such novel structural elements. The present embodiments may find use in the treatment of many diseases and physiological ailments.

In recent years, metallic stents have come into use to aid in the clearing the clogged lumen of the vascular system. However, the efficacy of metallic stent implants in vascular arteries has been diminished by certain disadvantageous results. For example, since such stents have shown a tendency to stimulate formation of scar tissue or restenosis in the wound inflicted in the vascular area of deployment. This effect becomes more detrimental in the use of small diameter tubes in therapy. Moreover, it is important to avoid arterial wall damage during stent insertion. These factors (although somewhat difficult to control in the first instance) are aimed at trying to reduce the mechanical reasons that lead to excessive clot and scar formation within the vessel lumen.

Stent structures typically comprise a number of meandering patterns. By "meandering" it is meant moving along a path that is other than strictly linear. Due to the need to have an unexpanded form to allow for easy insertion of a stent into its biological milieu, such as, without limitation, the vasculature, the meandering patterns making up a stent are often sinusoidal in nature, that is having a repeating sequence of peaks and troughs. Often such sinusoidal structures are normalized such that each peak or trough is generally of the same distance as measured from a median line. By "non-sinusoidal" it is meant a pattern not having a repeating sequence of peaks and valleys, and not having a series of raised portions of generally the same distance as measured from a median line nor a series of depressed portions of generally the same distance as measured from a median line. A stent may be characterized as having three distinct configurations, an unexpanded state (as manufactured), a crimped state (a compressed state as compared to the unexpanded state), and an expanded state (as deployed as an implant in vivo).

While the configurations disclosed herein are not limited to fabrication by any particular material, in certain embodiments such configurations are constructed from a flexible, elastic, and bioabsorbable plastic scaffold. In embodiments disclosed herein, there is illustrated a bioabsorbable and expandable scaffold of various shapes, patterns, and details fabricated from bioabsorbable polymers and polymer compositions. The scaffolds in an advantageous embodiment balance the properties of elasticity, rigidity and flexibility while being more biocompatible, less thrombogenic and immunogenic than prior art polymeric medical devices. Such embodiments may provide means for preventing device creep or repositioning when crimpedly placed on a carrier as well as when expandedly placed in a living organ space. Stent implants may employ a balloon expandable medical device which comprises a thermal balloon or non-thermal balloon.

Now turning to the figures, FIG. 1 is a computer simulation illustration depicting a partial view of an embodiment of a bioabsorbable medical device in unexpanded form depicting scaffold strut segments 17, nested hoop structures 14 and end rings 16, both comprising structures not in the same plane, locking mechanism 18 connected to another locking mechanism (not shown) and interconnection "H" regions 15 having an ring expansion through-hole 11 at the nested hoop structures 14.

Figure 2:
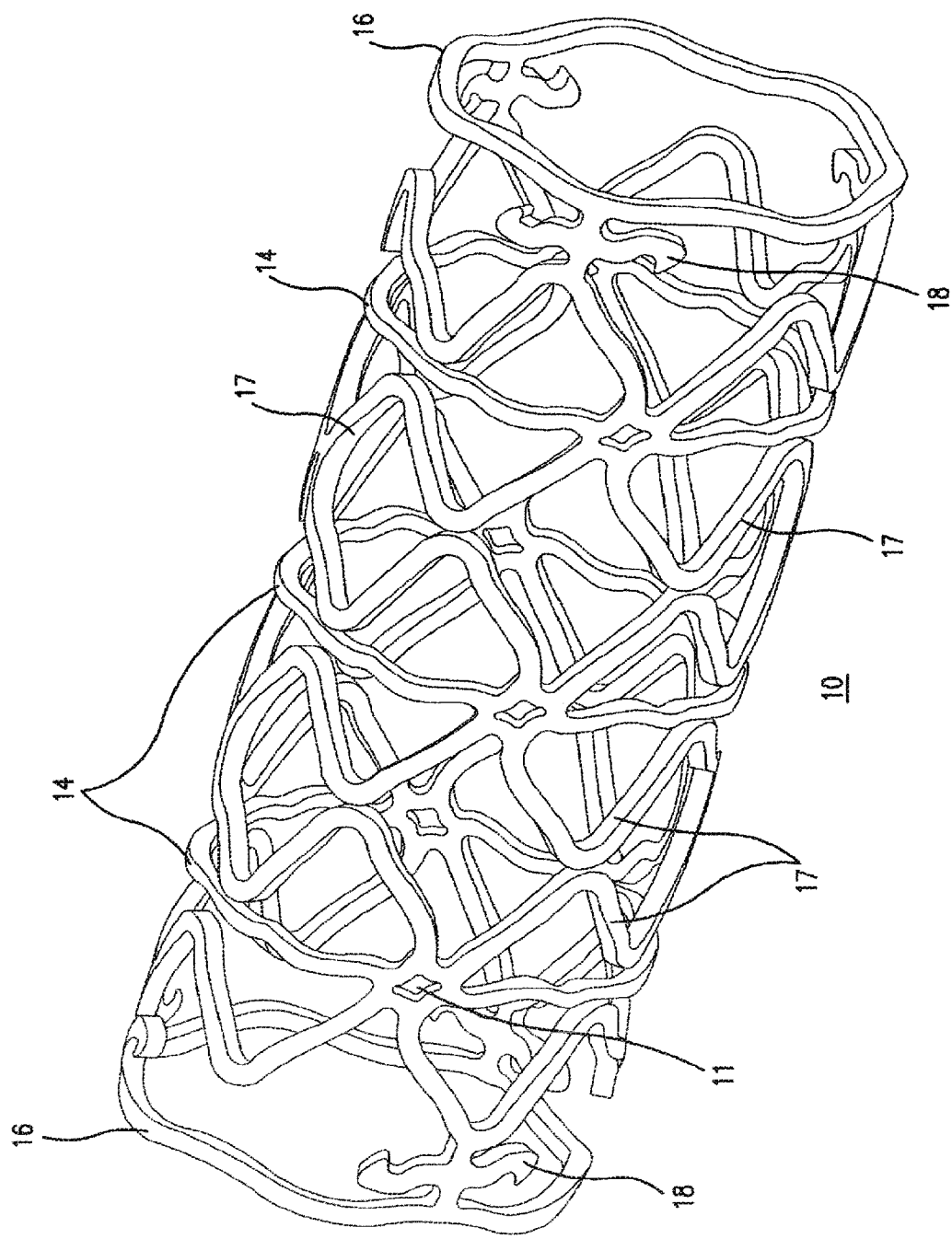
FIG. 2 is a computer generated illustration of an embodiment comprising a bioabsorbable stent design in a somewhat expanded configuration showing the nested hoop or ring structures, end ring, meandering strut pattern and locking mechanism.

FIG. 2 is a computer generated illustration of an embodiment comprising a bioabsorbable stent design in a nearly expanded configuration showing the nested hoop structures 14 (or ring structures) and end rings 16 now in generally in the same plane, meandering strut pattern 17 and locking mechanism 18 detached from another locking mechansim. Expansion through-hole 11 as shown has been stretched into an oblong hole in such expanded configuration.

Figure 3A:
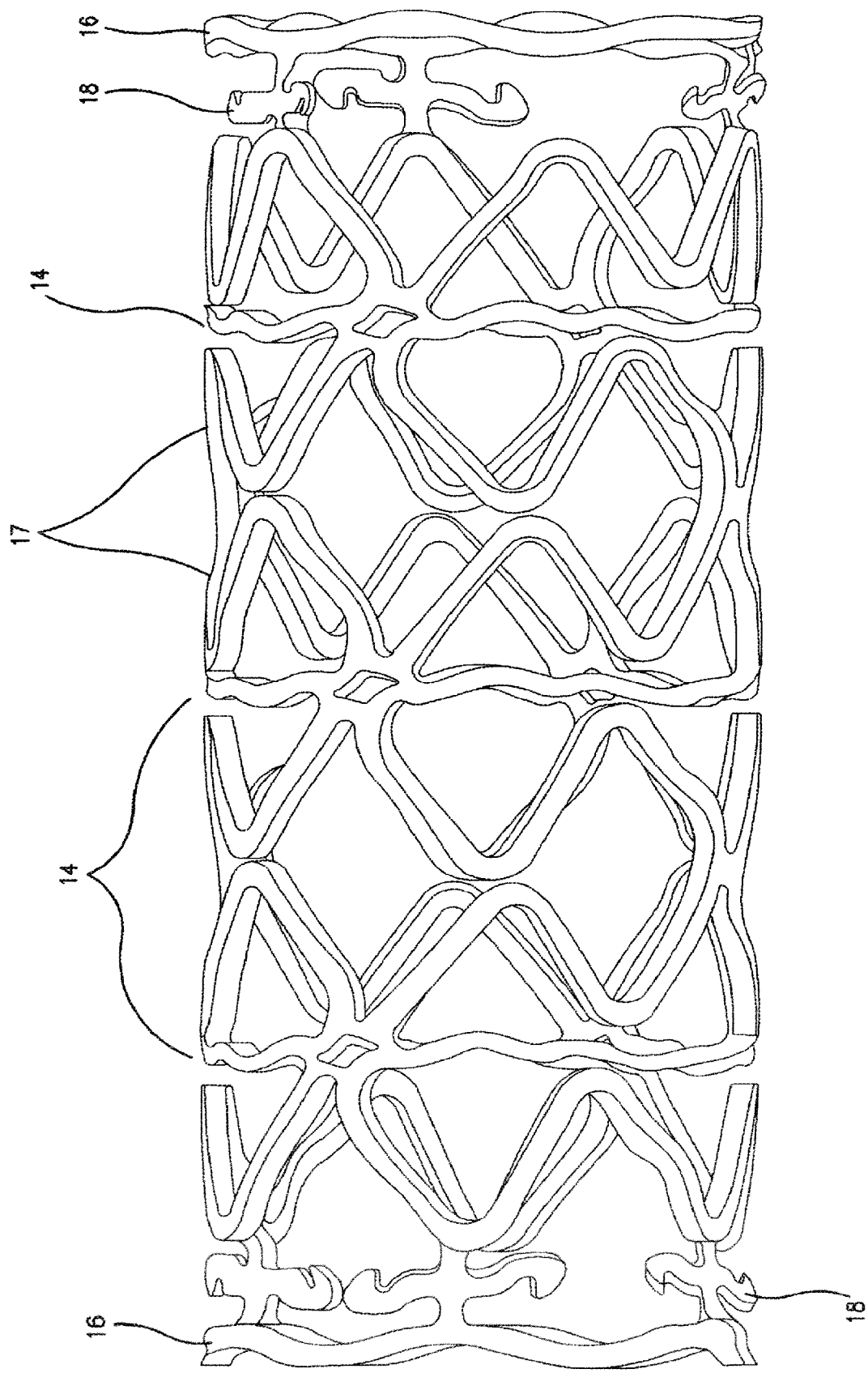
FIG. 3A depicts a computer simulation illustrating a prematurely expanded bioabsorbable stent scaffold showing an alternating ring or hoop structures with a meandering strut element pattern and locking mechanism.
Figure 3B:
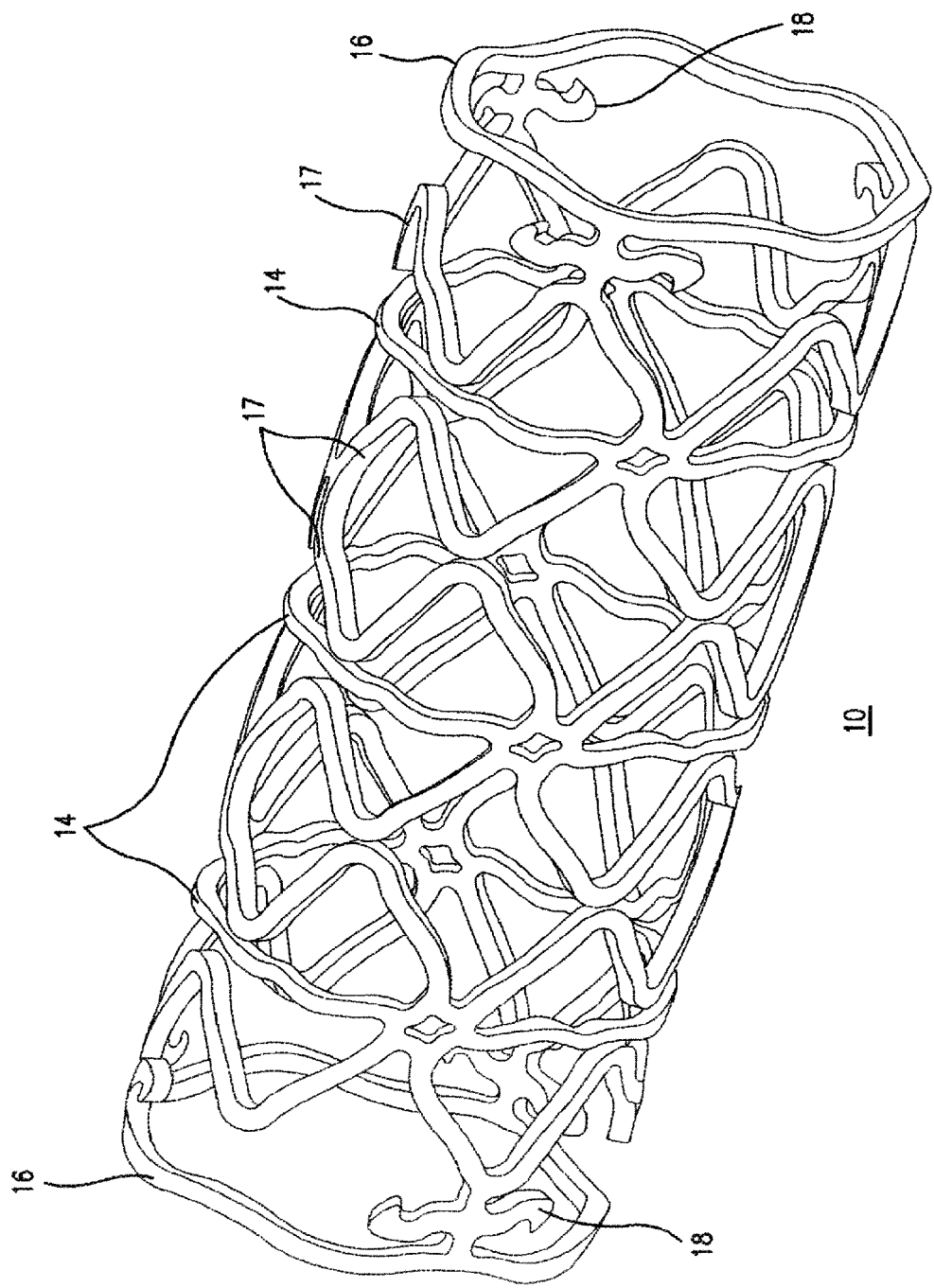
FIG. 3B is the same stent scaffold as in FIG. 3A showing a ring segment in different states of stress.

FIG. 3A depicts a computer simulation illustrating a prematurely expanded bioabsorbable stent scaffold showing an alternating ring or hoop structures with a meandering strut element pattern 17 and locking mechanism 18. FIG. 3B is the same stent scaffold as in FIG. 3A showing a ring segment in a different state of stress. In either case, the structure comprising each ring or hoop is generally in the same plane.

Figure 4A:
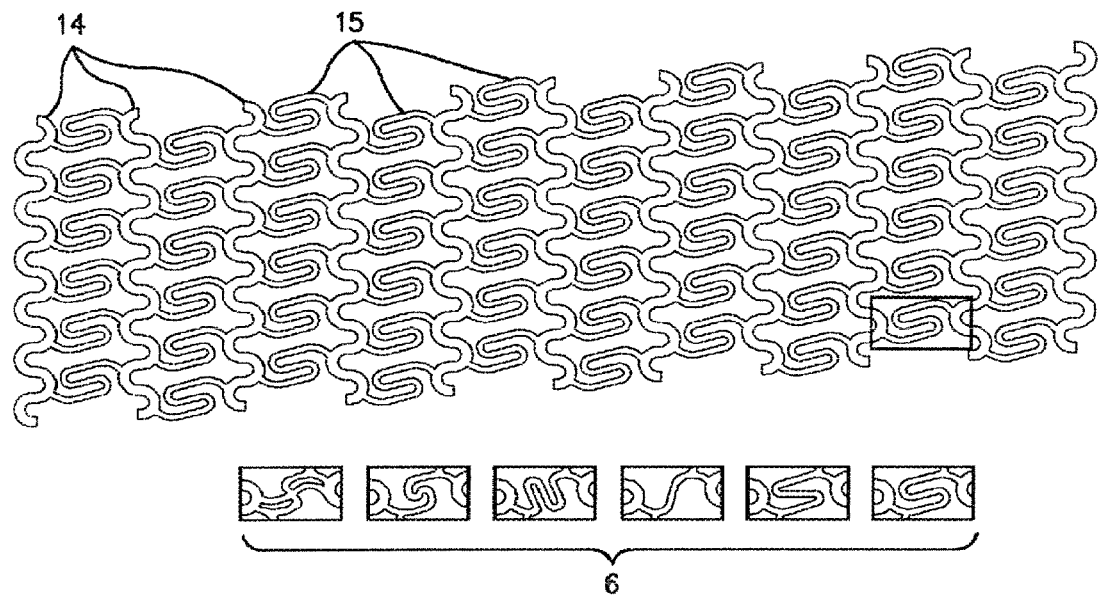
FIG. 4A illustrates is a planar view of an embodiment showing a bioabsorbable stent scaffold pattern which depicts a planar view of a bioabsorbable scaffold featuring repetitive strut pattern in the shape of an S which can be replaced with other designs as shown.
Figure 4B:
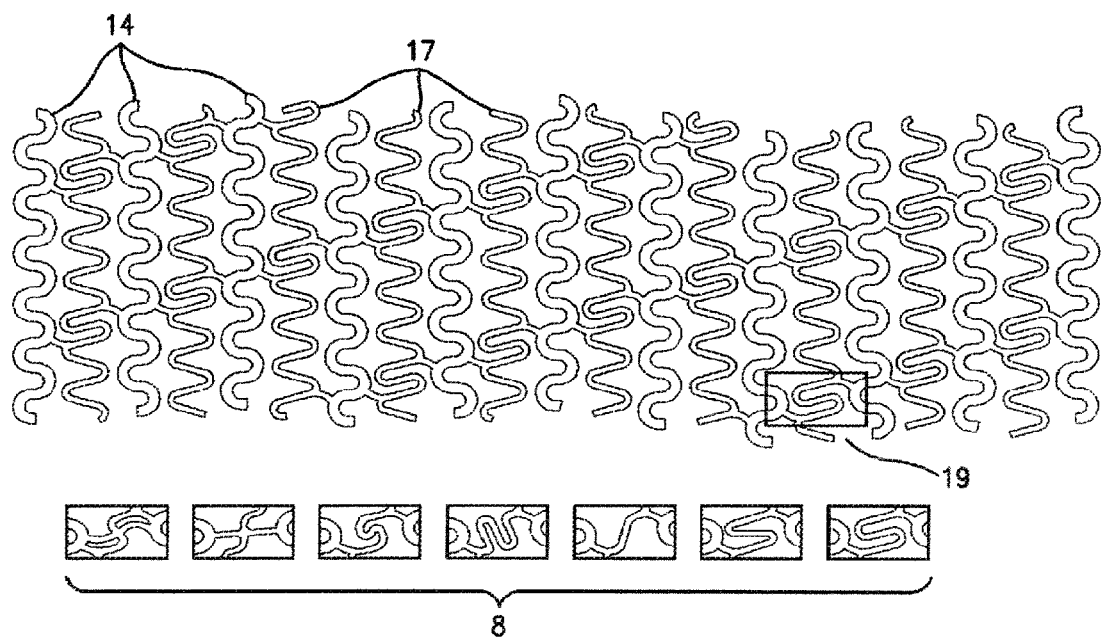
FIG. 4B is an alternate embodiment in a planar configuration which illustrates the nested ring features, wherein the stent strut structure can be replaced with the design encompassed at 8.
Figure 4C:
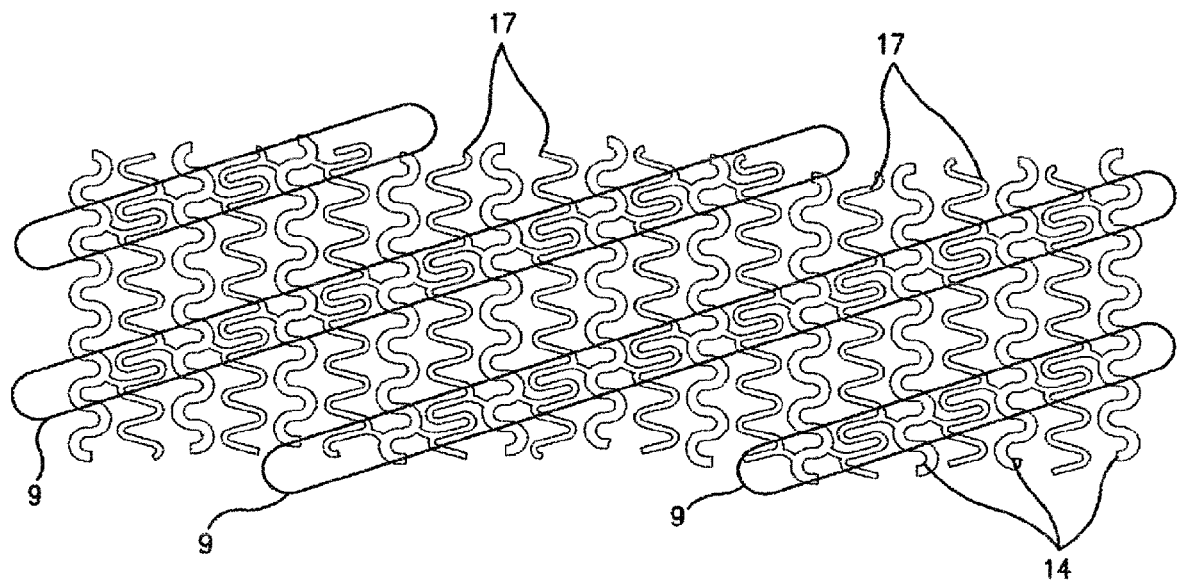
FIG. 4C is a planar view illustration of an embodiment of the invention in which the structural pattern forms helical structures.
Figure 4D:
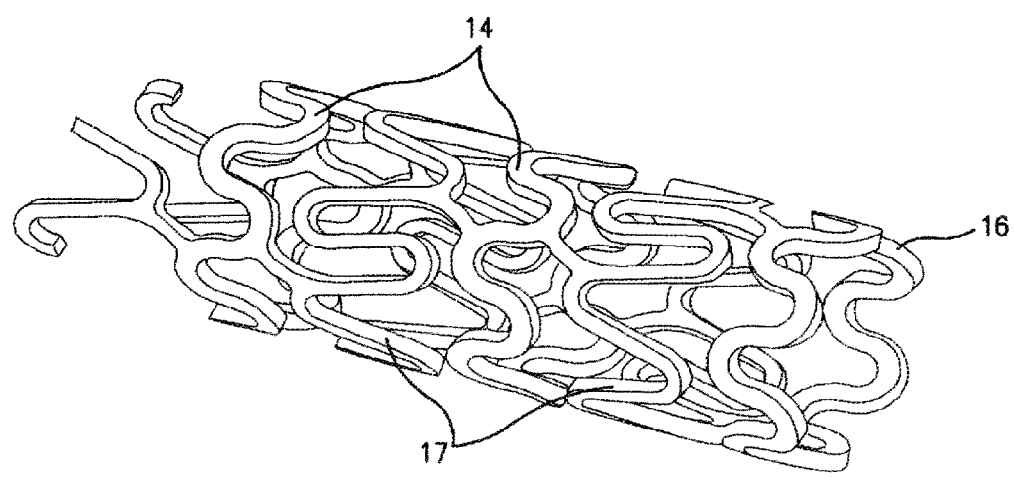
FIG. 4D illustrates a partial stent structure with hoop or ring structural elements and scaffolding elements in the form as manufactured.
Figure 4E:
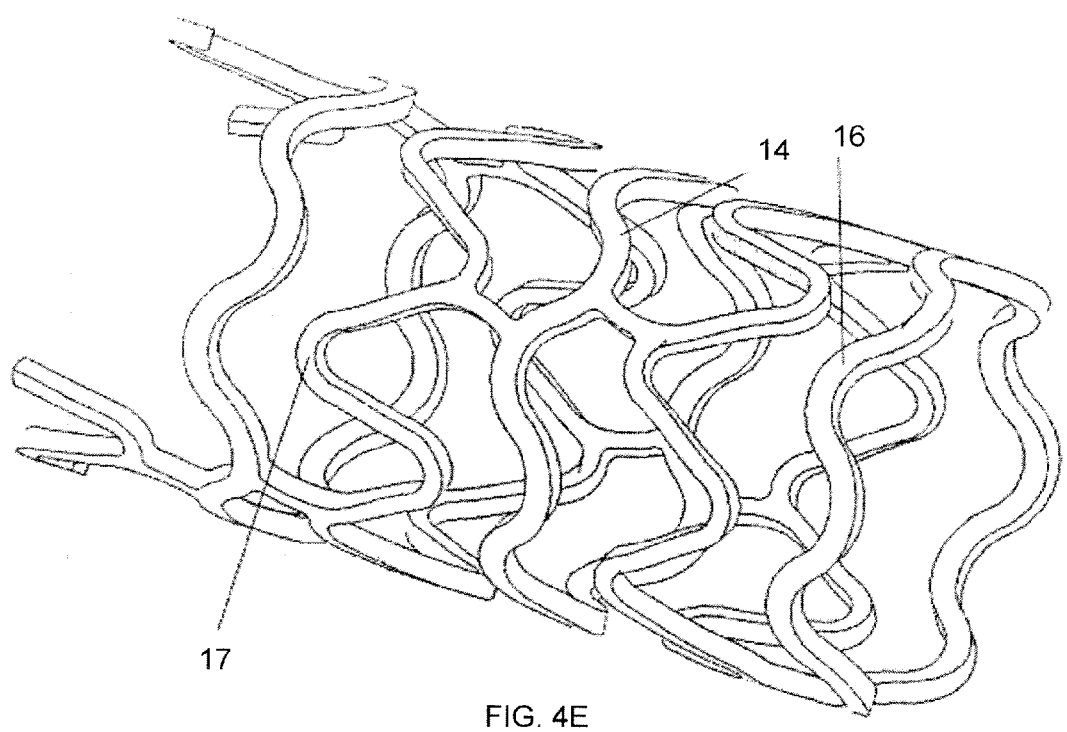
FIG. 4E illustrates the stent structure of FIG. 4D in a partially expanded configuration.
Figure 4F:
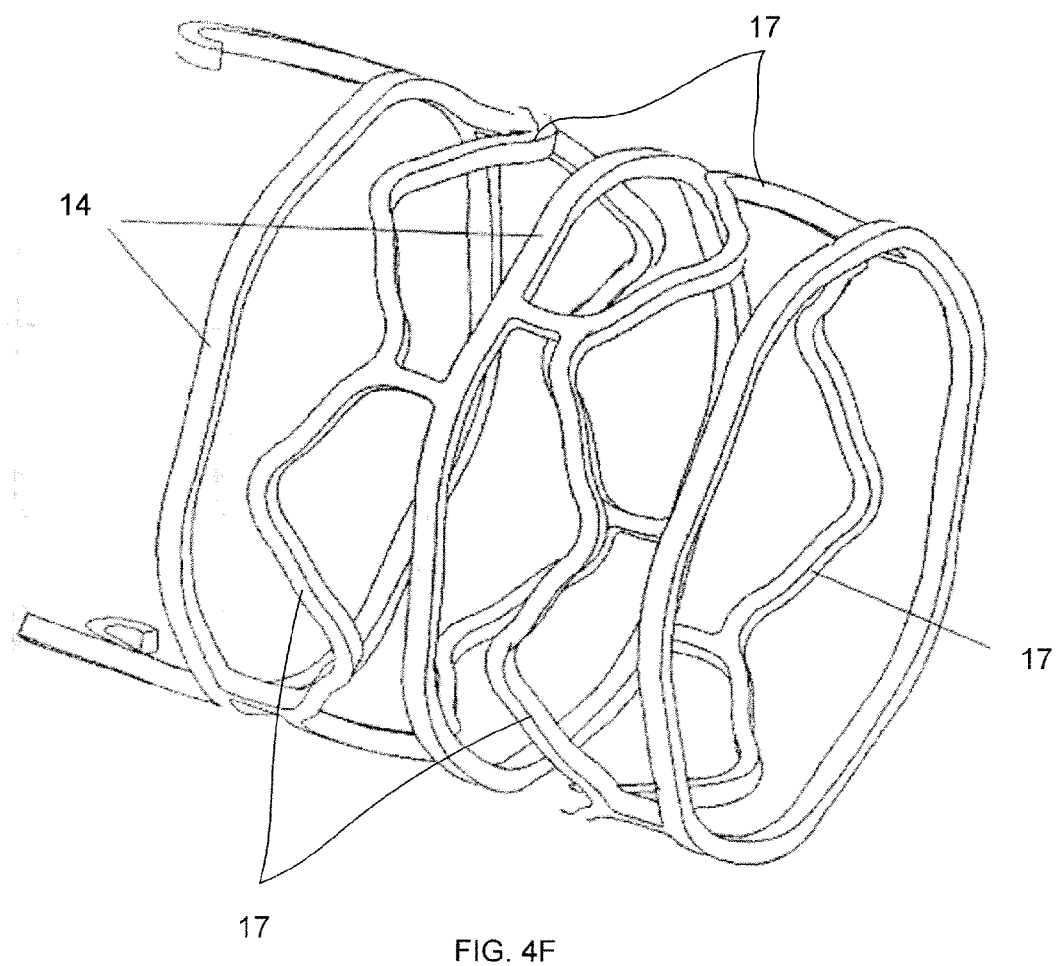
FIG. 4F illustrates the stent structure of FIG. 4D in an expanded configuration.

FIG. 4A illustrates is a planar view of an embodiment showing a stent scaffold pattern 15, which may be bioabsorbable, in the shape of an S which can be replaced with other designs as shown. FIG. 4A also shows the nested hoop/rings structures 14. FIG. 4B is an alternate embodiment in a planar configuration which illustrates the nested ring features 14, wherein the stent strut structure can be replaced with any of the design encompassed at 8. FIG. 4C is a planar view illustration of an unexpanded scaffold embodiment of the invention in which the structural sinuosiodal pattern 17 forms helical patterned structures 9 in the overall structure (shown as diagonal patterns in the planar view). FIG. 4D illustrates a partial unexpanded stent structure 16 formed of the scaffold of FIG. 4C with hoop or ring structural elements 14 and scaffolding elements in the form as manufactured. FIG. 4E illustrates the stent structure of FIG. 4D in a partially expanded configuration. FIG. 4E illustrates the stent structure of FIG. 4D in an expanded configuration with reach ring as a item in substantially the same plane.

Figure 5:
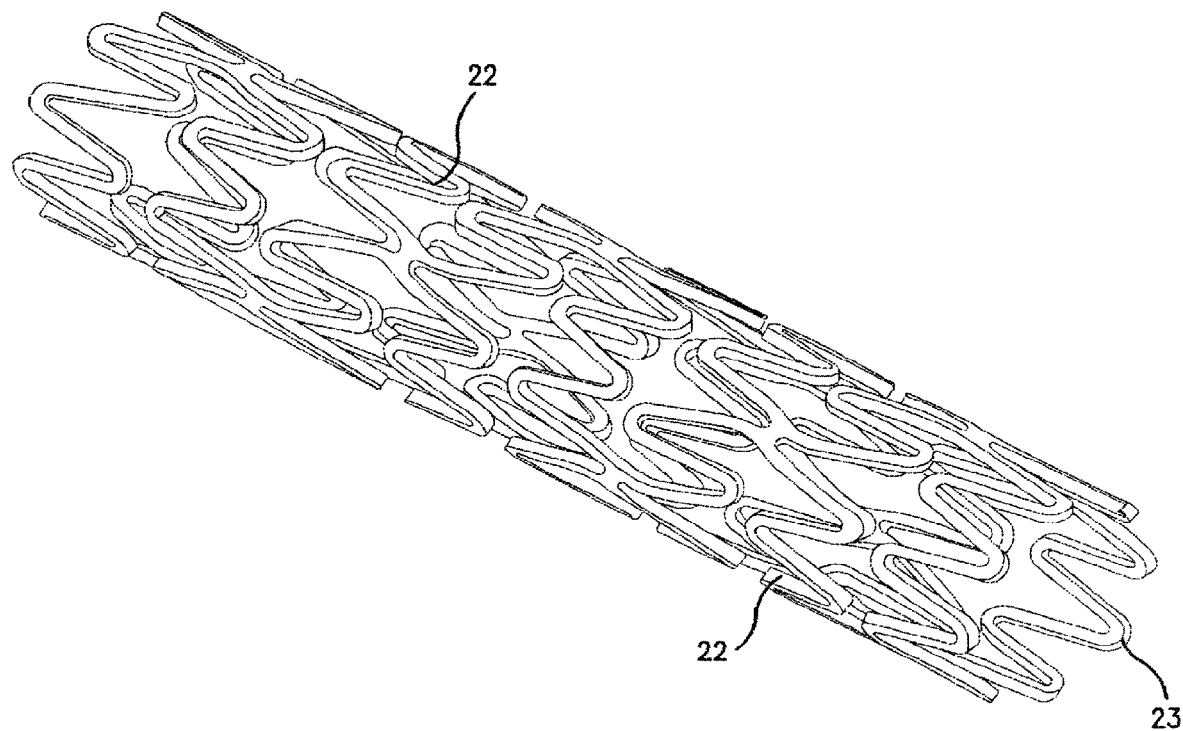
FIG. 5 depicts an oblique view of a bioabsorbable stent embodiment exhibiting meandering strut segments in a sinusoidal pattern.

FIG. 5 depicts an oblique view of an unexpanded bioabsorbable stent embodiment exhibiting meandering strut segments 22 in a sinusoidal pattern and end ring 23.

Figure 6A:
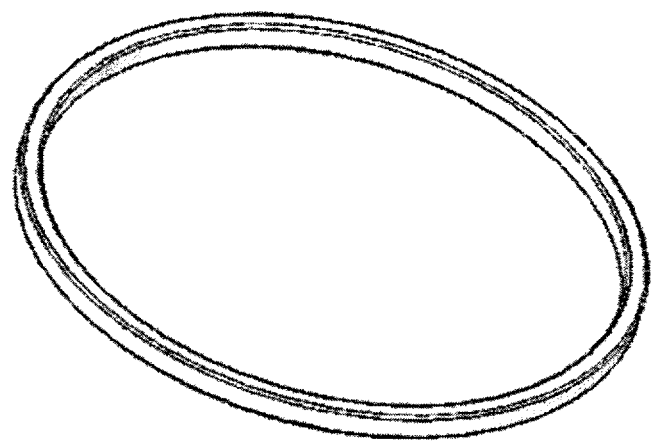
FIG. 6A depicts a partial top view of expanded hoop or ring and meandering or sinusoidal (6B) bioabsorbable strut elements of a stent embodiment.
Figure 6B:
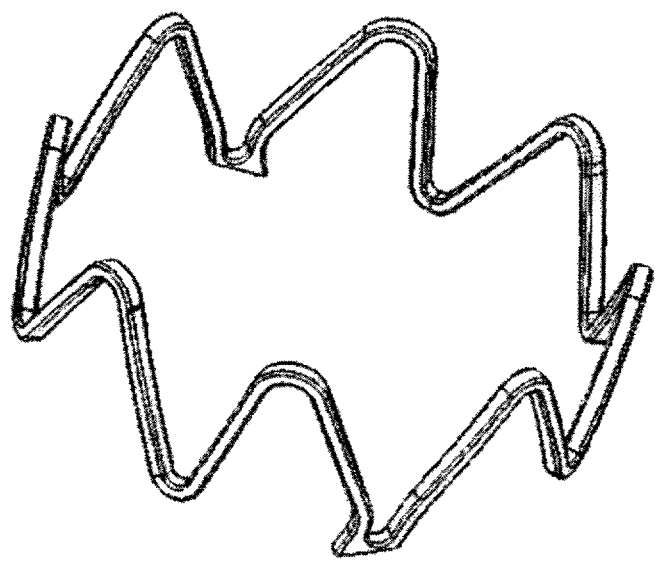
FIG. 6C illustrates a hoop or ring element of a bioabsorbable stent showing how radial/transverse load is distributed through a ring structure.
Figure 6C:
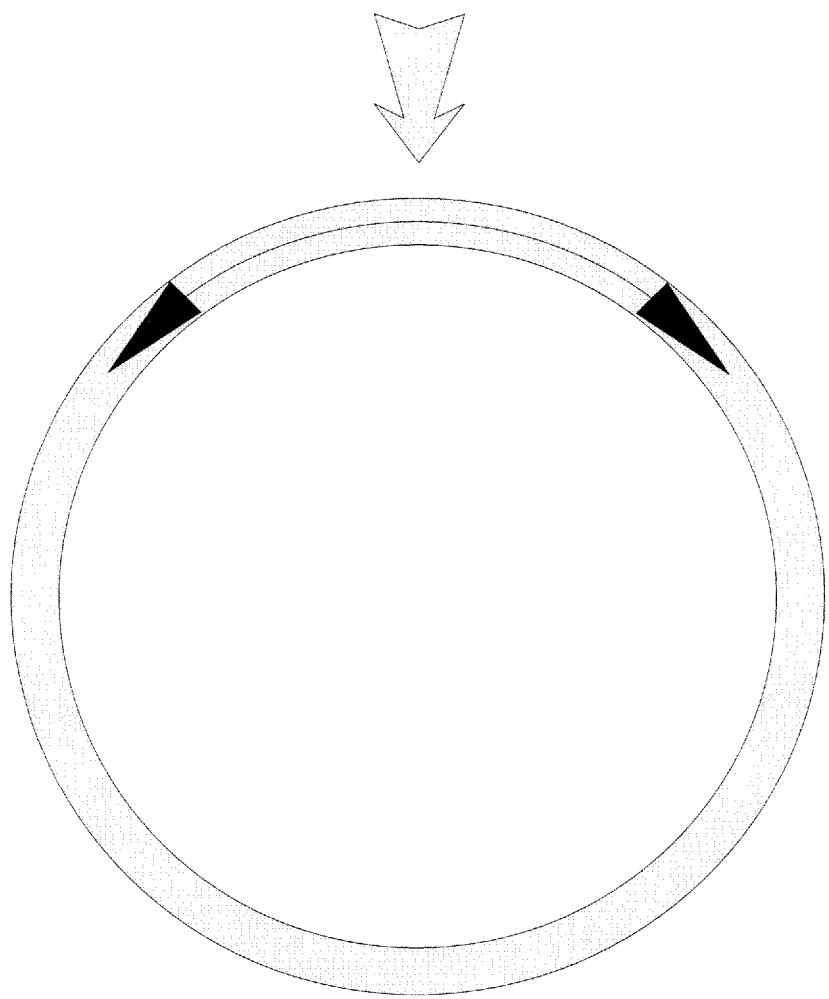

FIG. 6A depicts a partial top view of an expanded hoop or ring, while FIG. 6B illustrates such hoop or ring when not expanded, shown in the drawing as composed of meandering sinusoidal (6B) bioabsorbable strut elements of a stent embodiment. FIG. 6C illustrates a hoop or ring element of a bioabsorbable stent showing how radial/transverse load is distributed through a ring structure. As illustrated such structure provides a better distribution of forces keeping such stent open under forces that might otherwise cause deformation of the stent.

Figure 7A:
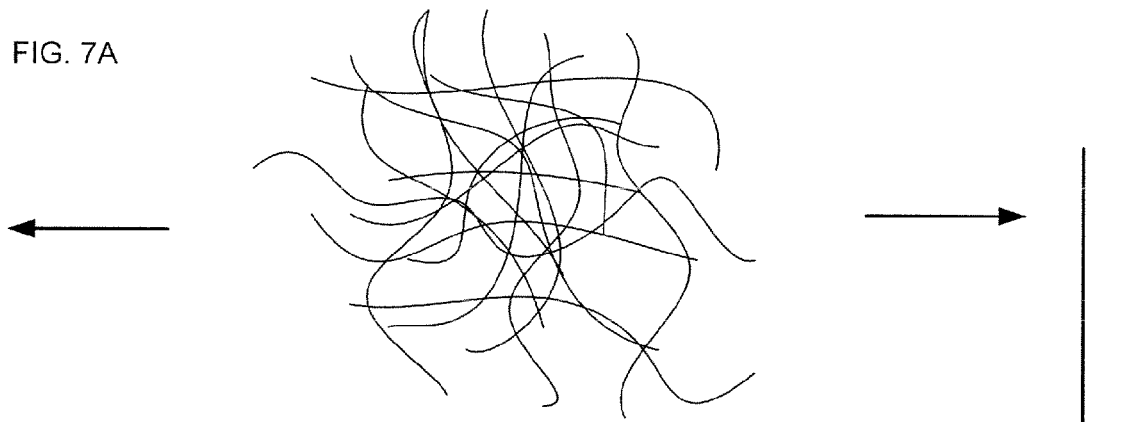
FIG. 7A-7C illustrates the polymer fibers alignment in embodiments of the bioabsorbable medical devices and how the alignment undergoes plastic deformation upon stress.
Figure 7B:
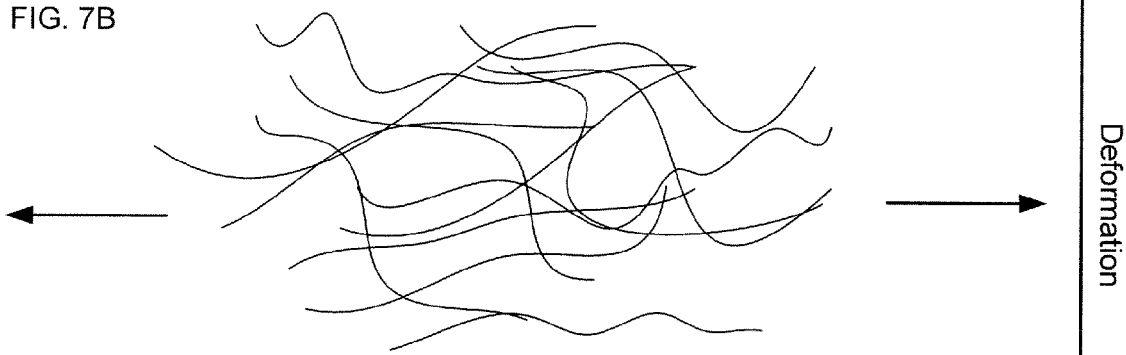
Figure 7C:
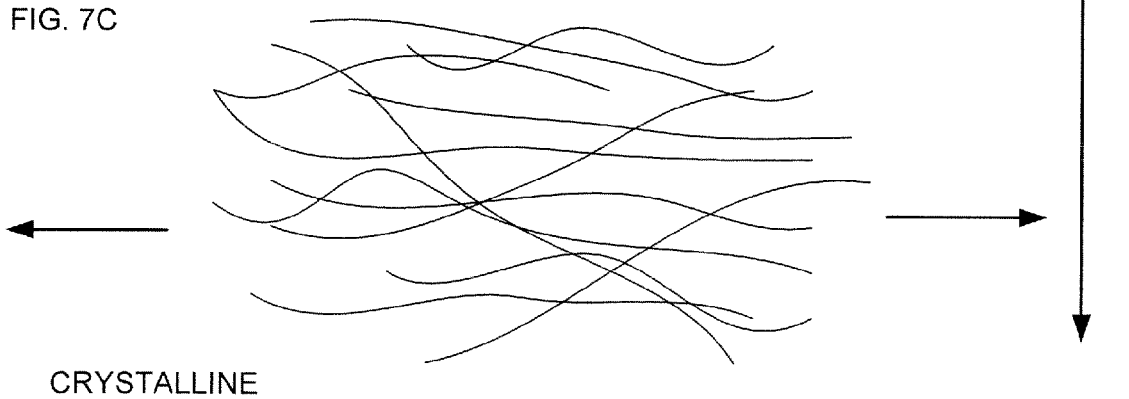

FIG. 7A-7C illustrates the polymer fibers alignment in embodiments of the bioabsorbable medical devices and how the alignment undergoes plastic deformation upon stress. FIG. 7A illustrates the amorphous state of the polymer composition for making the devices. FIG. 7B illustrates the polymer fibers alignment in a partially expanded configuration and FIG. 7C illustrates the crystalline state of the fibers upon expansion of a bioabsorbable stent embodiment composed of racemate or stereocomplex polymeric compositions.

Figure 8A:
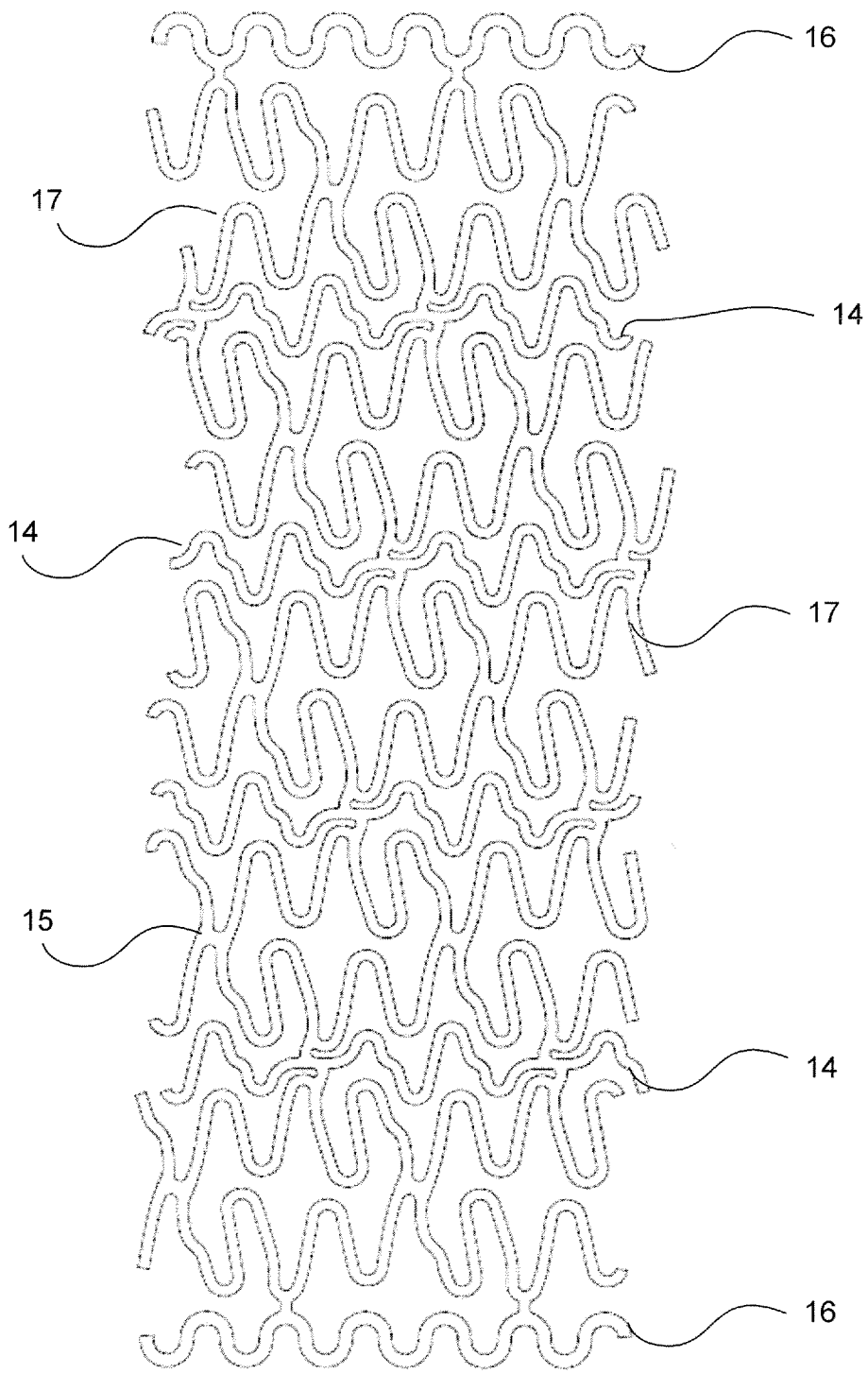
FIG. 8A illustrates a planar view of a bioabsorbable stent scaffold embodiment comprising, structural meandering strut elements, nested hoop/ring elements and having end rings at the openings of the stent tube.
Figure 8B:
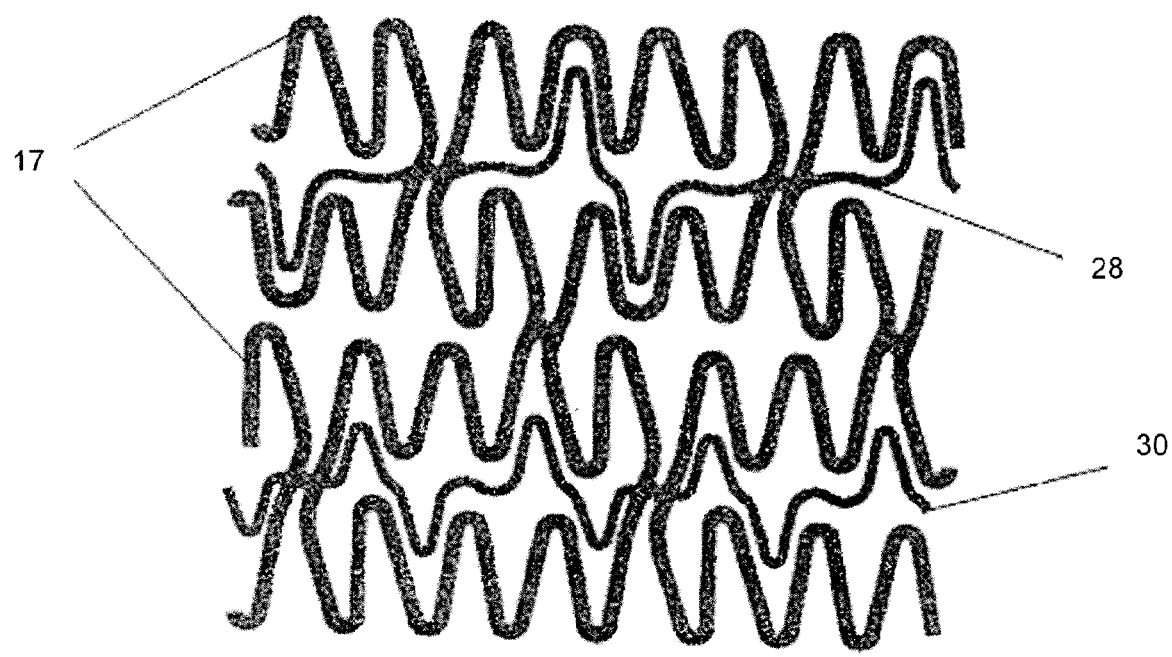
FIG. 8B is a planar view of a section of the stent scaffold of FIG. 8A illustrating the structural meandering strut elements, nested hoop/ring elements and connection structures which form the stent scaffold. The stent scaffold is shown in a state as manufacture and also shows the nested rings structures in various configurations and connections between structural meandering elements and hoop elements in the shape of a stylized letter H configuration.
Figure 8C:
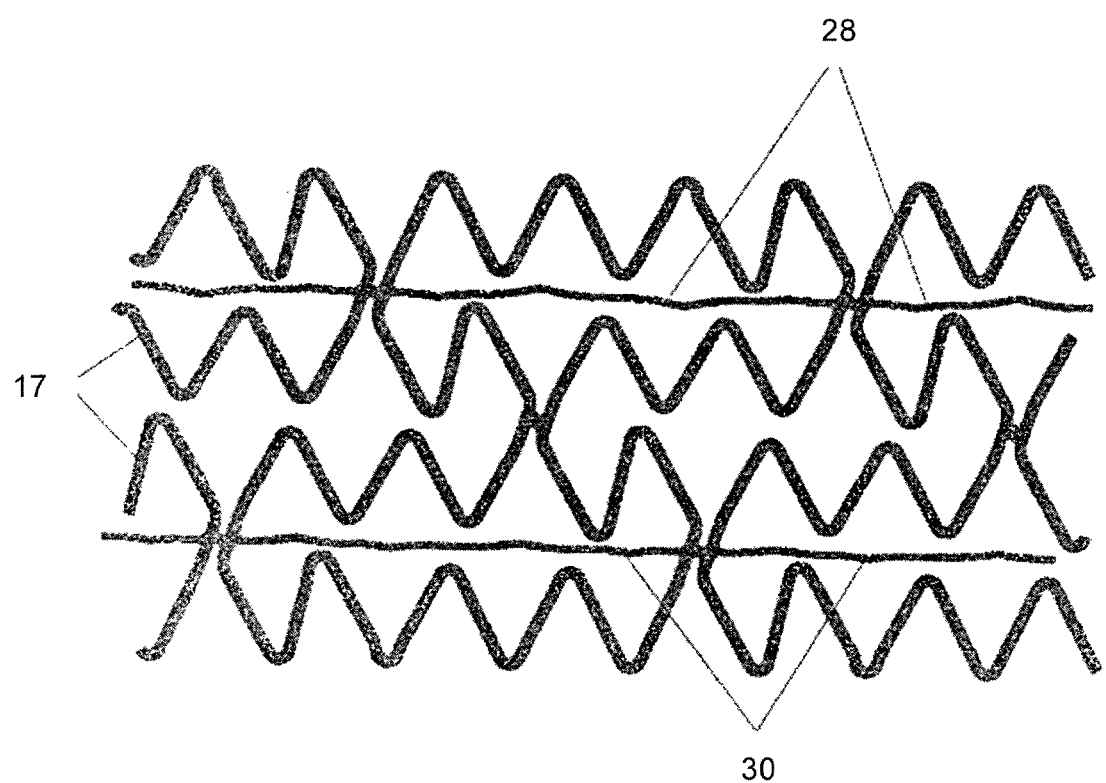
FIG. 8C illustrates the segment of FIG. 8B in an expanded configuration.
Figure 8D:
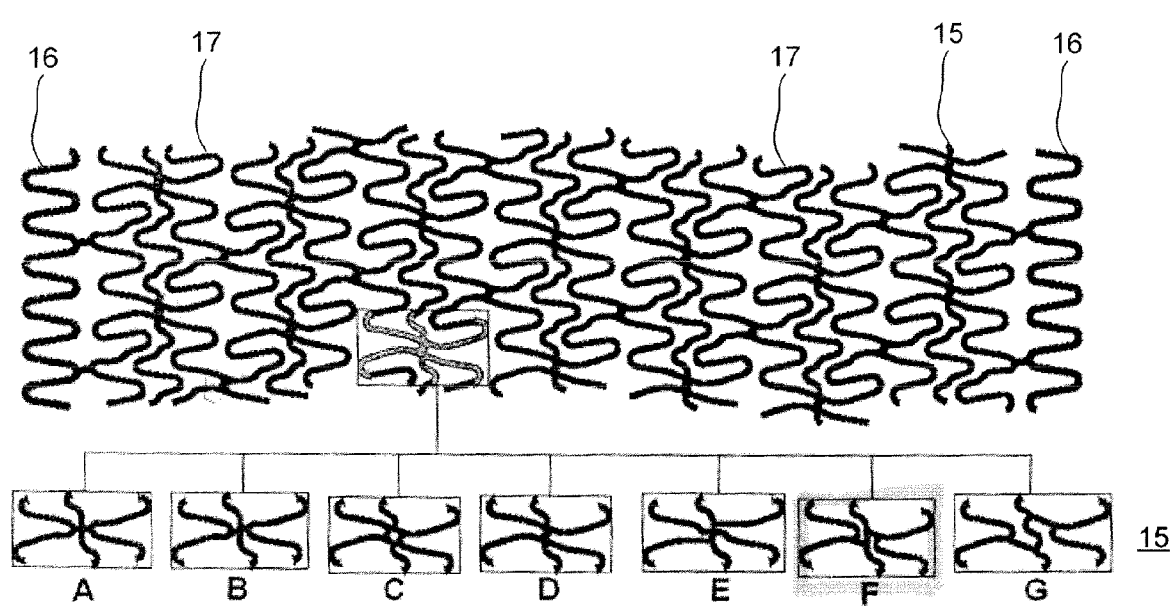
FIGS. 8D, 8E and 8F are planar views of bioabsorbable stent scaffold walls showing alternate design embodiments of the connection elements which can be substituted between meandering strut elements.
Figure 8E:
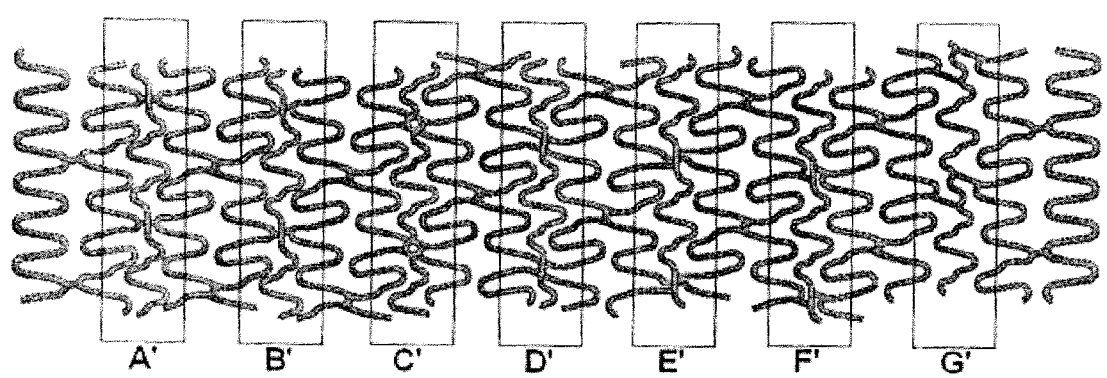
Figure 8F:
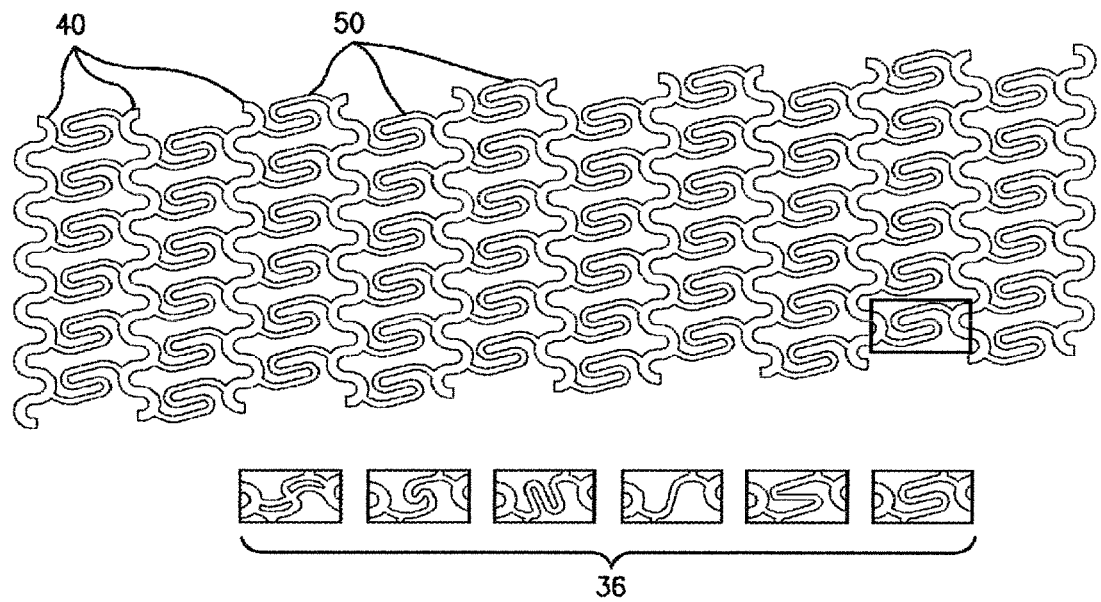
Figure 8G:
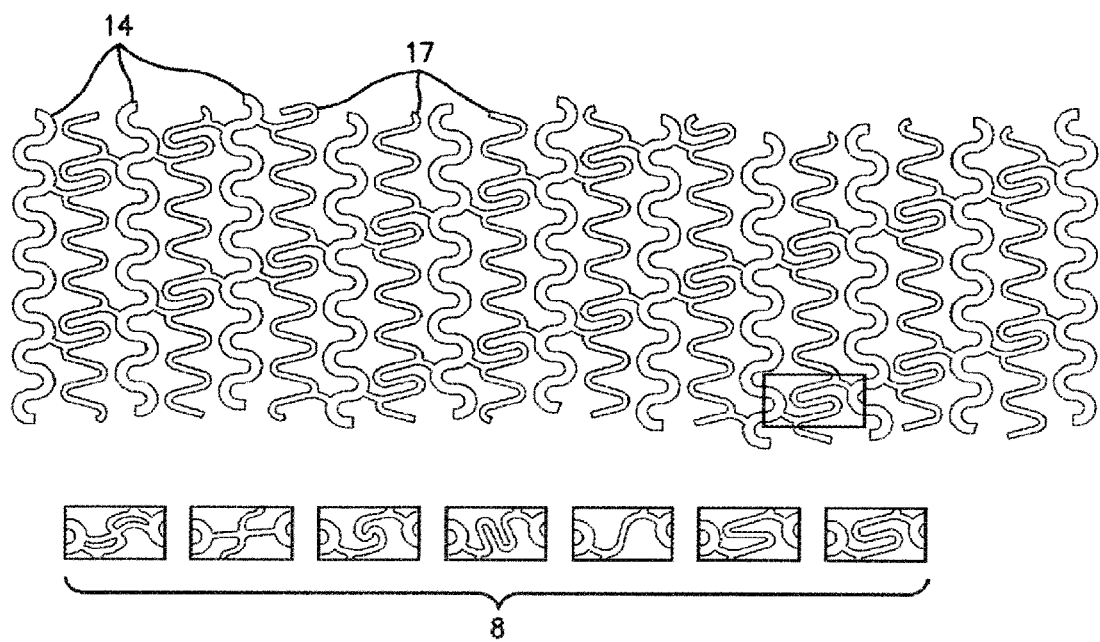
FIG. 8G is a planar view of a bioabsorbable stent scaffold wall showing an alternate design embodiment of the strut and hoop/ring patterns and how the design can be modified by alternate connection elements to change the flexibility of the stent scaffold.
Figure 8H:
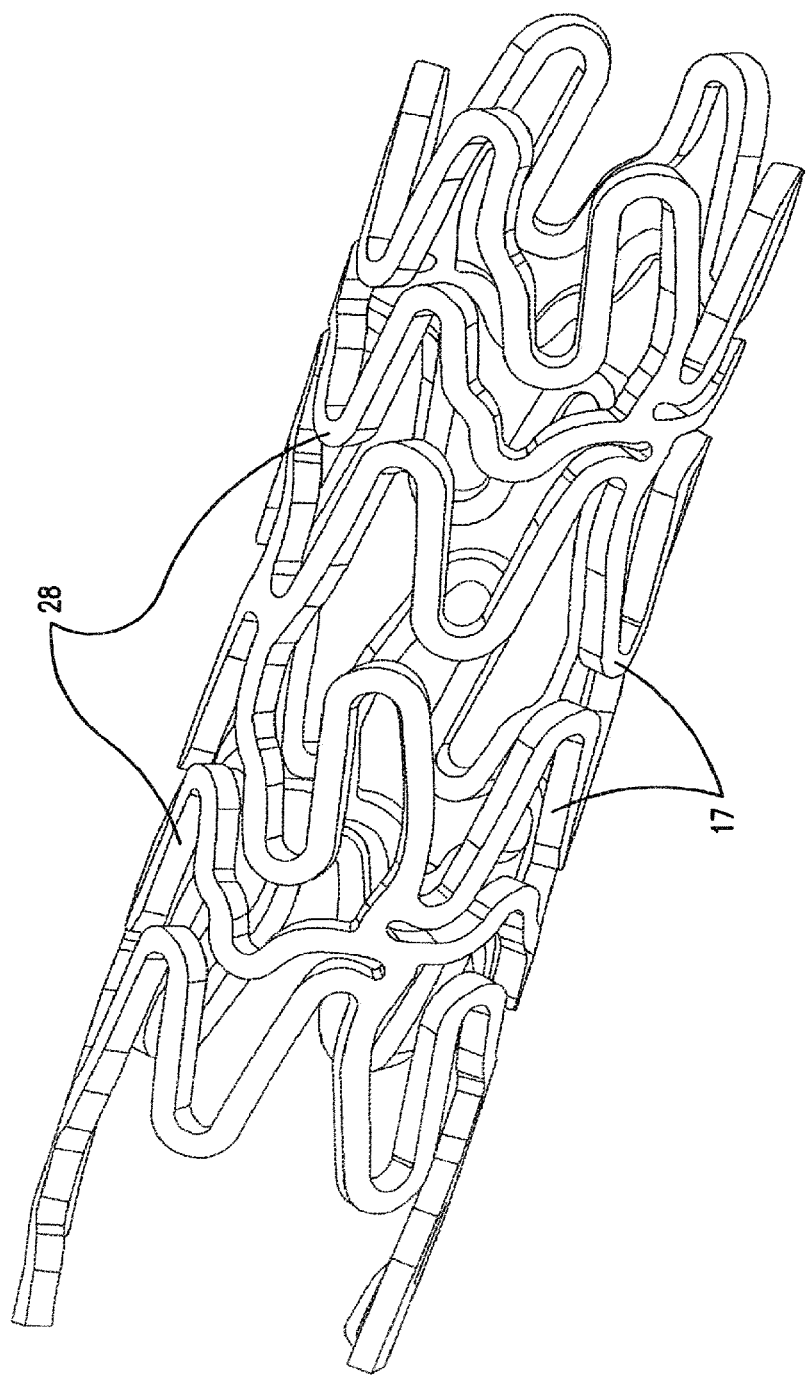
FIG. 8H illustrates a stent scaffold as manufacture which shows the nested hoop/ring structure intercalated between meandering strut elements.
Figure 8I:
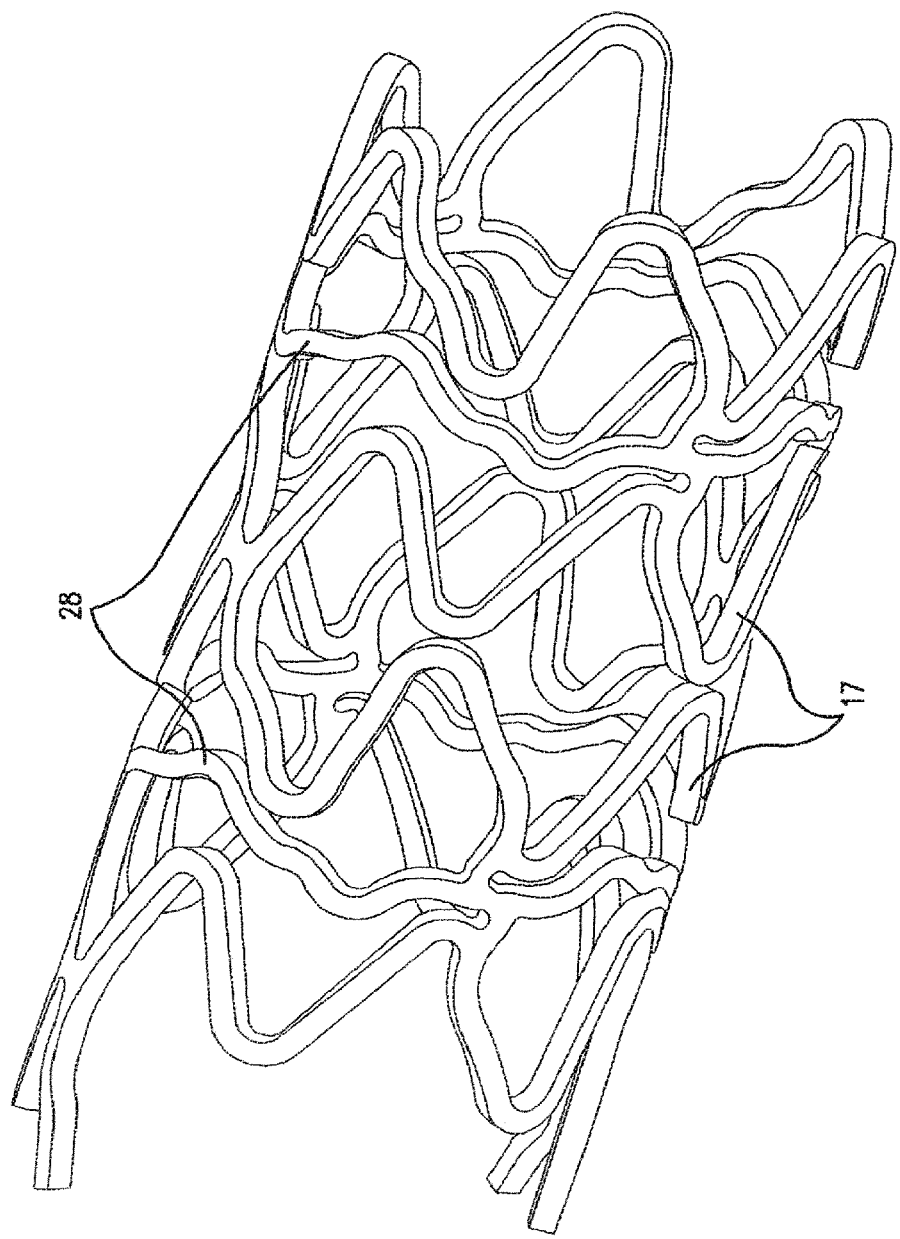
FIG. 8I is FIG. 8H in a partially expanded configuration.
Figure 8K:
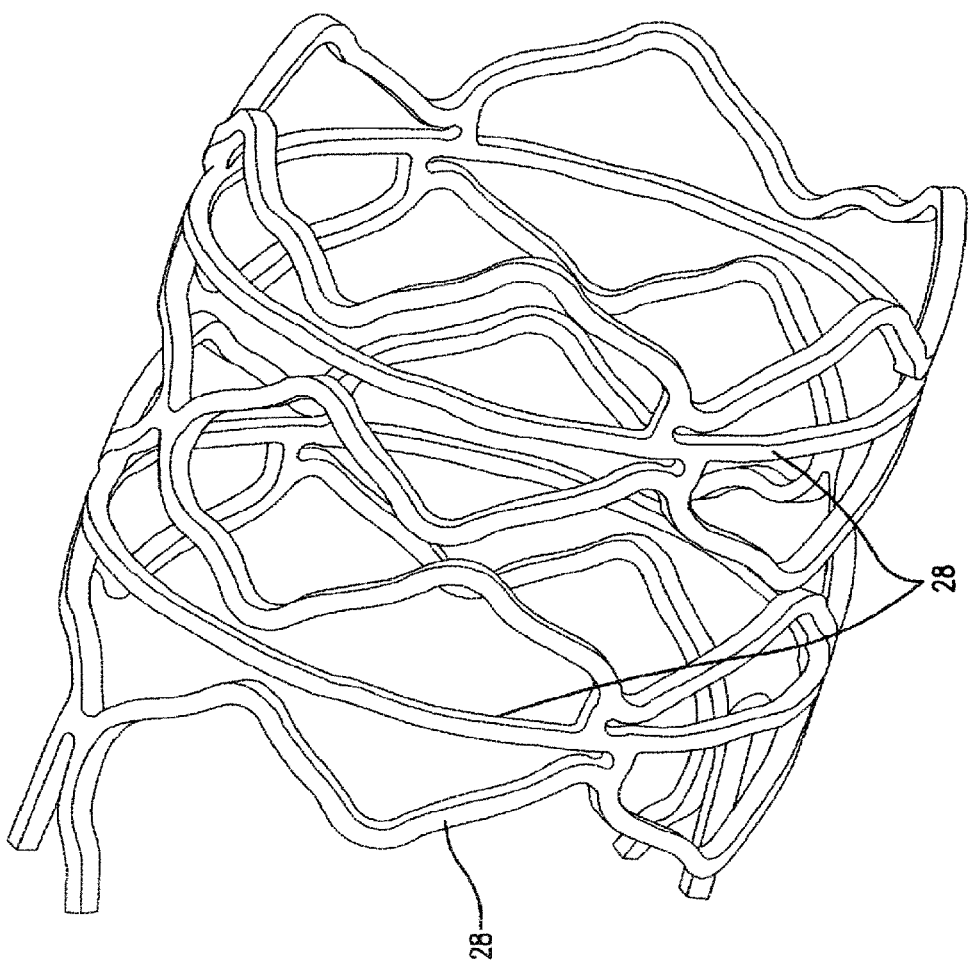
FIG. 8J is the same as 8H in an expanded configuration and FIG. 8K in a fully expanded configuration.

FIG. 8A illustrates a planar view of an unexpanded bioabsorbable stent scaffold embodiment comprising, structural meandering strut elements 17, nested hoop/ring elements 14 and having end rings 16 at the openings of the stent tube. FIG. 8B is a planar view of a section of the stent scaffold of FIG. 8A illustrating the structural meandering strut elements 17, nested hoop/ring elements 28, 30 and connection structures which form the stent scaffold. The stent scaffold is shown in a state as manufactured and also shows the nested rings structures 28, 30 in various configurations. Focusing on the connections between structural meandering elements and hoop elements there may be seen the shape of a stylized letter H. FIG. 8C illustrates the segment of FIG. 8B in an expanded configuration. FIGS. 8D, 8E and 8F are planar views of bioabsorbable stent scaffold walls showing alternate design embodiments 17 of the connection points between meandering strut elements 17 and ring structures 15 (nested) and 16 (terminal ring structure). FIG. 8G is a planar view of a bioabsorbable stent scaffold wall showing an alternate design embodiments of the strut and hoop/ring patterns and how the design can be modifies by alternate connection elements to change the flexibility of the stent scaffold. FIG. 8H illustrates a stent scaffold as manufacture which shows the nested hoop/ring structure intercalated between meandering strut elements. FIG. 8I is FIG. 8H in a partially expanded configuration, and FIG. 8J is the same as 8H in an expanded configuration and FIG. 8K in a fully expanded configuration.

Figure 9A:
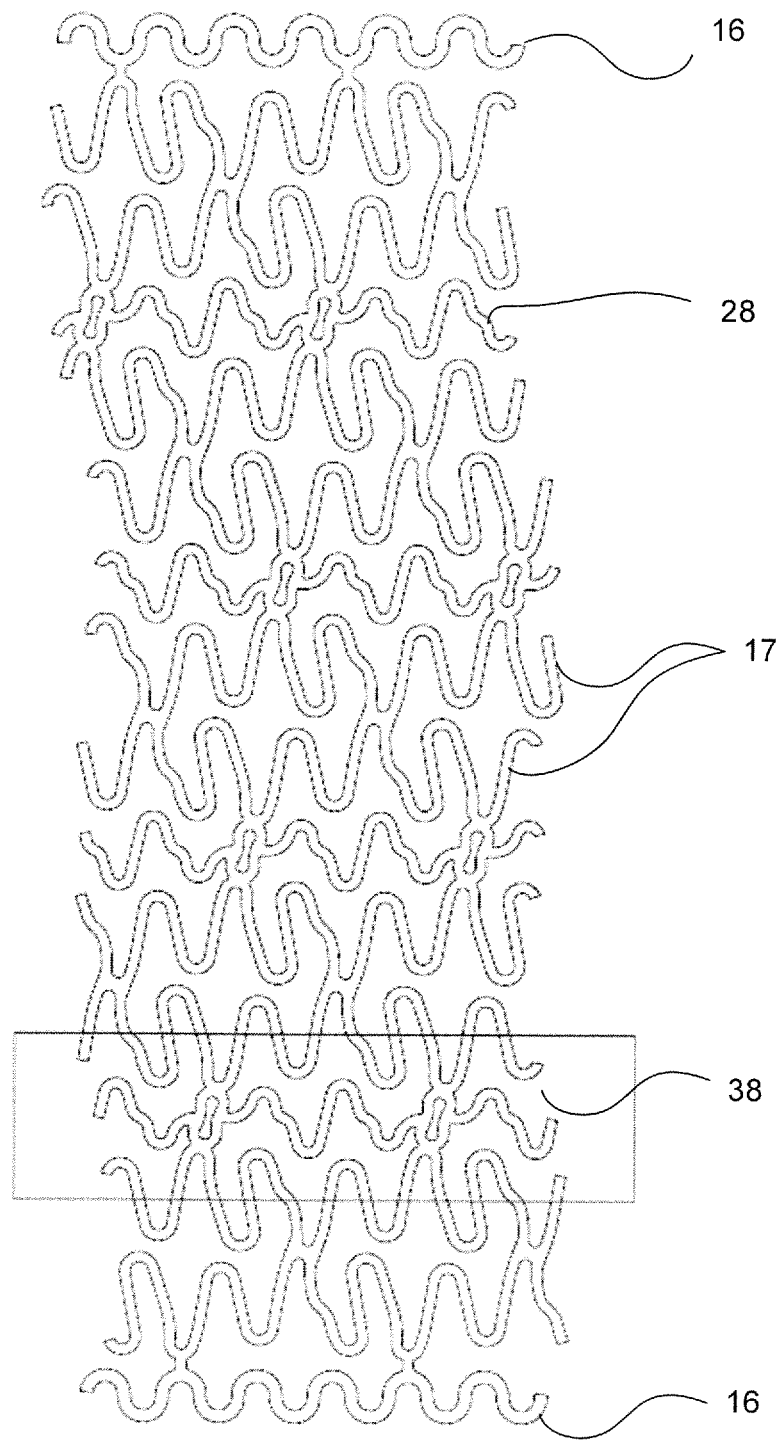
FIG. 9A depicts a planar view illustration of a bioabsorbable stent scaffold showing the various components, nested hoop/ring structural elements, meandering/sinusoidal strut components, end ring element and modified connection structures having an o-ring like shape where the elements meet.
Figure 9B:
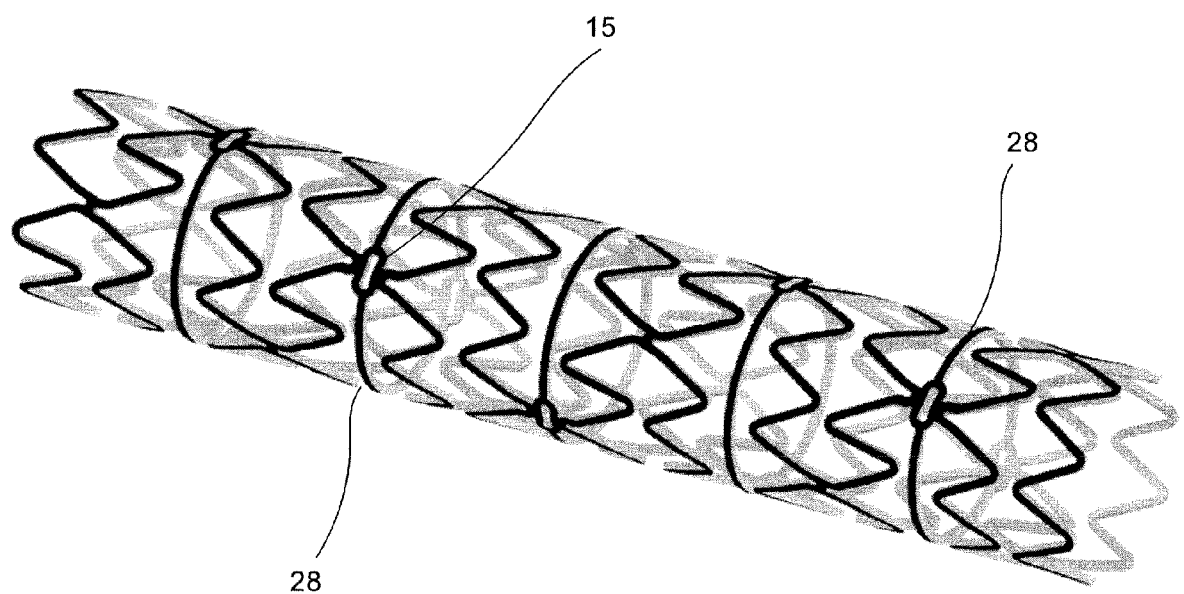
FIG. 9B illustrates an oblique view of a stent structure scaffold as illustrated in FIG. 9A in an expanded configuration.

FIG. 9A depicts a planar view illustration of a bioabsorbable stent scaffold showing the various components, nested hoop/ring structural elements 28, meandering/sinusoidal strut components 38, end ring elements 16 and modified connection structures 6 having an o-ring like shape where the elements meet. FIG. 9B illustrates an oblique view of a stent structure scaffold as illustrated in FIG. 9A in an expanded configuration.

FIG. 10A illustrates the connection structures 6 of a bioabsorbable scaffold as described in FIG. 9A showing the state of the connections as manufactured; FIGS. 10B and 10C in a partially expanded state and FIG. 10D in a fully expanded state. As illustrated the through-void shape changes as the scaffold is expanded.

Figure 11A:
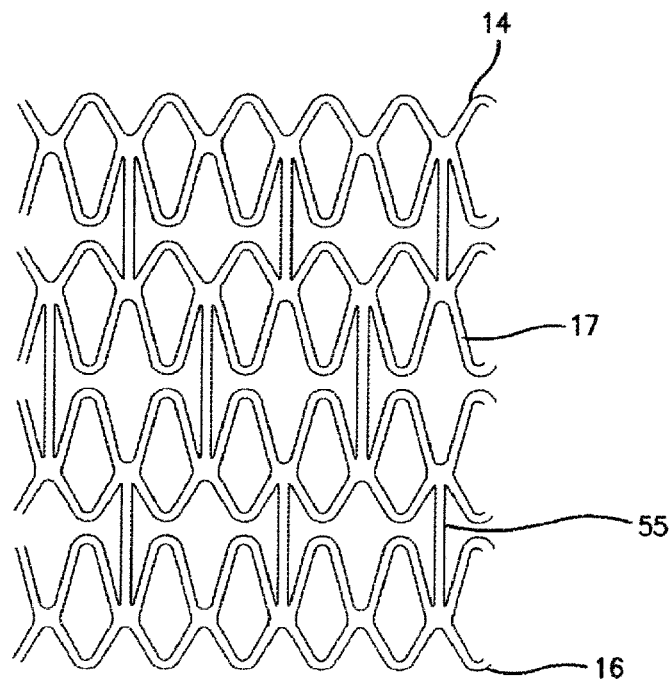
FIG. 11A depicts a planar view of an unexpanded alternate bioabsorbable stent scaffold design showing alternate pattern of connections between strut elements and comprising end rings structures.
Figure 11B:
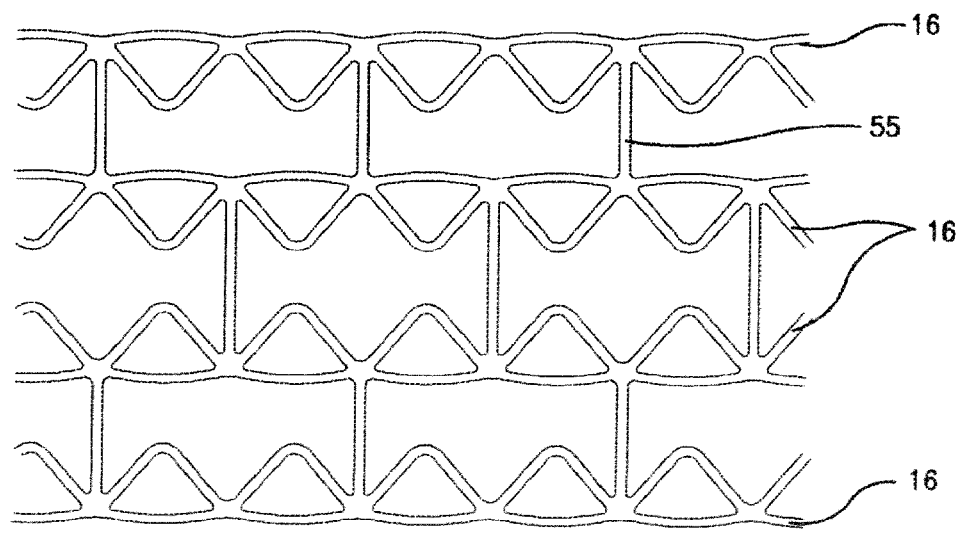
FIG. 11B is FIG. 11A in an expanded configuration.
Figure 11C:
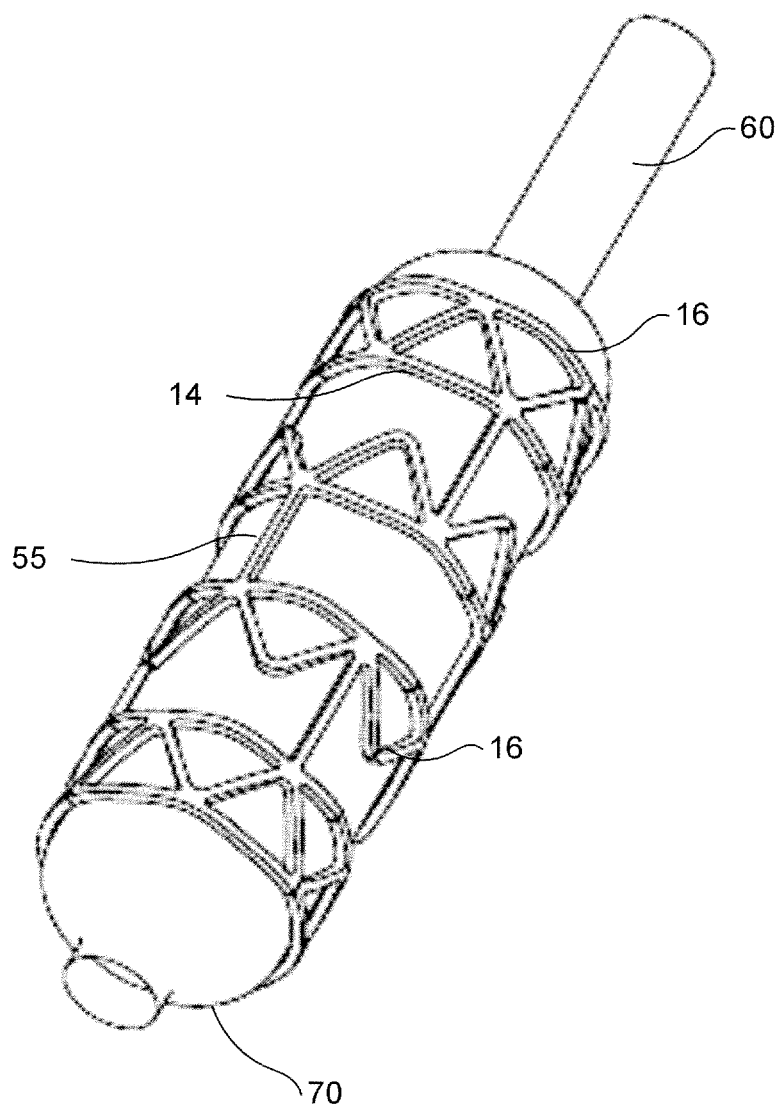
FIG. 11C illustrates a bioabsorbable stent structure as illustrated in FIG. 11A mounted on a balloon catheter in an expanded configuration.

FIG. 11A depicts a planar view of an unexpanded alternate bioabsorbable stent scaffold design showing alternate pattern of connections between strut elements and comprising end rings structures. FIG. 11B is FIG. 11A in an expanded configuration. FIG. 11C shows the same in expanded state deployed on a expanded balloon catheter.

Figure 12A:
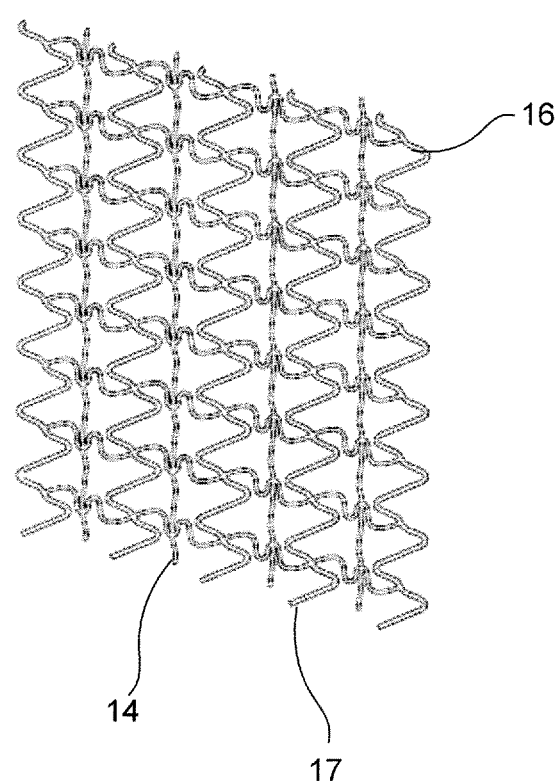
FIG. 12A depicts a planar view of an alternate embodiment of a bioabsorbable stent scaffold structure showing alternate design for the strut elements in expanded configuration and hoop/ring elements.
Figure 12B:
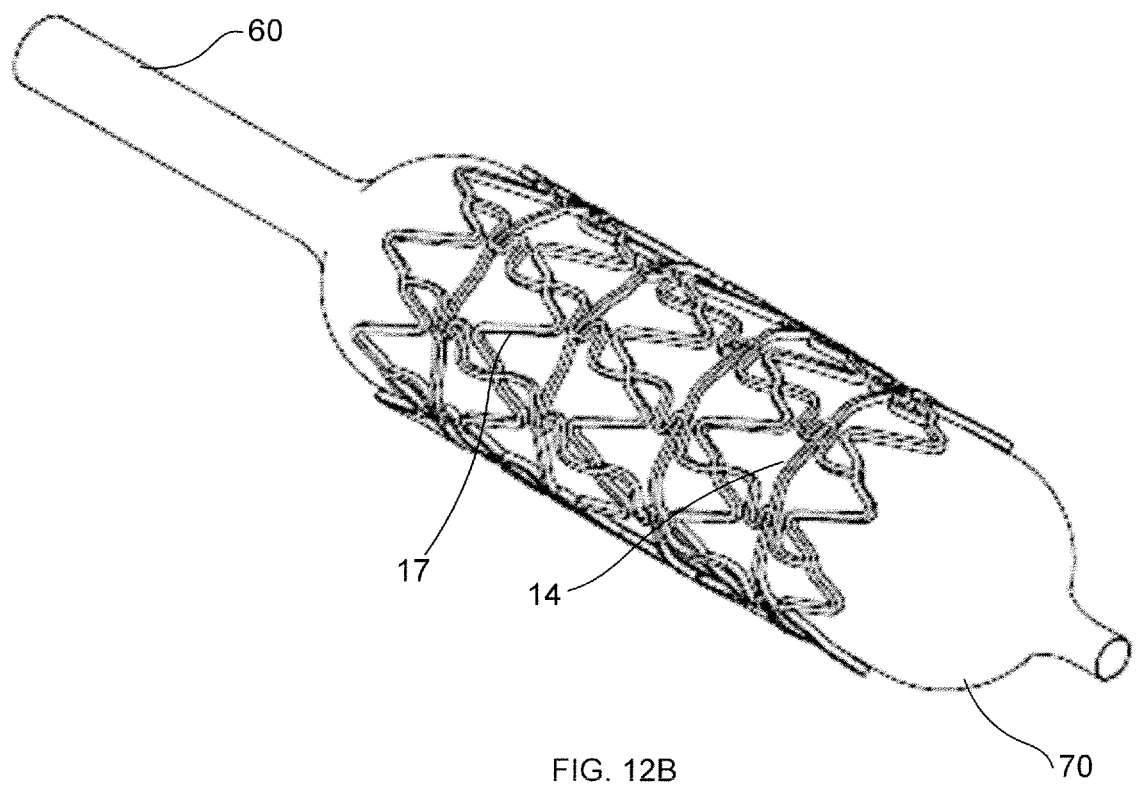
FIG. 12B is a bioabsorbable stent structure of FIG. 12A in an expanded configuration and mounted on a balloon catheter.

FIG. 12A depicts a planar view of an alternate embodiment of a bioabsorbable stent scaffold structure showing alternate design for the strut elements in expanded configuration including hoop/ring elements 14 and 16. FIG. 12B may be a bioabsorbable stent structure of FIG. 12A in an expanded configuration and mounted on a balloon catheter.

Figure 13A:
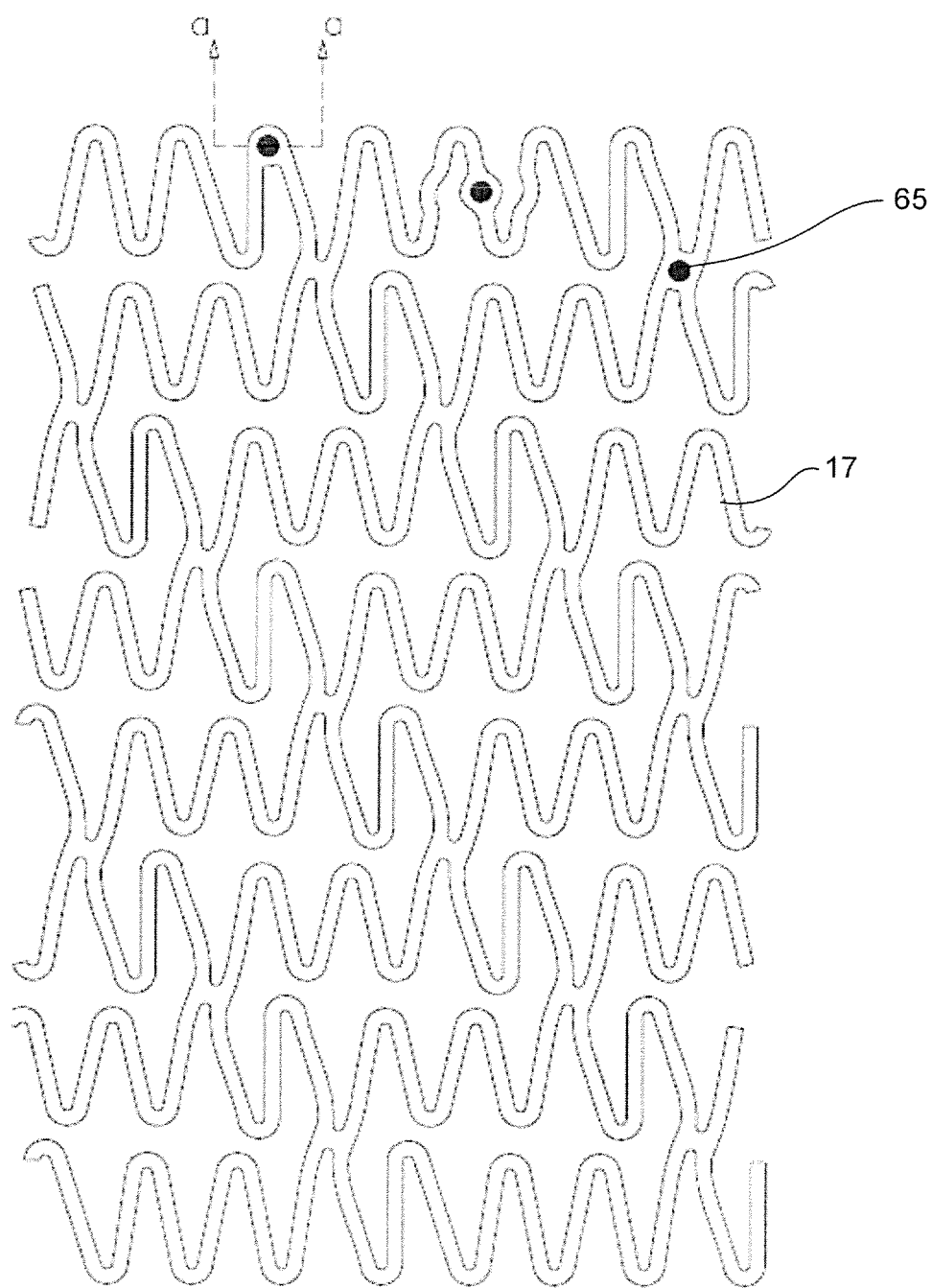
FIG. 13A illustrates a bioabsorbable stent scaffold embodiment comprising radio-opaque marker structures positioned at the end ring and the connection elements between strut segments.
Figure 13B:
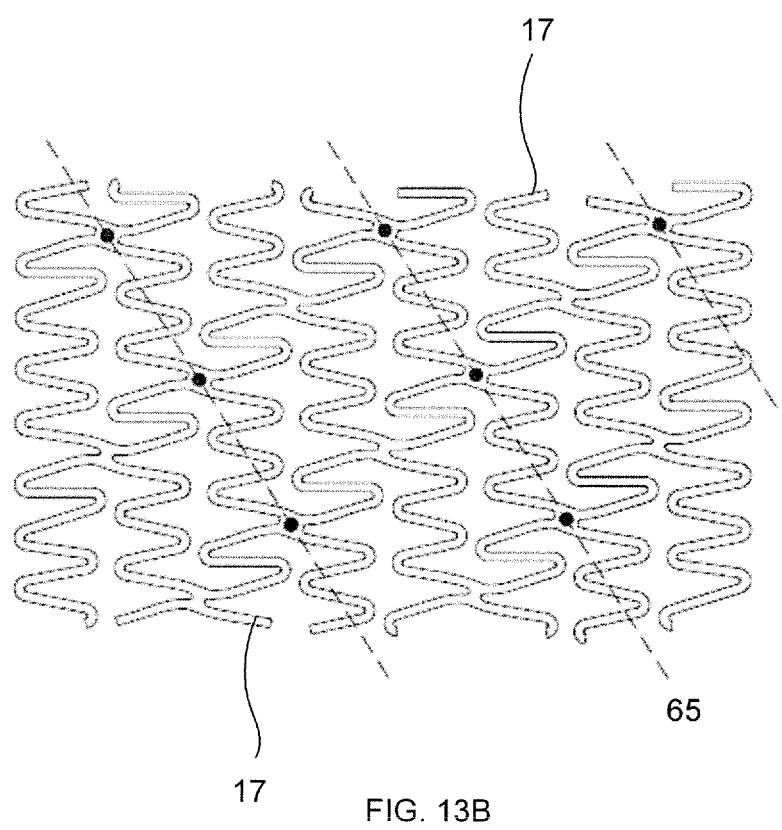
FIG. 13B illustrates an embodiment wherein the radio-opaque material is position in a diagonal pattern for identification by radiography of the device after implantation.
Figure 14A:
FIG. 14A-14D illustrates alternate embodiments of isolated marker label structures of a bioabsorbable stent scaffold in cross-section.
Figure 14B:
Figure 14C:
Figure 14D:

FIG. 13A illustrates a bioabsorbable stent scaffold embodiment comprising radio-opaque marker structures 65 positioned at the end ring and the connection elements between strut segments. FIG. 13B illustrates an embodiment wherein the radio-opaque material is position in a diagonal pattern 65' for identification by radiography of the device after implantation.

FIG. 14A-14D illustrates alternate embodiments of isolated marker label structures of a bioabsorbable stent scaffold in cross-section. As illustrated the isolated marker may be placed on the stent (14D), or in a recess (14B) or in a variety of through-holes (14A and 14C).

Figure 15A:
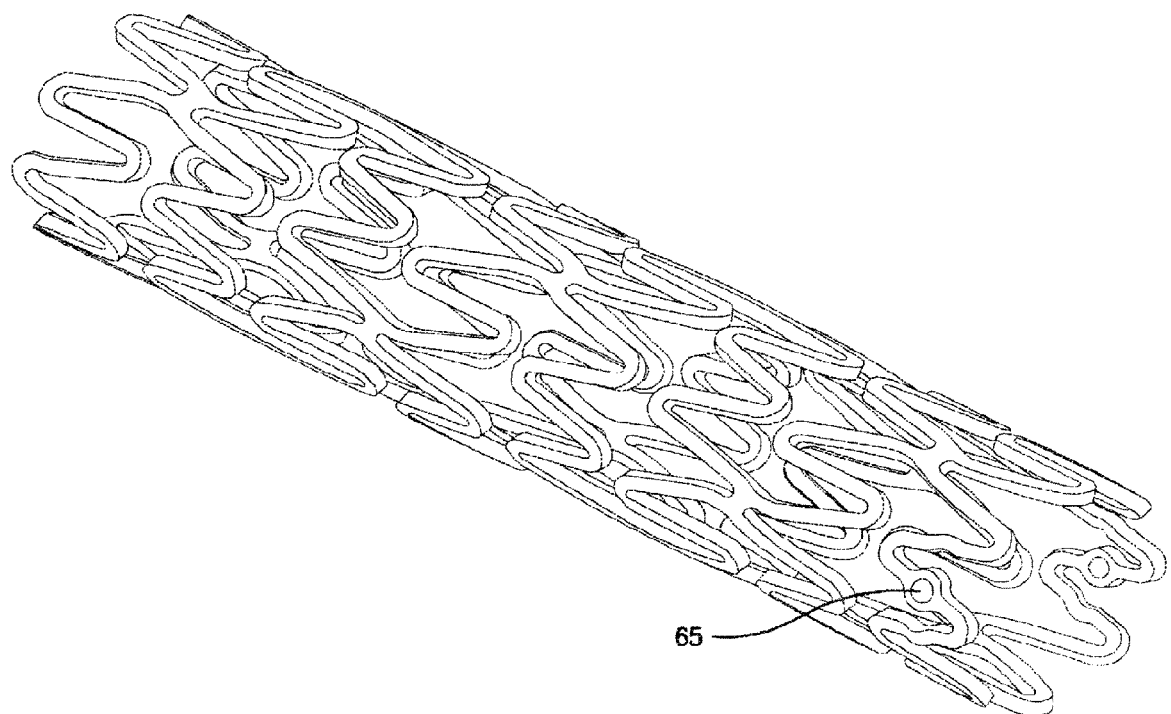
FIGS. 15A and 15B further illustrate the position at which label radio-opaque markers are placed in a bioabsorbable stent scaffold embodiment and FIG. 15C is a radiography of a radio-opaque marker label in a bioabsorbable stent strut embodiment.
Figure 15B:
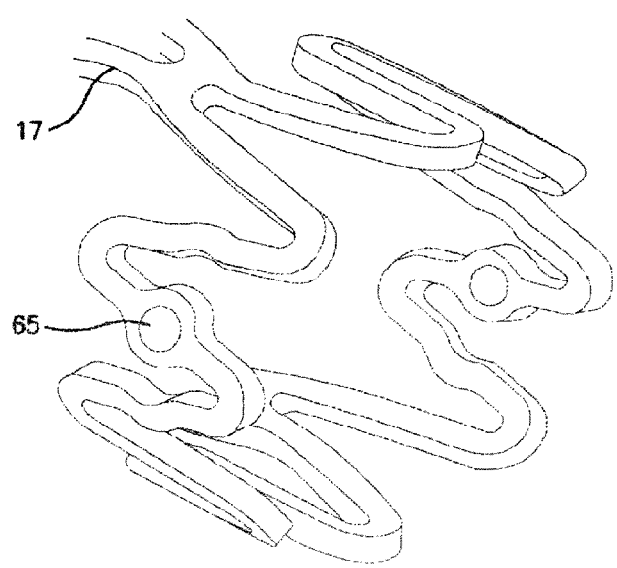
Figure 15C:
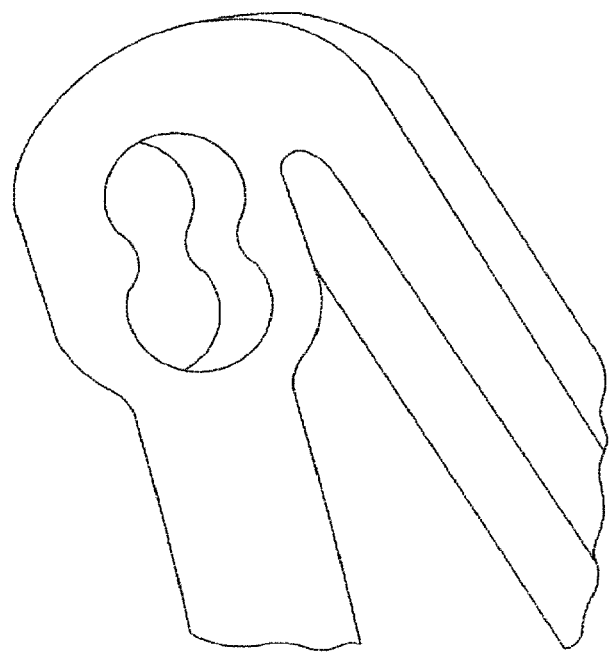

FIGS. 15A and 15B further illustrate the position at which label radio-opaque markers 65 are placed in a bioabsorbable stent scaffold embodiment. FIG. 15C is a close-radiograph of a radio-opaque marker label in a bioabsorbable stent strut embodiment.

Figure 16A:
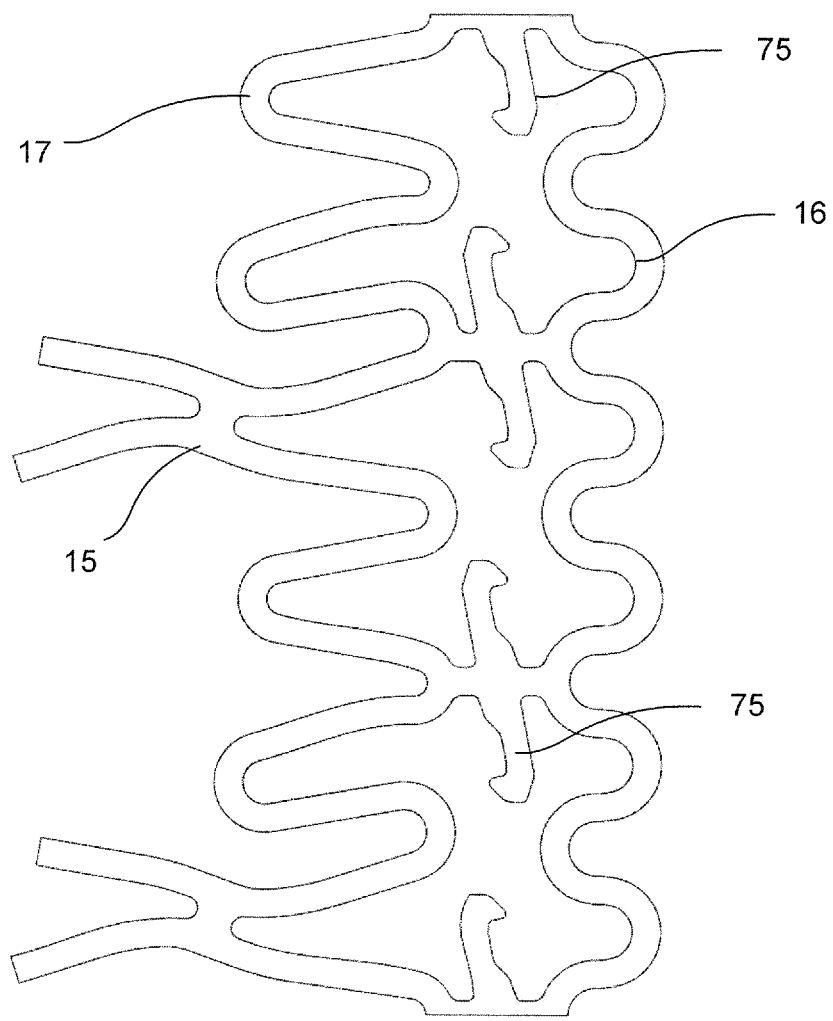
FIG. 16A is an illustration of a planar view of an end of a stent embodiment comprising an end ring element, a locking mechanism and a stent strut meandering element in an expanded configuration.
Figure 16B:
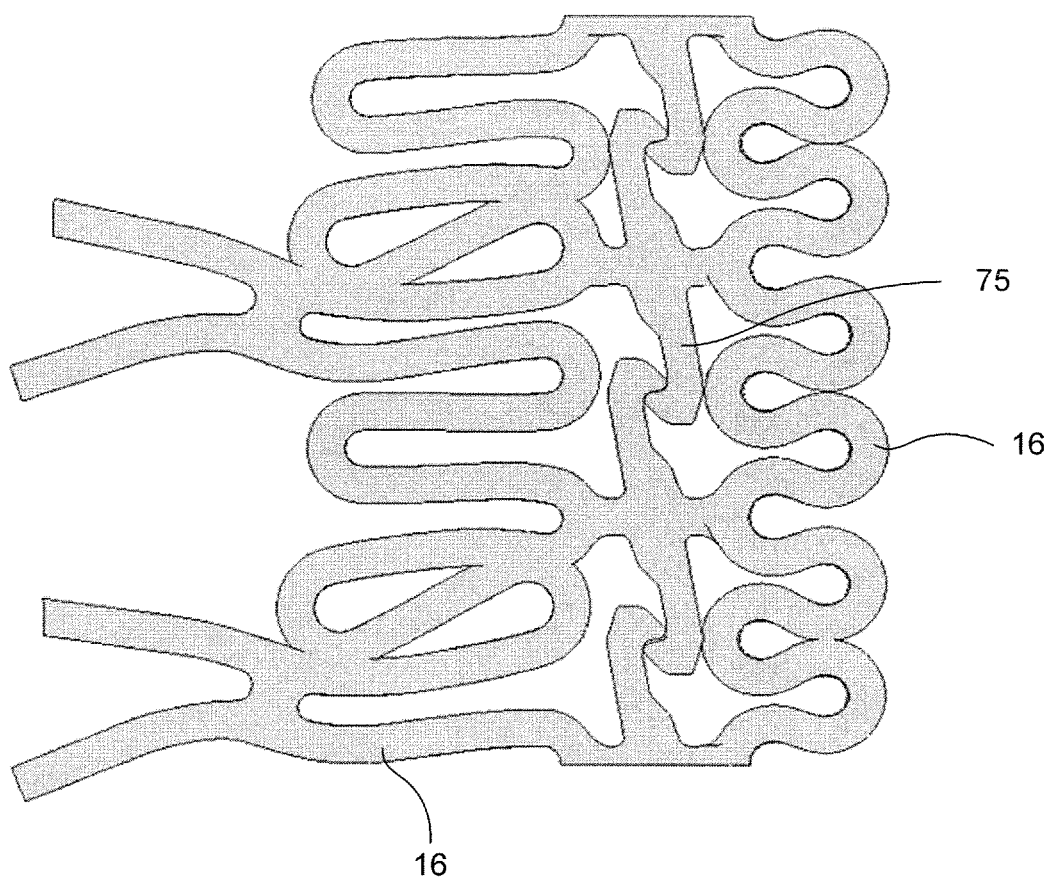
FIG. 16B is FIG. 16A showing the stent scaffold in a crimped configuration.
Figure 16C:
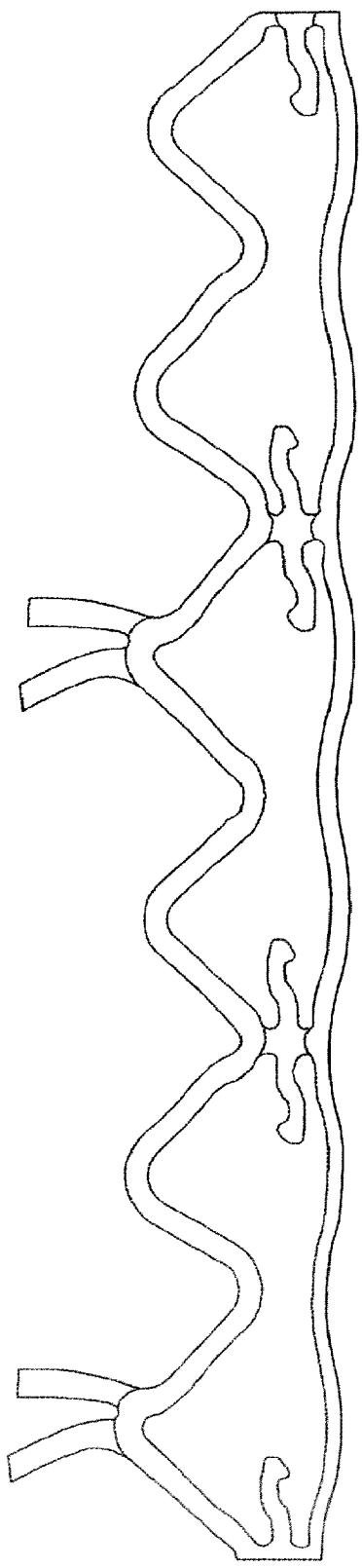
FIG. 16C is an illustration of an the expanded stent scaffold showing the stress force distribution.
Figure 16D:
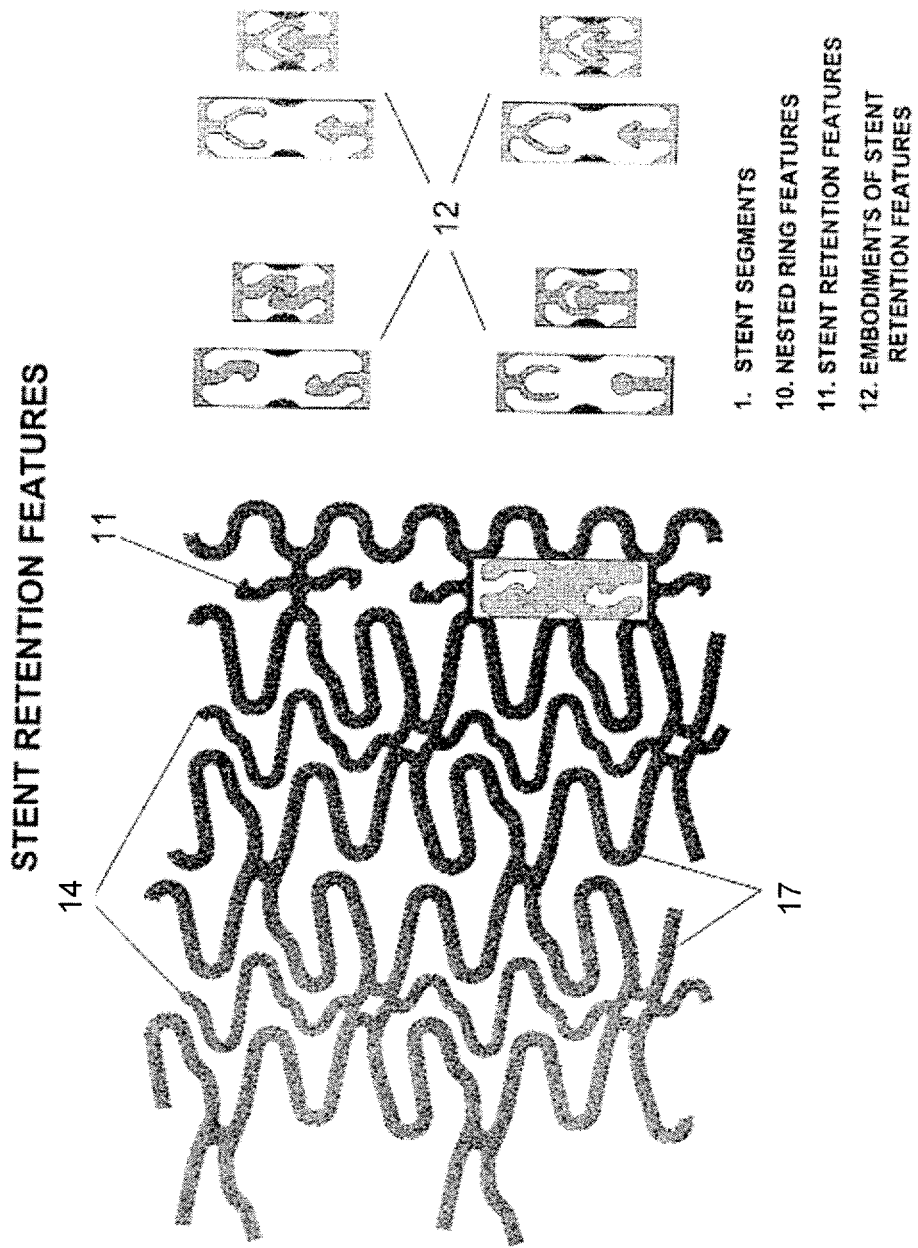
FIG. 16D illustrates a segment of a bioabsorbable stent scaffold embodiment showing nested hoop/ring structures, stent meandering segments and locking mechanisms or retention features which can alternate in design for engagement.

FIG. 16A is an illustration of a planar view of an end of a stent embodiment comprising an end ring element 16, a locking mechanism 75 and a stent strut meandering element 17 in an expanded configuration. FIG. 16B is FIG. 16A showing the stent scaffold in a crimped configuration with interlocking locking mechanisms 75. FIG. 16C is an illustration of an the expanded stent scaffold showing the stress force distribution, and showing the decoupling of locking mechanisms 75 when in the stent is in an expanded configuration. FIG. 16D illustrates a segment of a bioabsorbable stent scaffold embodiment showing nested hoop/ring structures 14, stent meandering segments 17 and locking mechanisms 11 or retention features which can alternate in design for engagement.

Figure 17A:
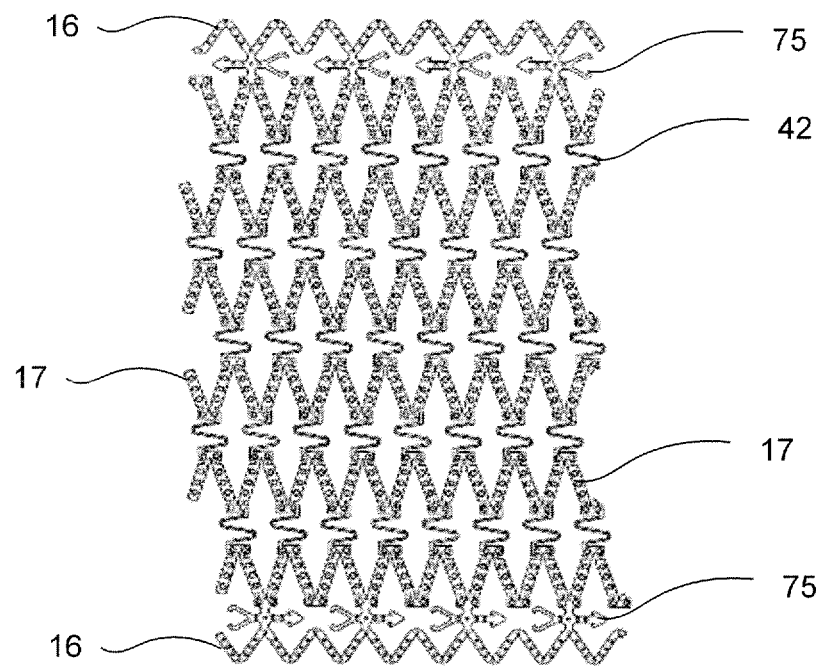
FIGS. 17A and 17B depict alternate embodiments of a stent scaffold in expanded planar view and showing disengaged locking mechanisms and end ring structures at its ends.
Figure 17B:
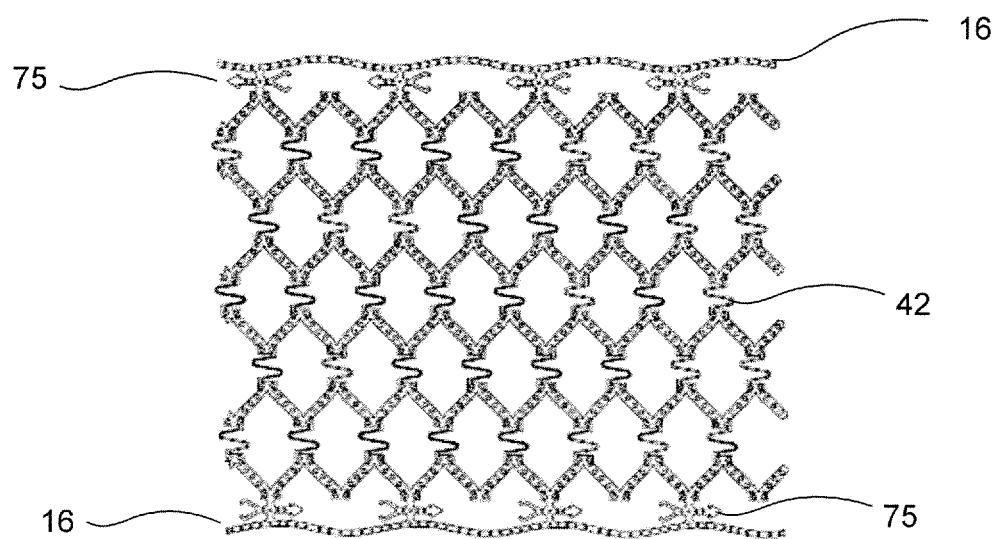

FIGS. 17A and 17B depict alternate embodiments of a stent scaffold in expanded planar view and showing disengage locking mechanisms 75 and end ring structures 16 at its ends. As shown locking mechanisms 75 are snap-fit connections with male-female portions.

Figure 18A:
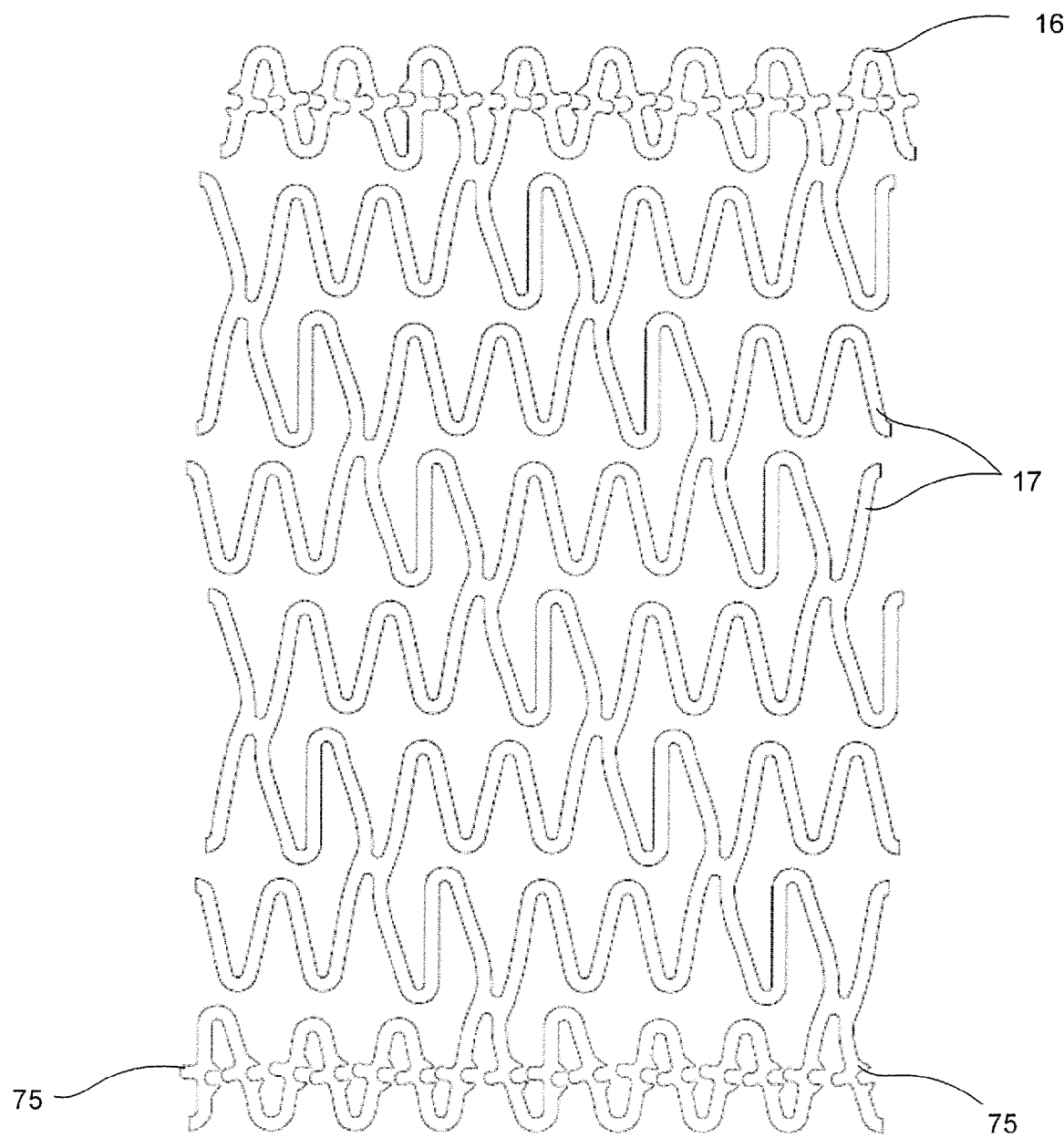
FIGS. 18A-18F are illustrations of an alternate embodiment of a bioabsorbable stent scaffold showing the locking mechanism at the end rings of the device in planar and oblique views as well as disengage and engage positions.
Figure 18B:
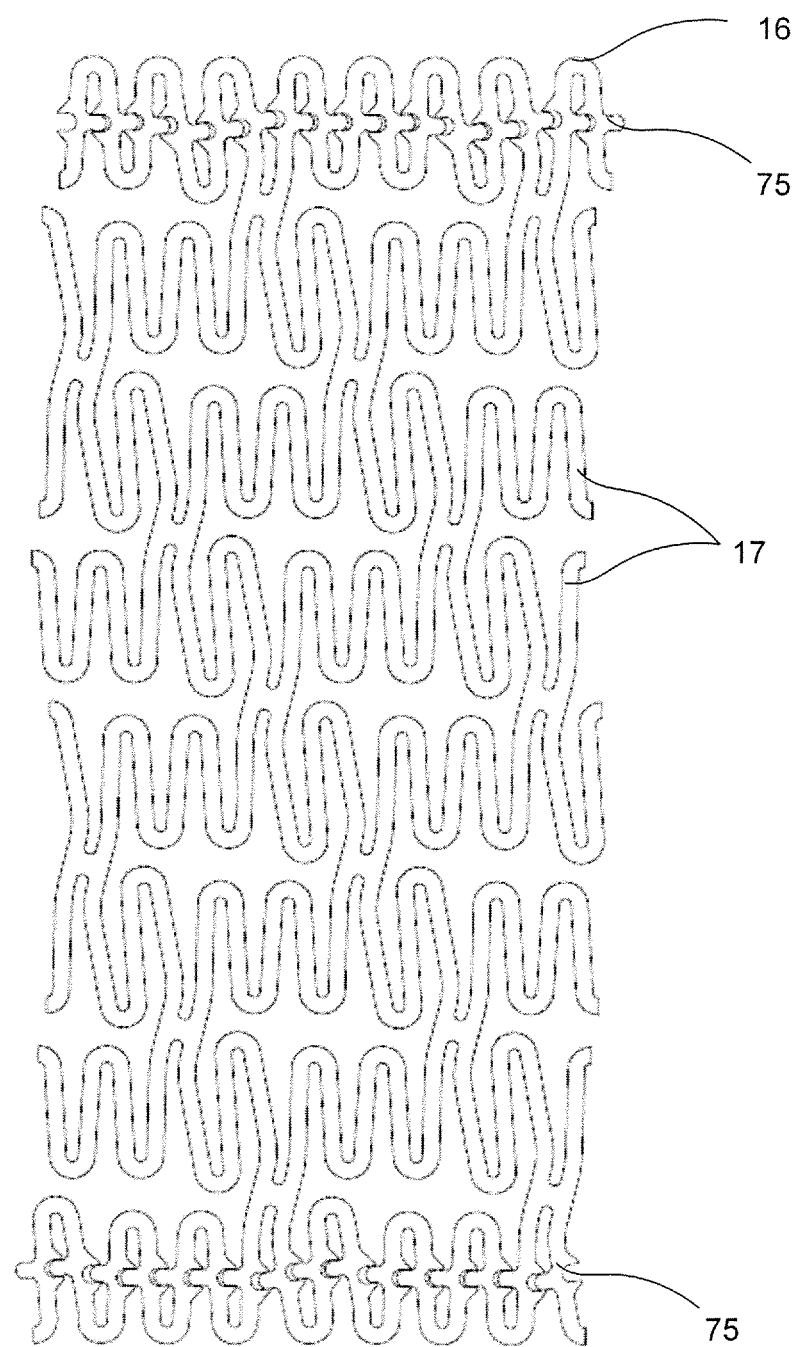
Figure 18C:
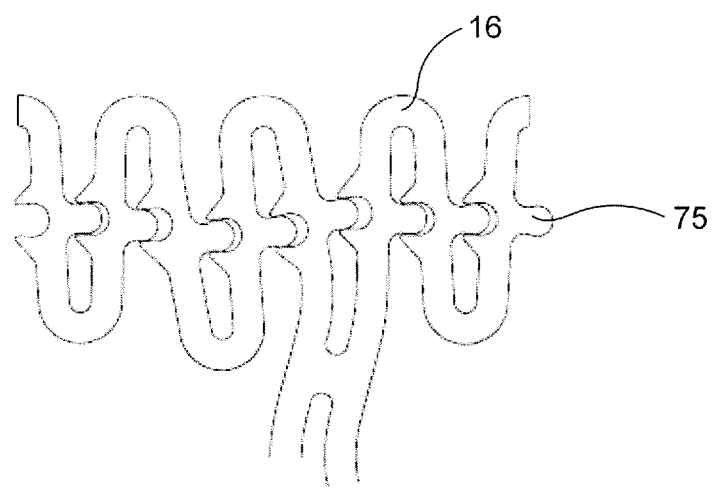
Figure 18D:
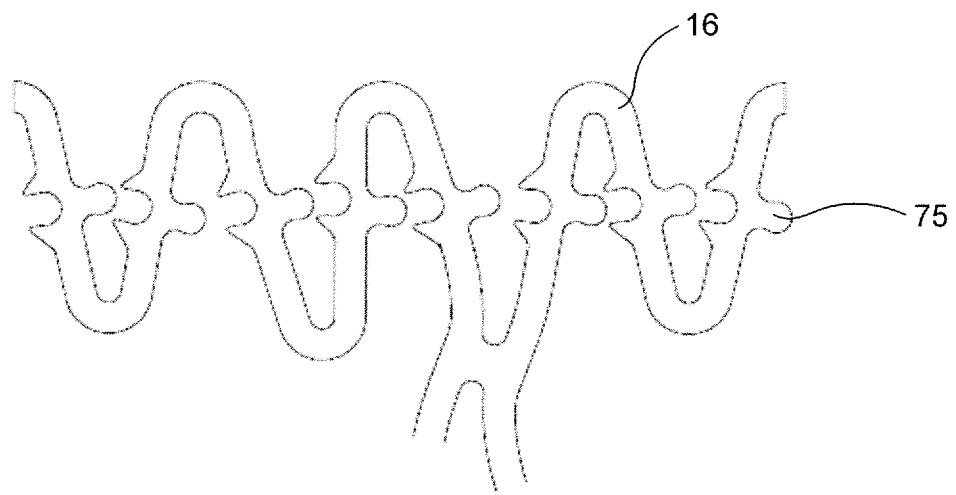
Figure 18E:
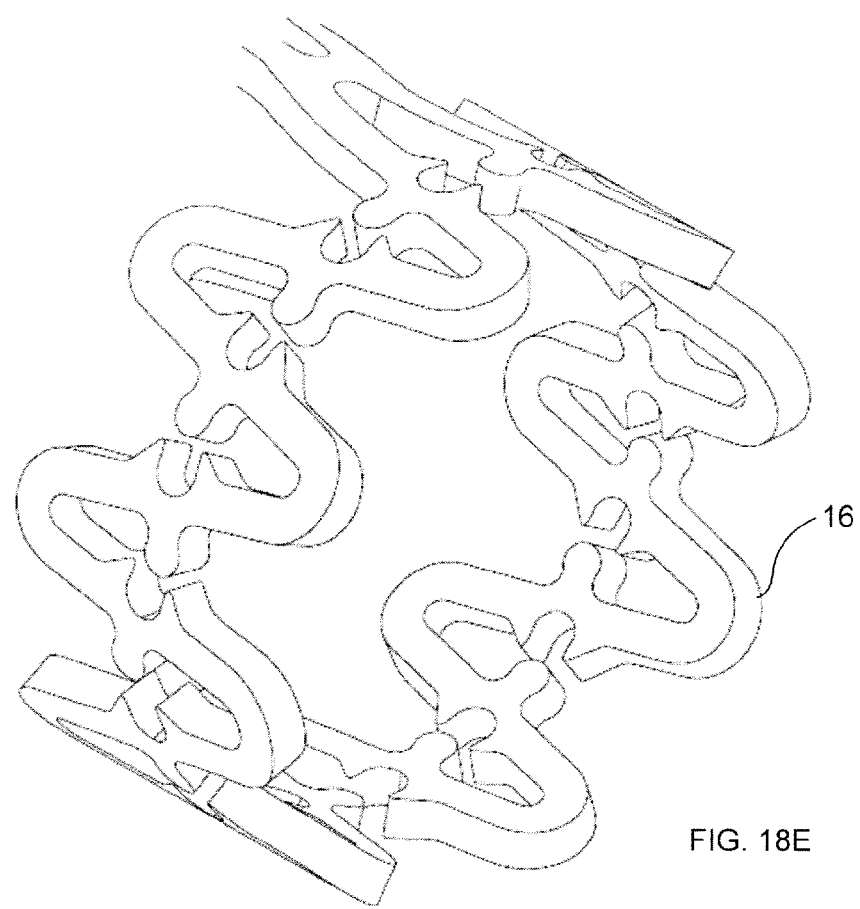
Figure 18F:
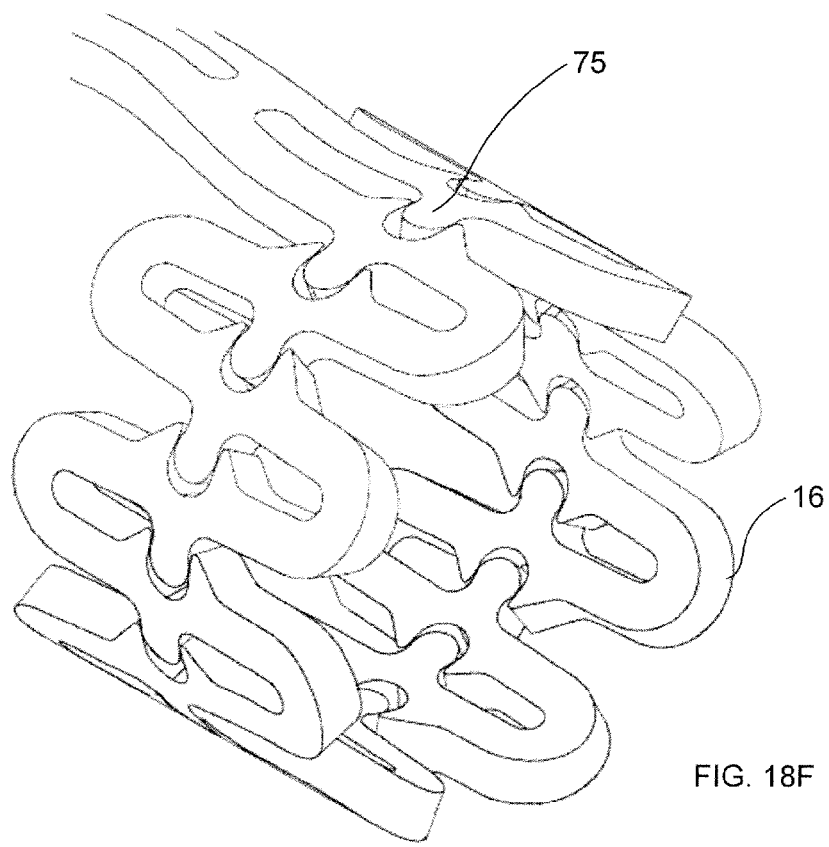
Figure 18G:
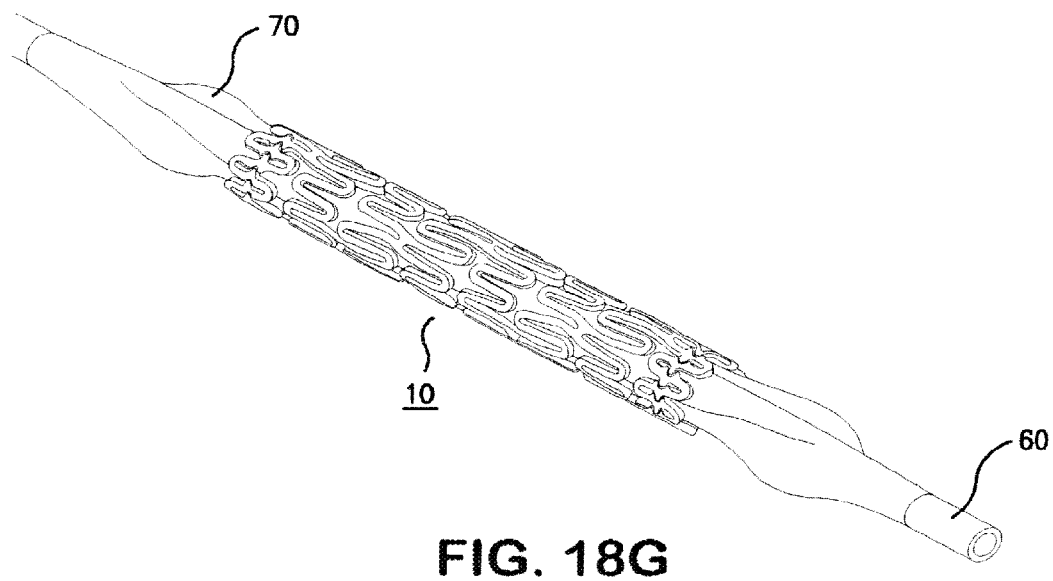
FIG. 18G illustrates an embodiment wherein the stent scaffold is mounted on a balloon catheter and the locking mechanism are engage to retain the stent on the catheter in a uniform configuration in the plane of the body of the stent.
Figure 18H:
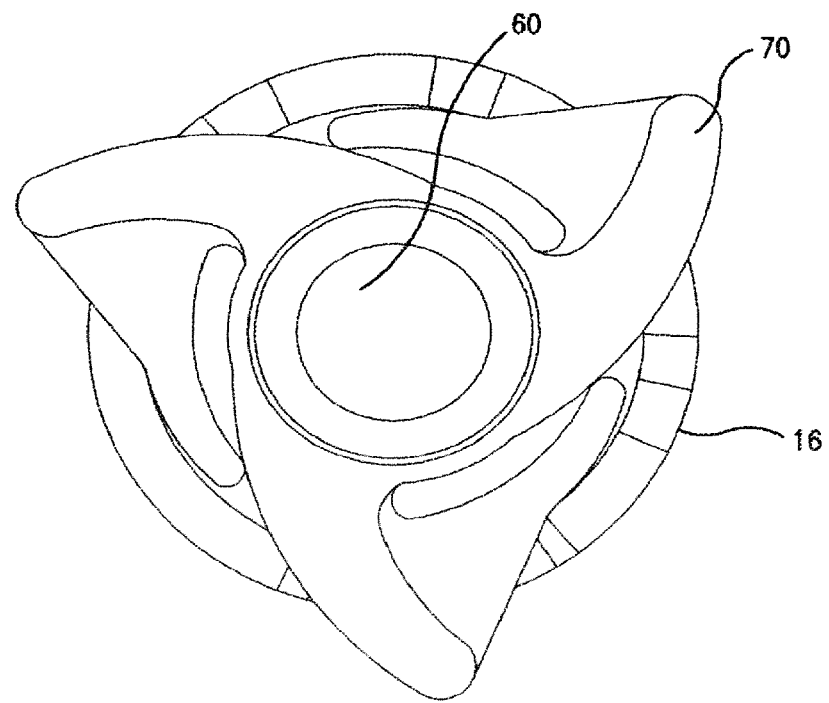
FIG. 18H is a frontal view of the stent scaffold of FIG. 18G showing the catheter as a circle, end ring and balloon.

FIGS. 18A-18F are illustrations of an alternate embodiment of a bioabsorbable stent scaffold showing the locking mechanism 75 at the end rings of the device in planar and oblique views as well as disengage and engage positions. Locking mechanism 75 in such embodiment comprises a snap-fit ball joint. FIGS. 18A, 18D and 18E show disconnected locking mechanism 75. FIGS. 18B, 18C and 18F show the locking mechanism 75 in locked state. FIG. 18G illustrates an embodiment wherein the a stent scaffold is mounted on a balloon catheter 60 and the locking mechanism are engaged to retain the stent on the catheter in a uniform configuration in the plane of the body of the stent. FIG. 18H is a frontal view of the stent scaffold 16 of FIG. 18G showing the catheter as a circle 60, end ring 16 and balloon 70.

Figure 19A:
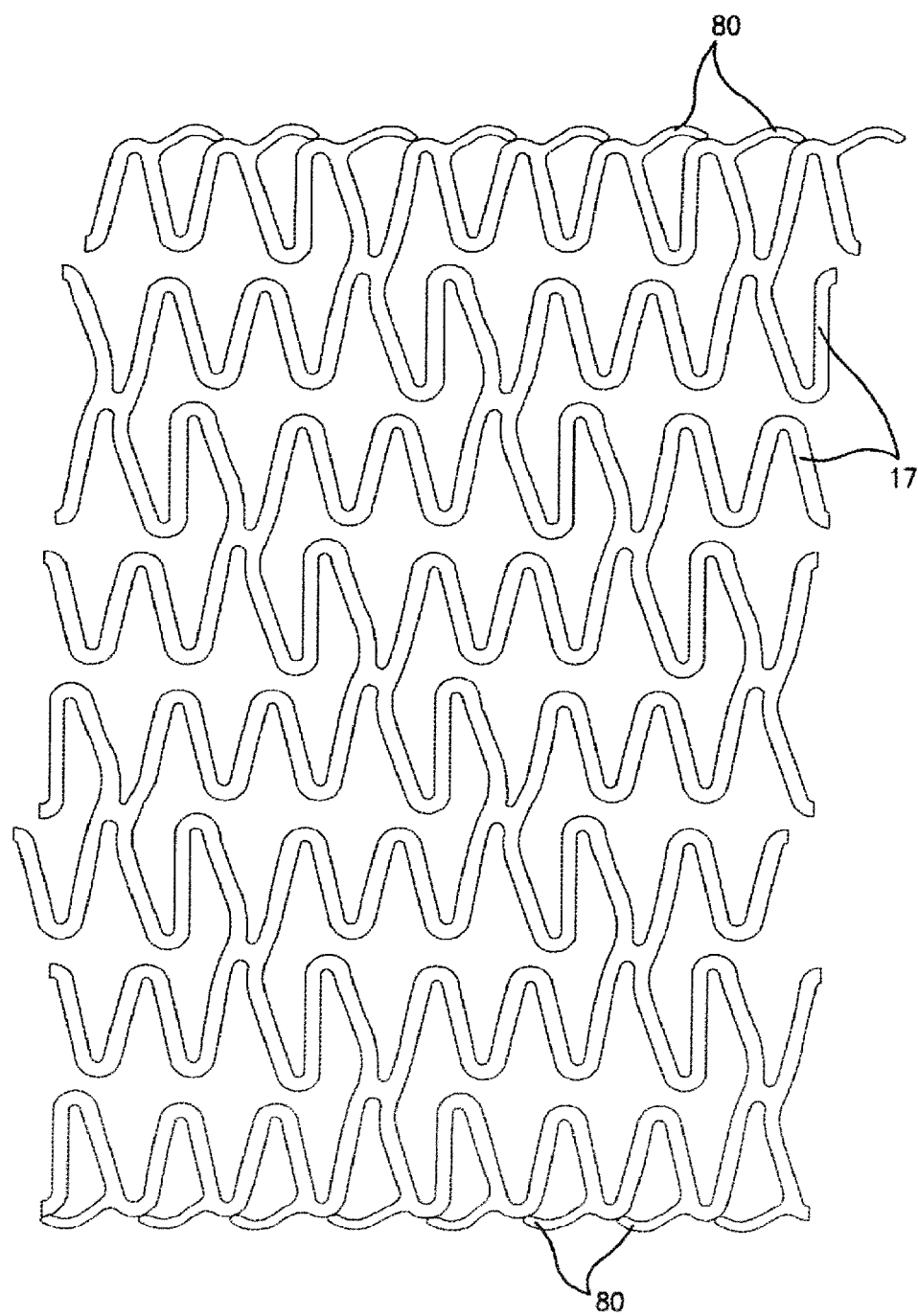
FIG. 19A depicts a planar view of a stent scaffold embodiment showing an alternate embodiment of the locking mechanism at the ends of the stent as manufactured.
Figure 19B:
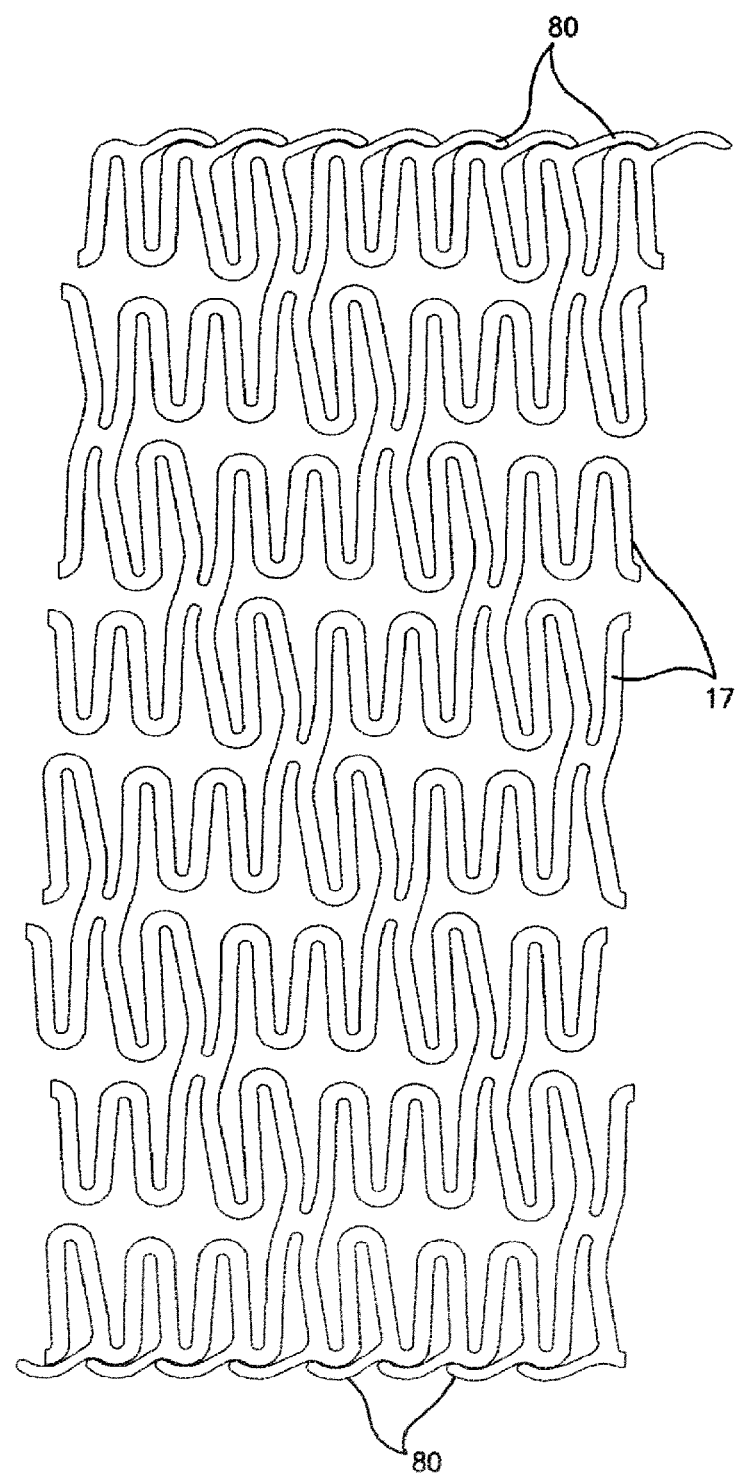
FIG. 19 B depicts FIG. 19A in a crimped position showing an engaged locking mechanism.
FIG. 19C shows an enlarged planar view of the locking mechanism in the crimped position, partially expanded configuration (FIG. 19D) and oblique views of the end rings with locking mechanism partially engaged (FIG. 19E); crimped (FIG. 19F) and mounted in a balloon catheter (FIG. 19G).
Figure 19C:
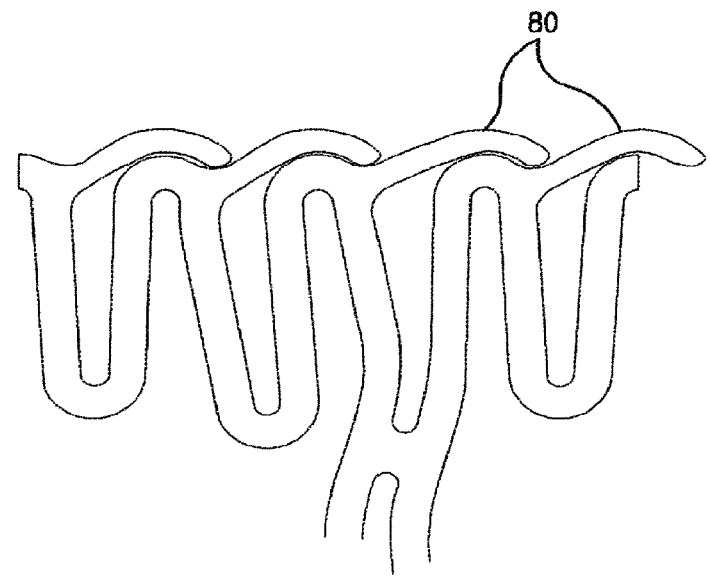
Figure 19D:
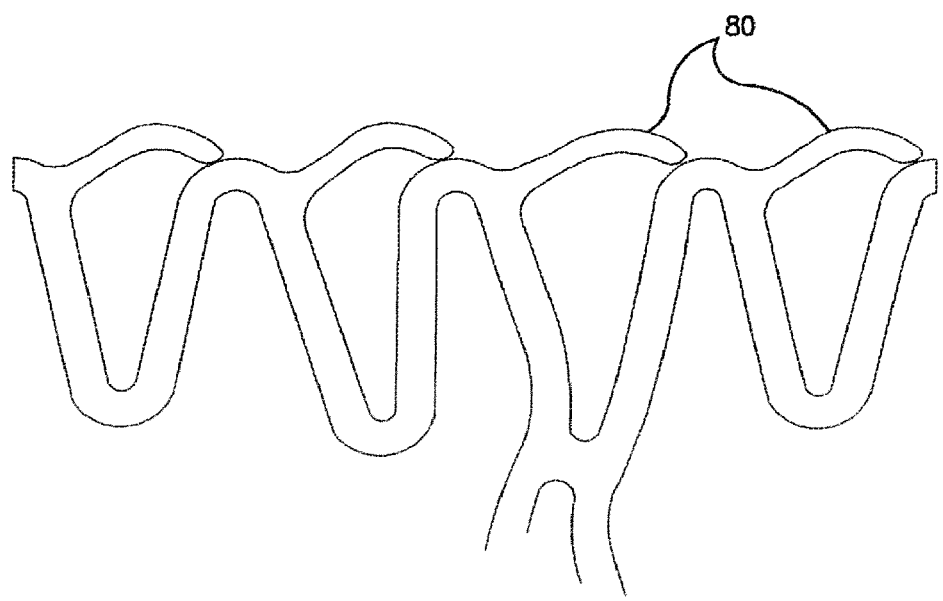
Figure 19E:
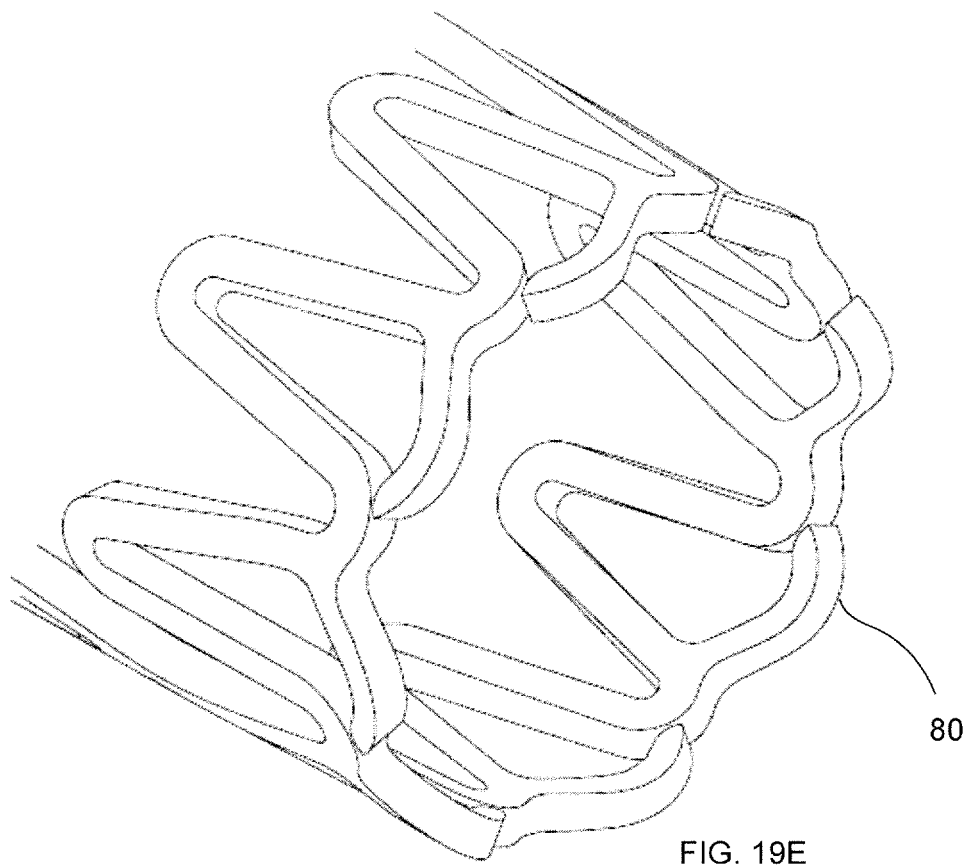
Figure 19F:
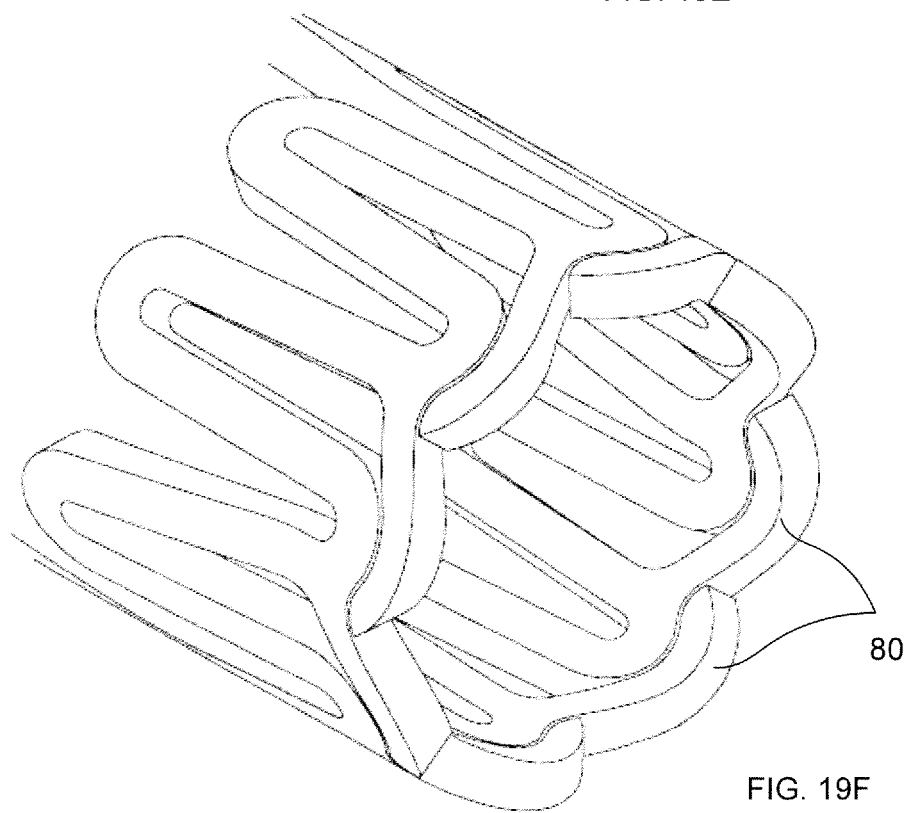
Figure 19G:
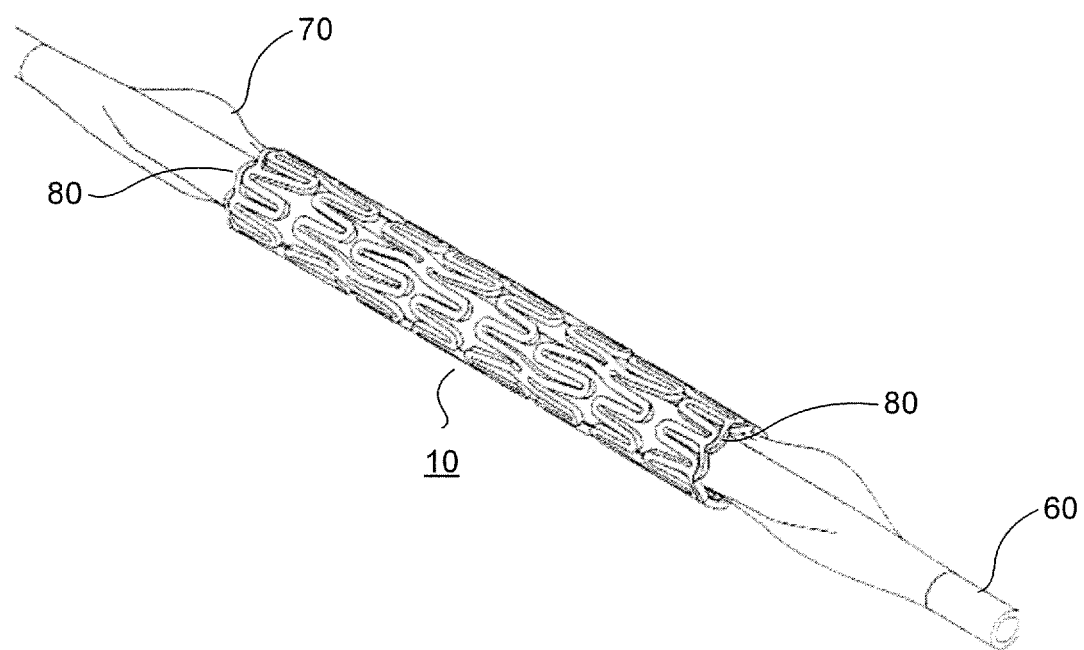

FIG. 19A depicts a planar view of a stent scaffold embodiment showing an alternate embodiment of the locking mechanism 80 at the ends of the stent as manufactured. FIG. 19B depicts FIG. 19A in a crimped position showing an engaged locking mechanism 80. FIG. 19C shows an enlarged planar view of the locking mechanism in the crimped position, while FIG. 19D shows unlocking in a partially expanded configuration. FIGS. 19E and 19F shows oblique views of the end rings with locking mechanism 80 partially engaged (FIG. 19E); crimped (FIG. 19F) and mounted in a balloon catheter (FIG. 19G).

Figure 20A:
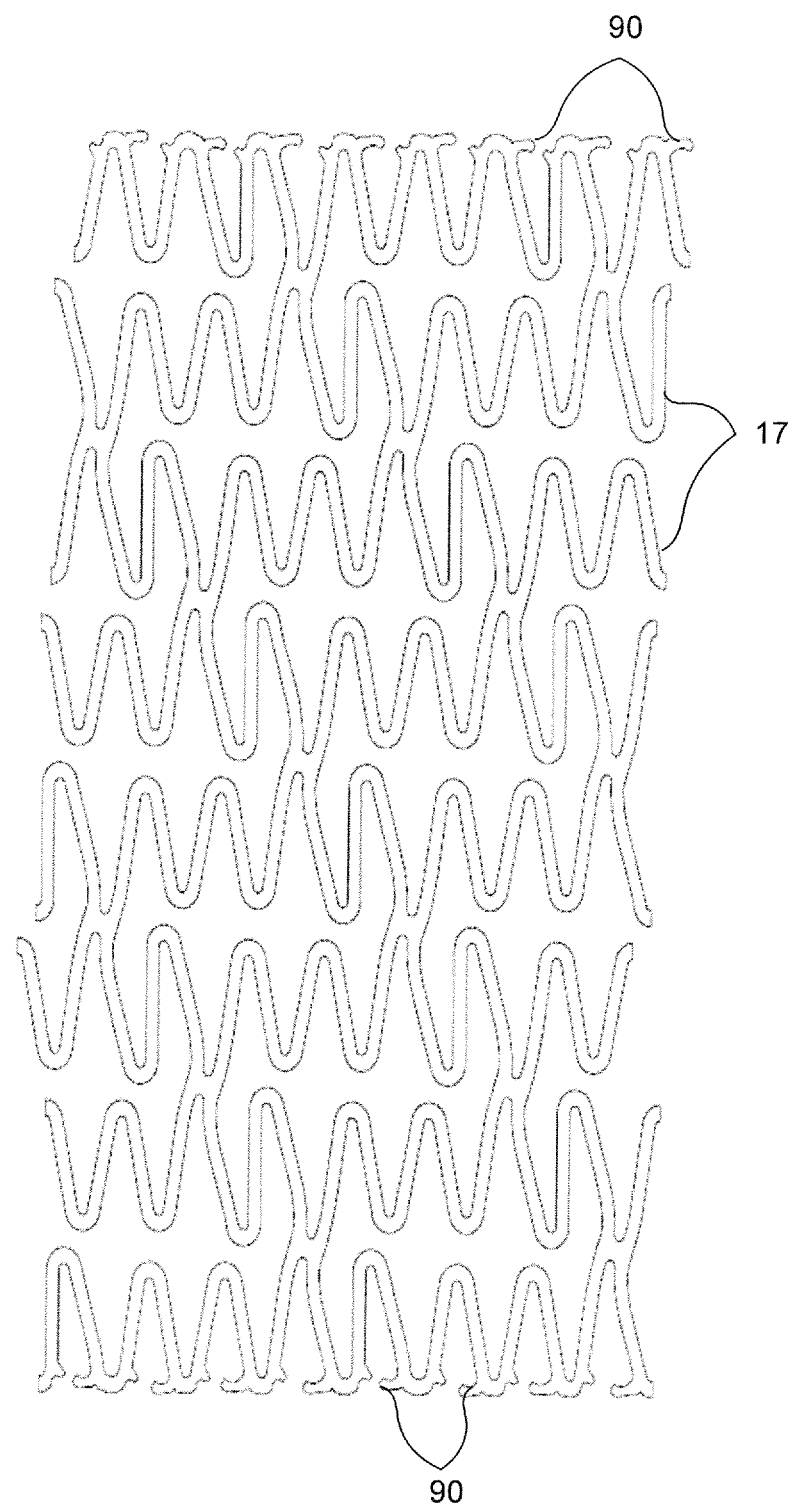
FIG. 20A depicts an planar view of an alternate design locking mechanism of bioabsorbable stent embodiment in an expanded configuration; crimped configuration (FIG. 20B).
Figure 20B:
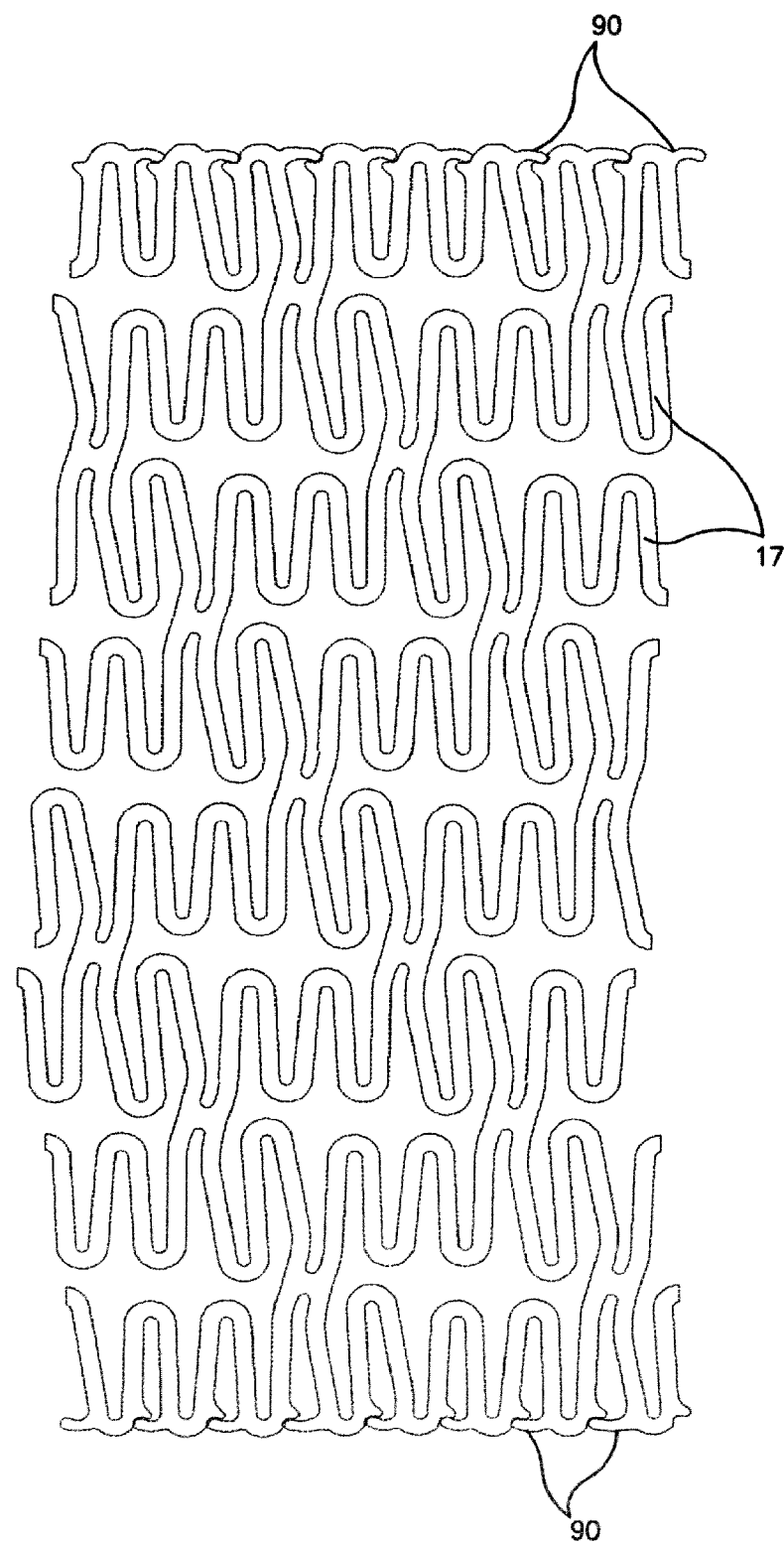
FIG. 20 C is a planar view of an end segment showing a snap-fit locked end in a crimped configuration and expanded (FIG. 20D).
FIGS. 20E and 20F represent oblique views of the stent scaffold of FIGS. 20A-20F in expanded and crimped configurations, respectively.
FIG. 20G illustrates the stent scaffold mounted on a balloon catheter.
Figure 20C:
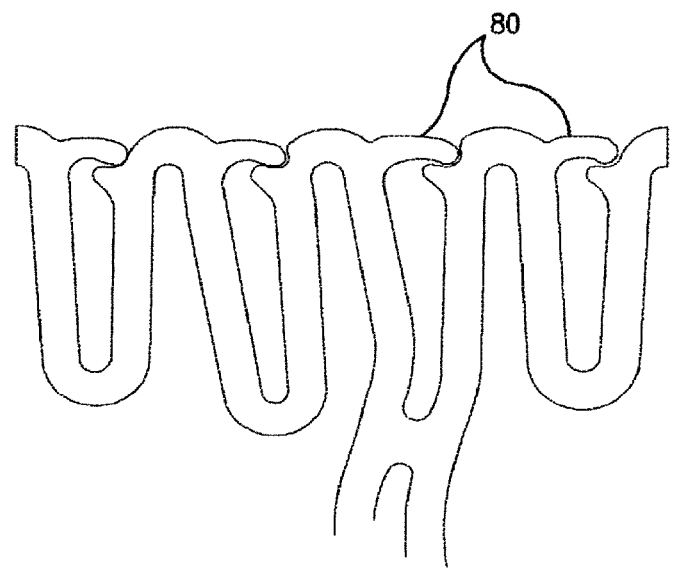
Figure 20D:
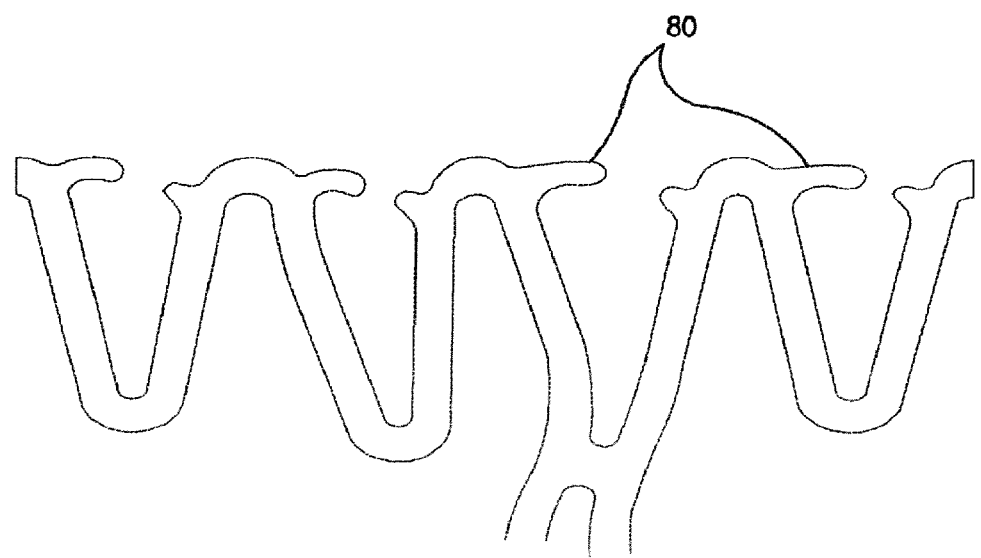
Figure 20E:
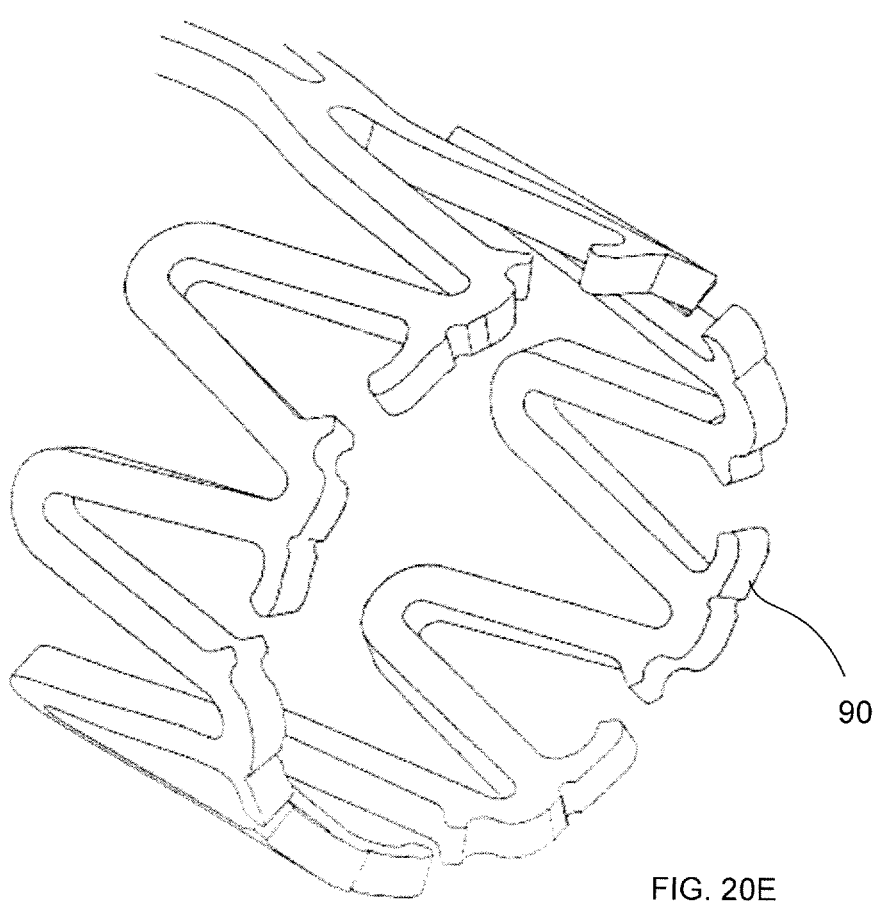
Figure 20F:
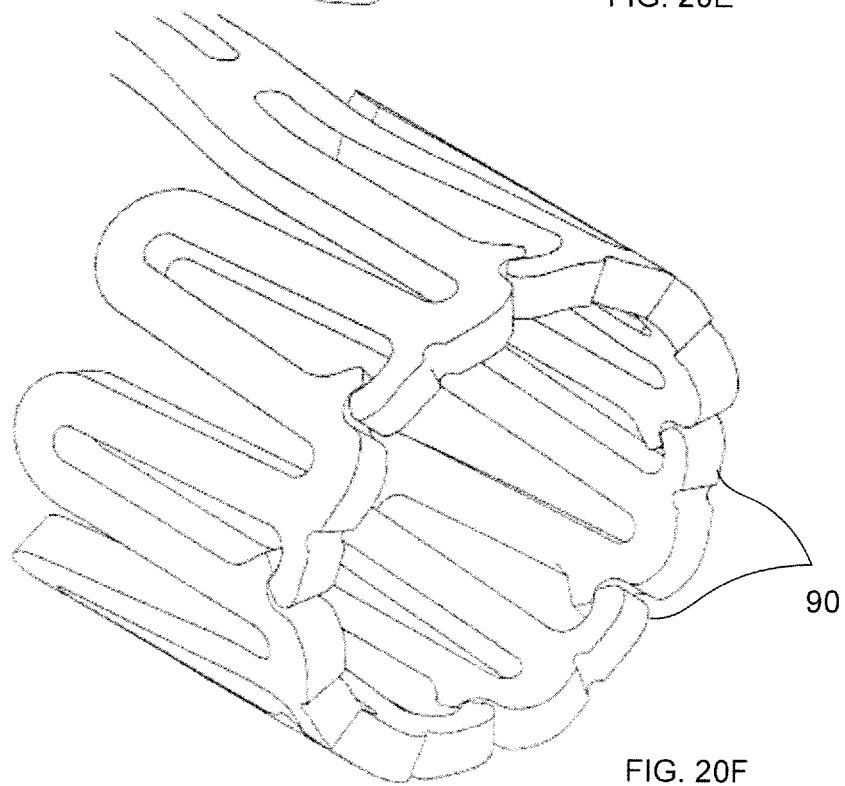
Figure 20G:
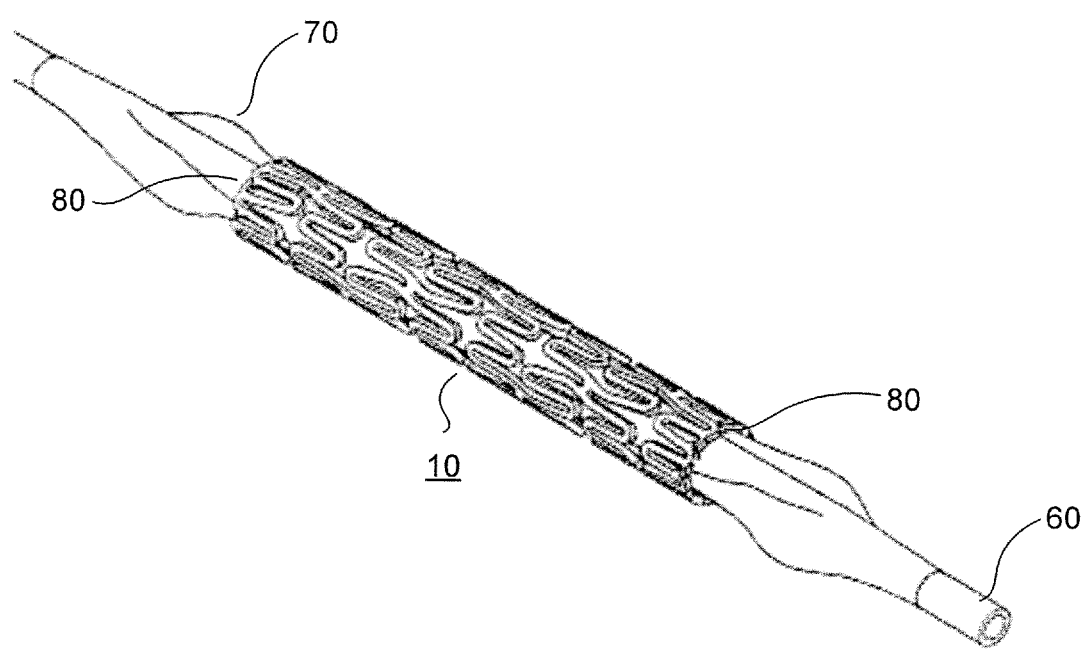

FIG. 20A depicts an planar view of an alternate design locking mechanism of bioabsorbable stent embodiment in an expanded configuration. FIG. 20B depicts the same planar view in a crimped configuration. FIG. 20C is a planar view of an end segment showing a snap-fit locked end in a crimped configuration. FIG. 20D shows the end segment of FIG. 20C when expanded to cause unlocking of locking mechanism 80. FIGS. 20E and 20F represent oblique views of the stent scaffold of FIG. 20C in expanded configuration (FIG. 20E) with unlocked locking mechanism 90 and crimped configuration (FIG. 20F), with locked locking mechanism 90, respectively. FIG. 20G illustrates the stent scaffold of FIGS. 20A-20F mounted on a balloon catheter.

Figure 21:
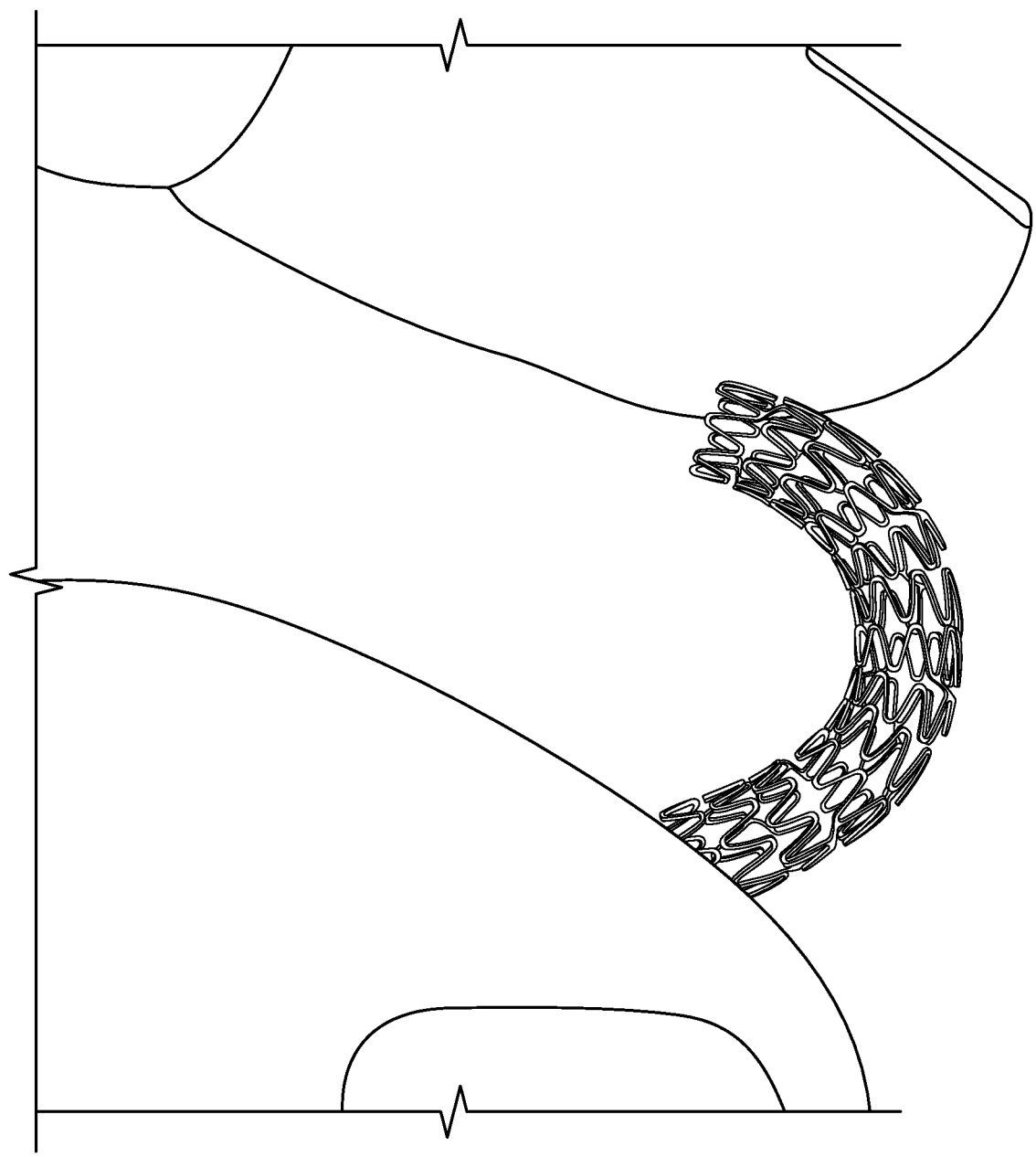
FIG. 21 depicts a photograph of a bioabsorbable stent scaffold embodiment as manufactured being held between a person's thumb and index finger and showing the flexibility of the device.

FIG. 21 depicts a photograph of a bioabsorbable stent scaffold embodiment as manufactured being held between a person's thumb and index finger and showing the flexibility of the device. As can be seen considerable flexibility may exist.

Polymer implant embodiments may be nearly undetectable due to lack of mass density or absence of signal. Therefore, such embodiments may incorporate a radio opaque marker, such a radio opaque dots. Such dots may be produced by applying radiopaque material in paste form into rivet-like depressions or receptacles in or on the scaffold strut elements. As shown, regular patterns of radiopaque dot deposits on the scaffold would advantageously aid in the ease of radiological detection of such implant location.

In one scaffold embodiment, the scaffold comprises a crimpable polymeric stent, which can be inserted by means of a balloon delivery system for vascular implantation. However, the flexible plasticity of the stent scaffold can lead to relaxation of the crimped configuration on the carrier system used for vascular insertion or delivery. Consequently, the crimped scaffold acquires the tendency to "creep" that move off the intended location of the balloon carrier or come loose entirely. Therefore, in preferred embodiments, the polymeric device such as a stent is provided with a safety mechanism for guarding against accidental opening of the scaffold while being mounted or loaded onto a delivery system and during deployment of the crimped device to a desired location within the tubular organ. Multiple safety mechanism are disclosed herein which can be used with a medical device. The securing mechanisms can be designed adjacent to the circumferential distal and proximal end ring struts (secondary meandering strut elements). In specific embodiments, the scaffold has now been furnished with locking means to keep the crimped structure in a securely clamped position to prevent buckling and for secure deployment of the device. In addition, the locking means can prevent a loosening of the crimped configuration of the plastic scaffold from the carrier system during handling. The locking mechanism is affected by structurally interfering design and/or by added frictional properties which may be activated by mutual pressure engagement. According to an embodiment, frictional aspects of the locking mechanism may be affected by selectively modified plastic compositions, wherein ionic or non-ionic additive substances may contribute to secure the crimped configuration of a scaffold.

In specific embodiments, the scaffold employs various designs including snap-fit features at or near the distal and proximal end to lock the scaffold in the crimped position on the carrier portion of the delivery system. In this and other embodiments, one or more snap-fit structures can be designed, positioned at the end meandering strut element of a scaffold structure or alternatively also in certain repeat positions within scaffold structure. As intended in the crimped configuration, the locking mechanism increases stent retention force. Adjacent snap-fit locking features are designed to be continuous or attached to or part of a secondary meandering or ring/hoop structure, and are operatively configured to engage and lock-down the ends of the scaffold device in the crimped position to afford a sufficient retentive force for holding the scaffold in place along the longitudinal axis of the device and maintain uniformity of its diameter. In certain embodiments, and upon expansion of the device, the end meandering element may form a completely straightened ring for added hoop strength of, for example, a stent.

As described above, the device may be provided with a structural locking means in the form of key-in-lock configuration members, wherein the design resembles a snap-fit ball-socket joint type interlocking means, in one embodiment, there is provided one or more nested elemental meandering structures for forming loops or ring-like patterns in an expanded configuration.

The scaffold embodiment may be configured in number of ways. For example, one may use end ring type locking positions in the form of a snap-fit where a cantilever shape or finger strut element fits tightly over an adjacent counterpressuring strut surface when locked down in the crimped configuration of the stent. Locking means comprise in another embodiment, a finger-like cantilever extension that engagingly slides in a snap-fit manner over a commensurately curved surface portion of the adjacent piece of the plastic scaffold strut element. In this embodiment, the securing mechanism works as a break or friction device which creates sufficient friction to keep the scaffold end in the crimped-down position. An alternative locking means is illustrated in locked form of a ball-joint snap-fit locking means.

Another alternative mechanism is a snap-fit locking device wherein the cantilever embodiment utilizes a notch style receptacle form on an adjacent strut element to receive the tip portion of the cantilever.

In one embodiment, the structural locking means of the medical device can be designed in key-in-lock or ball-joint configuration wherein the oppositely oriented cantilever hook-type interlocking means in a locked and unlocked position.

In another embodiment, the medical device can be provided with structural locking means configured in a key-in-lock configuration wherein the design resembles a snap-fit dovetail type interlocking means.

The locking means can be provided in the form of snap-fit features near or at one or both end portions of the scaffold entity so that it may remain in place on the carrier means during delivery to the treatment target area until or unless the expanding carrier system is activated to disengage the device during deployment at implantation. During deployment, the locking mechanism can disengage from one another uniformly. In one embodiment, the locking mechanism can be fully stretched so that the connecting stabilizer rings at one or both ends of the longitudinally meandering scaffold members after implantation into, for example, the luminal wall of a blood vessel or other target area.

In one embodiment structure, meandering struts alternate with each other. Both primary meandering struts and secondary meandering or ringlet strut elements are held in position with respect to each other in the crimped configuration as well as the expanded or implanted configuration by means of special connectors of various shapes located at crossing points between adjacent struts. Each such crossing connector or a select number thereof may be used in a repeat pattern. These connecting elements are capable of keeping the meandering struts of the scaffold embodiment in a regularly spaced position. These connectors are intended to withstand the change from the initial tube confirmation to a tightly crimped position on a delivery bulb/inserting device to a stretchedly expanded configuration. The stretching of such a stent scaffold stresses and crystallizes the component struts and hoops/rings into circularity concomitant with the overall cylindrical or cone-like shape. The strut connecting elements or connectors may be arranged in repeat patterns to stabilize and connect adjacent meandering strut elements. This design is intended to keep the elastic flexible meandering struts located within the tube-like scaffold conformation.

In another embodiment, there is provided a cooling means or condition for immobilizing and stabilizing a plastic scaffold on the carrier system in a crimped and locked down configuration for increasing reliability of the delivery system.

In another embodiment, the medical device comprises a polymeric scaffold structure which can orient and/or crystallize upon strain of deployment, for example during balloon dilation, in order to improve its mechanical properties. These mechanical properties include but are not limited to resistance to compression, recoiling, elastic In another embodiment, the medical device produced from polymers or polymeric compositions which upon breakdown in vivo, the polymer byproducts resulting from such breakdown comprise "friendly" or biocompatible compounds that have very low or substantially no immunogenicity to the host, for example, and no significant granulation tissue can be stimulated to develop in the vascular wall.

In yet another embodiment, the medical device comprises polymers having slow breakdown kinetics which avoid tissue overload or other inflammatory responses at the site of implantation.

In one embodiment, a medical device may have a minimum of 30-day retention in situ of clinically sufficient strength against creep, or break-up, and induces endothelialization after implantation.

An exemplary medical device can be structurally configured to provide the ability to change and conform to the area of implantation and to allow for the normal reestablishment of local tissues. For example, the medical device can transition from a solid polymer state to a "rubbery state" and allows for easier surgical intervention, than, for example, metal stents such as a stainless steel stent. The higher the deformed state, the higher strength that is imparted to the device structural component.

In certain embodiments, the polymer composition can comprise a base polymer which can be present from about 70% to 95% by weight, or from about 70% to 80% by weight of the composition.

In one embodiment, the polymer formulation can comprise from about 70% by weight poly L-lactide (about 2.5 to 3 IV) with the poly L-lactide-co-TMC(70/30 w/w) (1.4 to 1.6 IV).

In another embodiment, the polymer formulation comprises 70% by weight triblock poly L-lactide-co-PEG(99/01) (2.5 to 3 IV) with the poly L-lactide-co-TMC(70/30) (1.4 to 1.6 IV).

In one embodiment, the polymer composition can also comprise a formulation of about 70% by weight diblock poly L-lactide-co-PEG-MME(95/05) (2.5 to 3 IV) with poly L-lactide-co-TMC(70/30 w/w) (1.4 to 1.6 IV).

An embodiment of the biodegradable medical device comprises a base polymer comprising, for example ply L-Lactide or poly D-Lactide, a modifying co-polymer, such as poly L(or D) lactide-co-Tri-methylene-carbonate or poly L(or D)-lactide-co-e-caprolactone as described above.

Polymerization preferably proceeds by block polymerization of D and L isomeric forms so as to achieve a polymeric racemate moiety that enhances the transition from generally amorphous configuration to a expansion related stretch or strain induced crystalline realignment of the polymeric moiety. The mechanical properties concomitantly change from crimpable flexibility to hoop extended rigidity, most particularly the latter change occurring in the expansion of nested and end-positioned rings or hoops from secondary meandering struts.

In one embodiment, pharmaceutical compositions can be incorporate with the polymers by, for example, admixing the composition with the polymers prior to extruding the device, or grafting the compositions onto the polymer active sites, or coating the composition onto the device.

The medical device can comprise any polymeric medical device for implantation including stents, grafts, stent grafts, synthetic vascular grafts, shunts, catheters, and the like.

An exemplary medical device may be a stent, which is structurally configured with a first meandering/sinusoidal elements and having a number of nested second element that when expanded comprises ring-like structural elements. The stent may also comprise snap-fit structures for aiding in crimping and for maintaining the crimped state for deploying into, for example, an artery or a vein, and be able to expand in situ, and conform to the blood vessel lumen to reestablish blood vessel continuity at the site of injury. In alternate embodiments, the stent may be configured to have many different arrangements, patterns or designs so that it is crimpable when loading and expandable and flexible but compression-resistant or resilient at physiological conditions once deployed. Moreover, the expanded implant may display mechanical properties such as a degree of rigidity and concomitant flexibility preventing dislocation or creep.

Various embodiments of biodegradable polymeric stents, and/or stent walls with different configurations. For example, the stent is a tubular structure comprising a scaffold wherein the strut elements are designed to allow blood to traverse through open spaces between the elements. In particular the meandering struts are spaced so that most of the adjacent tissue surface remains available for contact with blood. The particular stent design features include different radial and longitudinal parameters depending on the size of the stent to be deployed. A stent configuration can be varied such as bifurcated or configured to allow for further deployment to other vessels distal to the site of initial implantation.

A stent can contain a uniform and flexible scaffolding modified with side-branches. Accordingly, after initial deployment of the stent in situ, a second stent can be inserted through the luminal walls of the first stent.

In an embodiment, the medical device can be modified to include a radio-opaque, or radiolucent material for detecting its location after deployment or to ascertain the effects of long-term use (6 months or 2 years). There are different types of modifications available, such as e.g. diffuse or spot marking of the scaffold. Accordingly the radio-opaque materials can be incorporated directly in the initial plastic composition either as an admixture or covalently bound component. Alternatively, the radio-opaque material can be placed in a plurality of specific spot receptacles regularly distributed on or in the scaffold. Or the radio-opaque or radiolucent materials can by applied as part of a thin coating on the scaffold.

Therefore, the contrast detection enhancement of tissue implants by electron-dense or x-ray refractile markers is advantageous. Such markers can be found in biodegradable spot depots filled with radiopaque compositions prepared from materials known to refract x-radiation so as to become visible in photographic images. Suitable materials include without limit, 10-90% of radiopaque compounds or microparticles which can be embedded in biodegradable moieties, particularly in the form of paste like compositions deposited in a plurality of cup shaped receptacles located in preformed polymeric scaffold strut elements.

The radiopaque compounds can be selected from x-radiation dense or refractile compounds such as metal particles or salts. Suitable marker metals may include iron, gold, colloidal silver, zinc, magnesium, either in pure form or as organic compounds. Other radiopaque material is tantalum, tungsten, platinum/iridium, or platinum. The radiopaque marker may be constituted with a binding agent of one or more aforementioned biodegradable polymer, such as PLLA, PDLA, PLGA, PEG, etc. To achieve proper blend of marker material a solvent system is includes two or more acetone, toluene, methylbenzene, DMSO, etc. In addition, the marker depot can be utilized for an anti-inflammatory drug selected from families such as PPAR agonists, steroids, mTOR inhibitors, Calcineurin inhibitors, etc. In one embodiment comprising a radioopaque marker, iron containing compounds or iron encapsulating particles are cross-linked with a PLA polymer matrix to produce a pasty substance which can be injected or otherwise deposited in the suitably hollow receptacle contained in the polymeric strut element. Such cup-like receptacles are dimensioned to within the width of a scaffold strut element. Heavy metal and heavy earth elements are useful in variety of compounds such as ferrous salts, organic iodine substances, bismuth or barium salts, etc. Further embodiments can utilize natural encapsulated iron particles such as ferritin that may be further cross-linked by cross-linking agents. Furthermore, ferritin gel can be constituted by cross-linking with low concentrations (0.1-2%) of glutaraldehyde. The radioopaque marker may be applied and held in association with the polymer in a number of manners. For example, the fluid or paste mixture of the marker may be filled in a syringe and slowly injected into a preformed cavity or cup-like depression in a biodegradable stent strut through as needle tip. The solvents contained in the fluid mixture can bond the marker material to the cavity walls. The stent containing radiopaque marker dots can be dried under heat/vacuo. After implantation, the biodegradable binding agent can breakdown to simple molecules which are absorbed/discharged by the body. Thus the radiopaque material will become dispersed in a region near where first implanted.

The scaffold mechanical properties are time tested in situ for any retention of recoil and the presence of restenotic tissue. Similarly, scaffold polymer biodegradation and metabolism may be assessed by quantitative change measurement in echogenicity and tissue composition. Regional mechanical properties may be assessed by palpography (6 months; 2 years). Mass reduction over time of polymer degradation may be assessed by OCT (6 months; 2 years). Binary restenosis may be quantitatively measured with MSCT(18 m). The experimental evidence supports the advantages of the biodegradable and absorbable scaffold as used for example in a stent. It has been found that the scaffold performs like a metallic drug eluting stent (DES) in terms of acute delivery and conformity. However, it has been found that the emplaced scaffold is naturally absorbed and fully metabolized. Therefore, the bioabsorbable scaffold, which may be in the form of a tube shaped stent, is metabolized completely leaving no permanent implant and leaves behind a healed natural vessel or tissue. The scaffold of this invention is compatible with CT imaging.

A process for making an exemplary medical device comprises: preparing a suitable polymer composition with or without one or more pharmaceutical substances; molding or extruding the polymer composition to configure structurally the device for implantation. In the case of a stent, a tube shaped structure is formed and it is subsequently cut with, for example, the aid of a laser to form desired patterns.

In one embodiment, a method for fabricating the medical device comprises preparing a biodegradable polymeric structure; designing said polymeric structure to be configured to allow for implantation into a patient; laser cutting said structure into patterns configured to permit traversing of the device through openings and to allow for crimping of the device. Preferably, the patterned structure contains the aforementioned locking means for stabilizing the crimped device so as to retain it securely on the carrier/implant system.

In another embodiment, closure means of locking devices for aiding in crimping and loading a scaffold configuration may be further chemically modified or enhanced by adding biocompatible non-ionic or ionic agents to the scaffold or scaffold composition or in the form of layers or grafts. These modified anionic, cationic or nonionic layers can be uniform or minutely stippled onto the interlocking surfaces. The dosage levels of the cationic or anionic agents which may also be surfactants may range from 0.01-10% by weight. External application of such ionic agents is preferred for easy soluble removal after expansion in situ. Low dosage levels of non-ionic agents are suitable for enhancing frictional interaction particularly between parts of locking mechanism. Preferred are nonionic agents which may be FDA approved at dosage levels ranging from 0.05-2.5%. An embodiment for the friction-enhanced scaffold, or particularly, the interacting lock surfaces, provides non-ionic doping of the modified layers. Suitable nonionic agents may be selected from chemicals such as ethoxylated fatty amines, fatty acid esters, and mono- and diglycerides.

While the invention has been particularly shown and described with reference to particular embodiments, it will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A bioabsorbable scaffold comprising expansion-crystallizable bioabsorbable polymer, the scaffold having a proximal open end and a distal open end, and being crimpable and expandable, comprising:
   a first multicomponent strut pattern helically coursing from the proximal open end to the distal open end of the scaffold; and
   a second multicomponent strut pattern helically coursing from the proximal open end to the distal open end of the scaffold.

2. The scaffold of claim 1, wherein the first multicomponent strut pattern is substantially the same in configuration throughout the scaffold.

3. The scaffold of claim 1, wherein the second multicomponent strut pattern is substantially the same in configuration throughout the scaffold.

4. The scaffold of claim 1, wherein the first and second multicomponent strut patterns are substantially the same in configuration throughout the scaffold.

5. The scaffold of claim 1, wherein the component of the first multicomponent strut pattern that opposes from about 120° to about 180° the component of the second multicomponent strut pattern are substantially the same in configuration.

6. The scaffold of claim 5, wherein the components of the first and second multicomponent struts that oppose form a stylized H configuration, a stylized X configuration, a stylized S configuration, a stylized 8 configuration, or a stylized I configuration.

7. The scaffold of claim 1, further comprising a third multicomponent strut pattern helically coursing from the proximal open end to the distal open end of the scaffold.

8. The scaffold of claim 7, further comprising a fourth multicomponent strut pattern helically coursing from said proximal open end to said distal open end of said scaffold.

9. The scaffold of claim 8, further comprising a fifth multicomponent strut pattern helically coursing from said proximal open end to said distal open end of said scaffold.

10. The scaffold of claim 1, wherein each helix of both of the multicomponent strut patterns turns about the scaffold in a left-handed screw direction.

11. The scaffold of claim 1 wherein each helix of both of the multicomponent strut patterns turns about the scaffold in a right-handed screw direction.

12. The scaffold of claim 1, wherein at least one helix of both of the multicomponent strut patterns turns about the scaffold in a left-handed screw direction while another helix turns in a right-handed screw direction.

13. The scaffold of claim 1, wherein all of the helices of the multicomponent strut patterns turns about the scaffold in the same handed direction.

14. A bioabsorbable stent having a proximal open end and a distal open end, and comprising a plurality of helically coursing multicomponent strut patterns from the proximal open end to the distal open end of the stent, wherein the stent comprises expansion-crystallizable bioabsorbable polymer.

15. The stent of claim 14, wherein each helix of the multicomponent strut patterns turns about the stent in a left-handed screw direction.

16. The stent of claim 14, wherein each helix of both of the multicomponent strut patterns turns about the stent in a right-handed screw direction.

17. The stent of claim 14, wherein at least one helix of the multicomponent strut patterns turns in a left-handed screw direction while another helix turns about the stent in a right-handed screw direction.

18. The stent of claim 14, wherein all of the helices of the multicomponent strut patterns turn about the stent in the same handed direction.

* * * * *